United States Patent [19]
Tümer

[11] Patent Number: 5,821,541
[45] Date of Patent: Oct. 13, 1998

[54] METHOD AND APPARATUS FOR RADIATION DETECTION

[76] Inventor: Tümay O. Tümer, 107 Sweetwood Ct., Riverside, Calif. 92507

[21] Appl. No.: 784,176

[22] Filed: Jan. 15, 1997

Related U.S. Application Data

[60] Provisional application No. 60/011,135, Feb. 2, 1996.
[51] Int. Cl.⁶ ...................................................... G01T 1/24
[52] U.S. Cl. ................................ 250/370.09; 250/363.03
[58] Field of Search ................................. 378/37, 4, 98.8; 250/370.09, 369, 367, 366, 363.02, 363.03, 363.04, 370.01

[56] References Cited

U.S. PATENT DOCUMENTS

| | | | |
|---|---|---|---|
| 4,857,737 | 8/1989 | Kamae et al. | 250/370.09 |
| 5,567,944 | 10/1996 | Rohe et al. | 250/370.09 |

*Primary Examiner*—David P. Porta
*Attorney, Agent, or Firm*—David G. Beck; Townsend and Townsend and Crew

[57] ABSTRACT

A detection system is provided. In one embodiment a silicon Compton recoil electron detector uses the Compton double scatter technique with recoil electron tracking to detect medium energy gamma rays from 0.3 to 30 MeV. Two detector layers are required; a silicon microstrip hodoscope and a calorimeter. The incoming photon Compton scatters in the hodoscope. The second scatter layer is the calorimeter where the scattered gamma ray is totally absorbed. The recoil electron in the hodoscope is tracked through several detector planes until it stops. The x and y position signals from the first two planes of the electron track determine the direction of the recoil electron while the energy loss from all planes determines the energy of the recoil electron. In another embodiment of the invention, the Compton double scatter technique with recoil electron tracking is used to detect x-rays from 300 to 2,000 keV. This embodiment is useful for nondestructive, real time inspection of munition items. In another embodiment of the invention, the invention is used to provide a high sensitivity, high spatial resolution and electronically collimated single photon emission computed tomography system which is sensitive from 81 keV to 511 keV gamma ray photons. In another embodiment, a high sensitivity three-dimensional scintimammography system is provided which utilizes gamma ray imaging. In another embodiment, a Compton scatter positron emission tomography system is provided.

6 Claims, 38 Drawing Sheets

| SCINTILLATOR | DENSITY G/CM$^3$ | LIGHT OUTPUT % OF NaI(Tl) | MAX EMISSION $\lambda$ NM | DECAY TIME NSEC | REFRACTIVE INDEX | HYGROSCOPIC |
|---|---|---|---|---|---|---|
| NsI(Tl) | 3.67 | 100 | 415 | 230 | 1.85 | YES |
| CsI(Tl) | 4.51 | 40-50 | 530 | 1,000 | 1.80 | SLIGHTLY |
| CsI(Na) | 4.51 | 80-85 | 430 | 630 | 1.84 | YES |
| BGO | 7.13 | 10-20 | 460 | 300 | 2.15 | NO |
| CdWO$_4$ | 7.90 | 30-50 | 470 | 70 | 2.36 | NO |
| CsF | 4.11 | 5 | 390 | 5 | 1.48 | VERY |
| HPGe | 5.32 | N/A | N/A | N/A | N/A | NO |

FIG. 5.

| SYSTEM | COLLIMATOR | ENERGY RES. | SPATIAL RES. (FWHM) TANGENT/RADIAL (MM) | POINT SENS. CTS $s^{-1}$ $\mu Ci^{-1}$ | VOLUME SENSITIVITY CTS $s^{-1}$ $(\mu Ci/CC)^{-1}$ $CM^{-1}$ |
|---|---|---|---|---|---|
| TRI-SPECT | FAN BEAM | 10.2% | 7.24/10.03 @ 10 CM | 6.5 | 3,540 @ 20% EN. WIN. |
| THIS PROPOSAL | NONE | 1.4%–1% | 5.5–1.8 BOTH @ 10 CM | 1,500 | 500,000 @ 2% EN. WIN. |

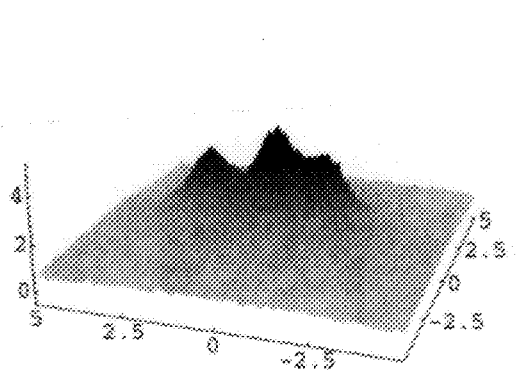
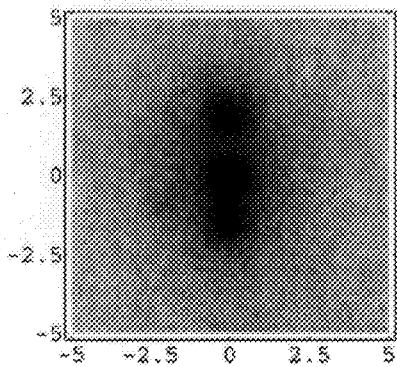
FIG. 48.   FIG. 49.
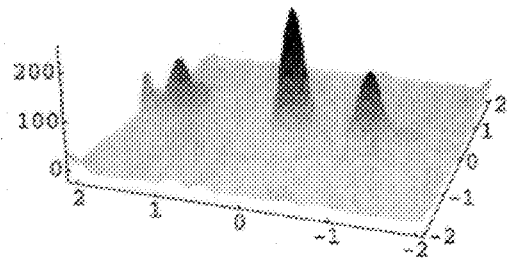
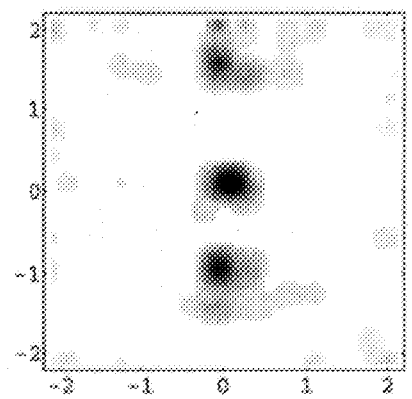
FIG. 50.   FIG. 51.
| RADIONUCLIDE | HALF-LIFE (HR) | ENERGY (keV) | %γRAY INTENSITY |
|---|---|---|---|
| THALLIUM-201 | 73.0 | 69, 71, & 80 (K X-RAYS) | 94.5 |
| TECHNETIUM-99m | 6.0 | 141 | 100 |
| IODINE-123 | 13.3 | 159 | 100 |
| IODINE-131 | 192.0 | 364, 637 | |
| FLUORINE-18 | 1.8 | 511 | 96.9% β+DECAY |
FIG. 52.

| RADIONUCLIDE | HALF-LIFE (MIN) | END-POINT ENERGY (MeV) | % $\beta^+$ DECAY | MAXIMUM RANGE (MM) | DAUGHTER |
|---|---|---|---|---|---|
| CARBON-11 | 20.40 | 0.97 | 99.8 | 4.1 | $^{11}$B, STABLE |
| NITROGEN-13 | 9.96 | 1.19 | 100.0 | 5.1 | $^{13}$C, STABLE |
| OXYGEN-15 | 2.07 | 1.70 | 99.9 | 7.3 | $^{15}$N, STABLE |
| FLUORINE-18 | 109.7 | 0.635 | 96.9 | 2.4 | $^{18}$O, STABLE |
| GALLIUM-68 | 68.1 | 1.88 | 90.0 | 8.1 | $^{68}$Zn, STABLE |
| BROMINE-75 | 101.0 | 1.70 | 76.0 | 7.3 | $^{75}$Se, RADIOACTIVE 118.5 DAYS |
| STRONTIUM-82 | 1.3 | 3.15 | 96 | 15.6 | $^{82}$Kr, STABLE |

*FIG. 62.*

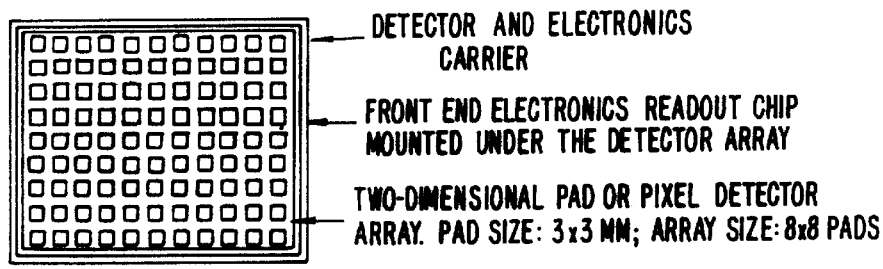
FIG. 66.
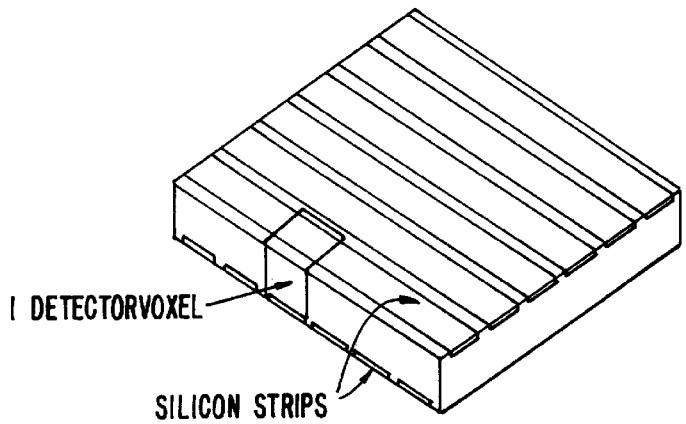
FIG. 67.
| COMPOSITION | CdTe | Cd$_{96}$Zn$_{04}$Te | Cd$_8$Zn$_2$Te |
|---|---|---|---|
| Zn FRACTION, x | 0 | 0.04 | 0.20 |
| RESISTIVITY (OHM-CM) | 3.0 x 10$^9$ | 2.5 x 10$^{10}$ | 1.5 x 10$^{11}$ |
| ETCH-PIT-DENSITY (CM-2) | 1.8 x 10$^5$ | 1.0 x 10$^4$ | 0.5 x 10$^4$ |
| DCRC LINEWIDTH (FWHM, ARC-SECONDS) | N.M. | 14 | 12 |
| PL LINEWIDTH (FWHM, MEV) | 0.3 | 1.0 | 2.2 |
FIG. 68.

| SYSTEM | SEPTA | ENERGY RES. | TRANSAXIAL RES. FWHM (MM) | AXIAL RES. FWHM (MM) | SLICE SENSITIVITY CTS $s^{-1}$ ($\mu$Ci/CC)$^{-1}$ |
|---|---|---|---|---|---|
| S9100B | INTERPLANE | 20% | 5 | 6 | 8,700 |
| THIS PROPOSAL | NONE | 1.3% | $\leq 3$ | $\leq 3$ | 8,300 |

METHOD AND APPARATUS FOR RADIATION DETECTION

This application claims benefit of USC Provisional Appln. Ser. No. 60/011,135 filed Feb. 2, 1996.

The present invention relates generally to detection systems, and more particularly, to a method and apparatus for detecting gamma rays, x-rays, and positrons.

BACKGROUND OF THE INVENTION

The Defense Department and others have identified a myriad of problems which are associated with implementing the Strategic Defense Initiative (SDI). Of particular concern are: (i) medium energy (i.e., from 0.3 to 30 MeV) gamma ray detection for detecting radioactive materials, neutron capture reaction products and interaction of high energy particles with matter; (ii) exoatmospheric mid-course discrimination of nuclear warheads from decoys; (iii) determination of destroyed nuclear warheads; (iv) precursor nuclear blast monitoring; (v) nuclear powered satellit monitoring; (vi) detection of covert satellites with concealed nuclear warhead capabilities; and (vii) the detection and monitoring of nuclear material which can be used to manufacture nuclear warheads.

The dominant absorption process for gamma rays of 0.3 to 30 MeV is the Compton interaction for most materials. At present the best method to detect these gamma rays is the Compton double scatter technique. The Compton double scatter technique has the unique property that both the direction and the energy of the incoming photon can be determined. Single Compton scattering alone gives neither the direction nor the energy of the incident gamma ray. The photoelectric effect can be used to measure the energy of low energy gamma rays but their directions cannot be determined unless collimators or coded apertures are used which decrease the sensitivity and limit the field-of-view.

Present detectors which use the Compton double scatter technique determine the direction of the incoming photon to a ring in the sky, since the direction of the recoil electron at the first scatter can not be measured. The symmetry of the double scatter method cannot normally distinguish between the front (through the aperture) or back (through the calorimeter) entry of the incident photon. Time-of-flight measurement is normally used in Compton double scatter detectors to select gamma rays coming through the field-of-view. This is done by separating the hodoscope (first scatterer) and the calorimeter (second scatterer) by about 1.5 meters.

The realtime inspection of munition items has always been a high priority with the US Army. The problem is not just quality control. Munitions, especially ammunition, can be extremely dangerous if defects develop that might increase the chance of a detonation, leakage, etc. The defect could also render the ammunition ineffective which could lead to serious consequences during deployment. The Army has always carried out inspection of munitions. In the past it was usually carried out by visual inspection of radiographs. Many of the defects formed during or after the manufacturing are internal and cannot be identified visually. Nowadays x-ray inspection is used widely which gives a 2-dimensional image of the internal structure of the munition items.

The x-ray images were recorded on photographic film which required post development and real time inspection. This process was significantly improved by introducing scintillators to detect the x-rays. The scintillator is followed by an image intensifier, which is viewed by a camera with digital output. Such systems are effective and are used extensively by the Army. They produce high resolution images of the munition items in real time. A major drawback is the radiation damage suffered by the scintillator which degrades the inspection system over time. Therefore, the camera system has to be moved out of the x-ray beam between each measurements.

These types of systems observe the integrated signal coming from the x-ray source which is attenuated selectively by the density variations inside the munition item. Such a system cannot measure the direction and the energy of the incident x-ray photon. It only provides the integrated position information. The x-ray photons during attenuation undergo scattering by the Compton scatter process, which is significant for 300 keV to 2 MeV energies, and can enter the aperture of the detector producing background. Therefore, such systems have a low signal-to-noise ratio.

Emission computed tomography (ECT) and associated technologies are relatively new scientific tools that have allowed scientists and physicians to address problems in physiology and biochemistry in the human body with low risk. Radioisotopes have become clinical tools in medical research, diagnosis and therapy and their use is increasing steadily. ECT systems are mainly used for the detection and imaging of the radiation produced by radiotracers and radiopharmaceuticals. They have a special role in medical study and diagnosis that the x-ray computed tomography (X-Ray CT) and nuclear magnetic resonance imaging (NMR) systems cannot achieve. They have the potential to image organ functions (in real time for high sensitivity systems) by administering biologically active radiopharmaceuticals into the patient specifically chosen for that organ. The two major instruments presently used are SPECT and PET. They are used in many different studies such as cerebral glucose consumption, protein synthesis evaluation, cerebral blood flow and receptor distribution imaging, oxygen utilization, stroke, heart, lung, epilepsy, dementia, oncology, pharmacokinetics, psychiatric disorders, radio labelled antibody and cardiac studies. These instruments have progressed greatly in recent years with the advancements in γ-ray detectors. The SPECT and PET use different types of radiotracers and the metabolic activities imaged are mostly different. Therefore, these two instruments complement rather than compete with each other. The SPECT detectors are especially useful for heart and brain imaging.

SPECT dates back from the early 1960s, when the first transverse section tomographs were presented by Kuhl and Edwards (1963), who used a rectilinear scanner and analog back-projection methods. With the availability of computer systems and the impetus of computer-assisted tomography using transmitted x-rays, nuclear medicine instruments were modified, and a number of mathematical approaches to tomographic reconstruction were developed in the early 1970s. Rotating Anger cameras and advances in computers opened the way to three-dimensional SPECT systems. Recently interest in SPECT increased as mathematical reconstruction techniques improved. They allowed for attenuation compensation, scattered radiation correction and the availability of new radiopharmaceuticals with higher uptake in the brain and other organs. The major limiting factors for the SPECT systems presently are the sensitivities ($\approx 10$ Cts s$^{-1}$ $\mu$Ci$^{-1}$ point and $\approx 1,000$ Cts s$^{-1}$ cm$^{-1}$ volume), resolution (7 to 12 mm FWHM), size and cost.

Present SPECT systems mainly use the rotating Anger camera. Many different variations of the Anger camera and other smaller size rotating single or dual instruments have been designed and used. Most of the commercial instruments use NaI(Tl), CsI(Tl), CsF, BaF$_2$, BGO and other related crystal detectors. The majority of the commercial instruments use the Anger cameras made of NaI(Tl) crystals. All commercial SPECT instruments use collimators for determination of the direction of the incident γ-rays. The main types are parallel and converging collimators. The converging fan or cone beam collimators produce higher sensitivity but increase the complexity of the data analysis. Pinhole and slit collimators are also used. The collimators for high resolution systems eliminate at least 99.9% of the incident γ-rays. A typical collimator hole is about 1 mm$^2$ in area and ¾" long. Increasing collimator resolution decreases sensitivity and vice versa. Collimators are made of high atomic number, Z, materials such as lead which also produces considerable amount of scattered γ-rays on the inside surface of the collimator and increases the scattered photon background. The Anger cameras are normally rotated on a gantry around the patient for about 20 min to acquire sufficient data for a reasonable image. The spatial resolutions limited to about 8 to 12 mm and expected to reach 6 mm in the future. The best energy resolutions at γ-ray energies are about 10% which limit their ability to discriminate scattered photon background. Commercially available SPECT systems include ADAC ARC, GE Starcam, Elscint APEX, Trionix Triad, Digital Scintigraphics ASPECT and University of Michigan SPRINT II. Triad uses 3 Anger cameras. ASPECT has a cylindrical detector. Recently some use of multi-wire proportional gas chambers was reported. These detectors have excellent position resolution approaching silicon strip detectors but they have very low γ-ray absorption efficiency due to their low density.

A similar technique uses high energy resolution germanium detectors in the first scatter plane and a conventional Anger camera in the second. The γ-ray photons from the patient are scattered by the germanium in the first plane and absorbed by the NaI(Tl) in the Anger camera in the second plane. The first plane has a low scatter efficiency and the second plane, due to its large size and lack of mechanical collimator, has excessive single count rates (~1×10$^7$ cps in a 20 cm diameter 20 cm long standard phantom with 1 $\mu$Ci/cc $^{99m}$Tc uniformly distributed within its volume). The angular resolution is low (5° FWHM translating to about 9 mm spatial resolution for a point source at 10 cm), and it is not possible to increase the geometric angular resolution further. Germanium detectors are very expensive and require cooling to cryogenic temperatures. Although successfully tested in the laboratory with good sensitivity, about 20 times a mechanical parallel-hole collimated SPECT system, this detector was not commercialized.

A multiple pinhole collimated SPECT system has been proposed which is specially designed for brain imaging and uses a multiple pinhole camera where each pinhole is viewed by a CdZnTe pixel detector with 64×64 pixels of 0.4 mm×0.4 mm pixel area. The pixel detectors are developed by Aurora and the readout chip is designed by Hughes Technology Center. This instrument is expected to achieve a reconstructed volume resolution of 4–5 mm. It is expected that 10 million photons will be detected in 2 minutes after an injection of 20 $\mu$Ci$^{99m}$Tc labelled HMPAO.

Each year in the U.S., approximately 180,000 women are diagnosed with breast cancer and 46,000 women die of this disease. In all, 10%–11% of all women can expect to be affected by breast cancer at some time during their lives. The causes of most breast cancers are not yet understood. Screening and early diagnosis are currently the most effective ways to reduce mortality from this disease. Although mammography is often quite effective in helping to detect breast cancer, it cannot tell whether the lesion is benign or cancerous. Majority of detections turn up as benign tumors when the biopsy is carried out. Biopsy is a traumatic and sometimes disfiguring experience for the patient and a very costly process. A less traumatic and lower cost process which can tell if the patient has benign or malignant tumor can improve the early detection of breast cancer. Such a process may also be used for screening patients with dense breast who cannot be screened with mammography.

Mammography is the most effective means of detecting nonpalpable breast cancer. However, its specificity is only 20–30%, with a sensitivity of 85%. One out of 2 to 6 biopsies performed following diagnosis by mammography are malignancies. In physical examination results, one out of 5 to 9 biopsies are found to be malignant. Normally several biopsies are performed per lesion. It is important to improve the specificity of mammography to reduce errors, patient trauma and disfiguration from unnecessary biopsies. It is also important to reduce health care costs by decreasing the number of unnecessary biopsies. To detect 100,000 non palpable cancers 500,000 biopsies were performed at approximately $5,000 per biopsy, a total cost of $2.5B. A reduction of 50% will save about $1.2B per year. Therefore, a new diagnostic imaging technique that can be used as an adjunctive imaging modality to positive mammograms could aid in diagnosis, reduce errors and provide cost reductions.

Palpable mass abnormalities of the breast are often difficult to evaluate mammographically, especially in patients with fibrocystic change and dense or dysplastic breasts, therefore potential for making interpretational errors is large. About 35% of older women over 50 and 70% of the woman under 50 have dense breasts. For example, it is found that invasive lobular carcinoma in dense breasts can attain a size of several centimeters and may still lack mammographic signs. About 50% of all preinvasive cancers do not show mammographically significant calcifications, decreasing the chance of detecting malignant tumors. There are also mammographically occult breast cancers that are not on a mammogram. This is a situation where interpretational error in mammography is close to 100%. Once a patient is found to have a condition in which mammography is difficult, the patient should be imaged by another modality.

Patients who are in a high risk category for the development of breast cancer (i.e., patients with a family history of breast cancer, patients with prior histologic evidence of cellular atypia, patients with a prior history of breast cancer who have undergone lumpectomy and radiation therapy) may be difficult to evaluate and follow mammographically because of a dense fibroglandular pattern of physical changes caused by radiation. Currently, the only established method to resolve such a dilemma is random tissue biopsies in a suspicious area which is usually attended by high nonmalignant-to-malignant biopsy ratios. These cases may be evaluated by a technique that is not affected by dense fibroglandular patterns.

The advantages of the coincidence method for the detection and collimation of positron emitting radionuclides was recognized in the early 1950s. In the early 1960s a positron scanner to locate brain tumors was developed. One of the considerable advantages of utilizing positron emitting labels for in vivo imaging studies is the very high efficiency that can be achieved through the coincidence collimation of the annihilation radiation. The first positron emission tomography (PET) system was developed in 1975. More recently, the utilization of photon time-of-flight information using fast scintillators has further improved the SNR that can be obtained in images of the distribution of positron emitting radionuclides. PET system transaxial resolutions are about 3.5 mm FWHM and depends on the radionuclide and the detector size used. Spatial resolutions as low as 1.75 mm have been reported. Positron emitting radionuclides such as $^{11}$C, $^{13}$N, $^{15}$O and $^{18}$F can be used in radiopharmaceuticals with chemical characteristics desirable for the study of physiological processes. This and its excellent reconstruction ability rendered PET the system of choice. The short life time of these radionuclides is also useful because it permits the administration of large doses of activity with tolerable radiation exposure of the patient and enables repeated studies to be performed. PET is an essential tool for both research and also medical diagnosis.

Present PET systems use bismuth germanate oxide (BGO) crystals. BGO has the highest effective atomic number and stopping power of any scintillator crystal available today. This translates into a higher photopeak fraction and a lower Compton continuum than other crystals such as NaI and $BaF_2$. Gadolinium orthosilicate (GSO) crystal is an alternative which has a slower decay time but larger pulse yield and higher cost but it comes close to BGO stopping power but cannot fully replace it. $PbCO_3$ crystals nearly equal to BGO in stopping power but the light output is about 10 times lower. Some of the commercially available PET systems are the S9100 series from General Electric Medical Systems, Siemens ECAT, HEADTOME-IV and Rutherford Appleton Laboratory Mark II positron camera (MUP-PET).

The BGO based detectors are bulky and expensive. Their spatial and energy resolutions are not expected to improve much better than 3 mm and 20% (some manufacturers report 17%), respectively. Therefore, a radically new approach is necessary to reach spatial and energy resolutions much better than that of BGO.

One semi-radical approach recently proposed is PET detectors using a combination of $BaF_2$ crystals and multi-wire proportional gas chambers (MWPC). These detectors use the fast scintillation light component centered at 220 nm with less than 1 ns decay time from $BaF_2$. They detect this light output using MWPC with tetrakis-(di-methylamino)-ethylene vapor. The emission is very low and only about 7.6% is converted to photoelectrons which gives about 6 photoelectrons in the wire chamber when small crystals are used. They may have better spatial resolution approaching 3 mm but they have low efficiency in detecting 511 keV photons. This technique is in the experimental stage and not yet commercialized.

From the foregoing, it is apparent that an improved blower fan motor capable of efficiently running at high speeds is desired.

SUMMARY OF THE INVENTION

The present invention provides a detector with the ability to detect 0.3 to 30 MeV gamma rays emitted by the radioactive material in warheads, nuclear reactors, produced by neutron activation or generated by particle beams or directed energy weapons. The detector has high sensitivity, low background, and a wide field-of-view for simultaneous scan of large parts of the sky without a collimator, coded aperture or pointing requirement. The detector also has excellent angular resolution for accurate direction measurement and imaging; good energy resolution for the identification of the source material by its energy spectrum; and low power consumption for possible long calibration and test operations in a space environment.

The silicon advanced Compton recoil electron detector (SACRED) uses the Compton double scatter technique with recoil electron tracking to detect medium energy gamma rays. The detector is optimized for medium energy gamma rays from 0.3 to 30 MeV.

The Compton double scatter technique involves two detector layers; the silicon microstrip hodoscope and the calorimeter. The incoming photon Compton scatters in the hodoscope. The second scatter layer is the calorimeter where the scattered gamma ray is totally absorbed. The recoil electron in the hodoscope is tracked through several detector planes until it stops. The x and y position signals from the first two planes of the electron track determine the direction of the recoil electron. The energy loss from all planes are added to determine the energy of the recoil electron.

The hodoscope of the proposed detector is based on double sided silicon microstrip detectors with 1 mm strip spacing and 200 micron thickness, where the interaction point of the recoil electron in each silicon plane is determined to 1 mm×1 mm. The silicon microstrip detectors are versatile, the pixel size can be selected from 25 micron×25 micron to 1 cm×1 cm. The 1 $mm^2$ pixel size is preferable.

The measurement of the direction of the Compton recoil electron track reduces the incident gamma ray event ring to an event arc. The recoil electron direction calculation requires only the x and y coordinates of the first two adjacent planes along the track of the recoil electron. For the measurement of the direction of motion of the recoil electron (moving forward or backward in the hodoscope) a track which penetrates $\geq 2$ adjacent planes is required. If the energy of a recoil electron is low enough it may be absorbed in the same detector plane and not produce a track. For the preferable 200 micron detector thickness the recoil electron tracking is effective for electrons >0.25 MeV energy which means that incident gamma rays with energies >1 MeV will produce recoil electron tracks with high probability. For low energy gamma rays which do not produce recoil electron tracks the imaging is carried out using event rings instead of arcs. This reduces the sensitivity somewhat for low energy gamma rays approaching 0.3 MeV because the background increases. If thinner silicon strip detectors are used the recoil electron tracking threshold can be reduced to even lower energies. The 200 micron thickness was found by Monte Carlo studies to be optimum and the most cost effective design for the proposed detector with a wide energy range. For example, if a detector is required only for low energies of 0.3 to 3 MeV, the optimized design would use thinner silicon microstrip detectors with a lower total thickness.

The second scatterer will be thallium activated cesium iodide (CsI(Tl)) detectors viewed by photodiodes. This is a cost effective approach. If higher energy resolution is required, a germanium array calorimeter could be used instead of the CsI(Tl) crystals. This is a costlier alternative that requires refrigeration to liquid nitrogen temperatures.

The Nondestructive Advanced Detector for Inspection Application (NADIA) for realtime inspection of munition items uses the Compton double scatter technique with recoil electron tracking to detect x-rays from 300 to 2,000 keV. The higher energy x-rays are used for the NDI of dense objects or large munition items such as large shells.

Compton double scatter involves two detector layers, the silicon microstrip hodoscope and the calorimeter. The incoming photon Compton scatters in the hodoscope. The second scatter layer is the calorimeter where the scattered gamma ray is totally absorbed. The recoil electron in the hodoscope is either stopped in the first scatter plane (for low energy recoil electrons) or tracked through several detector planes until it stops. The x and y position signals from the first two planes of the electron track determine the direction of the recoil electron. The energy loss from all planes are added to determine the energy of the recoil electron. The hodoscope of the proposed detector is based on double sided silicon microstrip detectors with 0.5 to 1 mm strip spacing and 300 to 1,000 micron thickness, where the interaction point of the recoil electron in each silicon plane is determined with pixel size of $0.5\times0.5$ mm$^2$ to $1\times1$ mm$^2$, respectively. The silicon microstrip detectors are versatile, the pixel size can be selected from 25 micron$\times$25 micron to 1 cm$\times$1 cm.

The second scatterer (calorimeter) will be thallium activated cesium iodide (CsI(Tl)) detectors viewed by photodiodes. Although other detectors may be used, this is the preferable approach. If higher energy resolution is required, a hodoscope only detector with large number of silicon detector planes or a germanium array calorimeter could be used instead of the CsI(Tl) crystals. These are costlier alternatives and require refrigeration to liquid nitrogen temperatures for the germanium. However, energy resolutions $\leq 1\%$ may be achieved with dramatic reduction in the scattered photon background.

The new detector design, described above, includes a calorimeter surrounding the sides of the silicon microstrip hodoscope. The proposed prototype NADIA detector also is expected to have low sensitivity to neutrons as the silicon microstrip detectors in the hodoscope do not contain hydrogen. Therefore, the proposed detector can work effectively in high neutron background levels.

The present invention provides a high sensitivity, high spatial resolution and electronically collimated commercial single photon emission computed tomography (SPECT) system (COMSPECT). It will be sensitive from 81 keV to 511 keV $\gamma$-ray photons. Both the direction and energy of the incident $\gamma$-ray photons will be measured with high resolution. The method of determination of the photon direction eliminates the need for a mechanical collimator and the energy measurement discriminates against the scattered photon background. The double Compton scatter technique is applied to medical imaging.

The claimed COMSPECT system is constructed from newly developed position sensitive double sided silicon strips (for strip pitch~1 mm) or silicon microstrip (for strip pitch <<1 mm) detectors. The silicon strip detectors with strip pitch of about 1 mm are preferable for the intended application. These detectors can produce the x and y coordinates of a photon interaction in a single wafer with thicknesses varying from 150 microns to about 2 mm. One embodiment of the COMSPECT system will use many planes of double sided silicon strip detectors with about 1 mm pixel size and 0.5 to 1 mm thickness. The planes will be separated by 0.5 to 1.5 cm distance depending on the combination of the optimum pixel size and the required angular resolution. Smallest possible separation is always preferred to keep the depth of the detector small without sacrificing spatial resolution. The incident $\gamma$-ray Compton scatters in one of the detector planes, the dominant process for photons with $\geq 50$ keV energies in silicon strip detectors. The energy of the scattered electron in this detector plane is measured. The scattered $\gamma$-ray with reduced energy can be absorbed in the calorimeter or in an another detector plane through the photoelectric effect. The energies of these second interactions are also measured. If the scattered $\gamma$-ray photon is completely absorbed the sum of the two energies gives the energy of the incident photon and the individual energies and direction of the scattered photon give the scatter angle of the incident $\gamma$-ray. Thus, the gamma rays emitted from a radionuclide can be imaged without need for a collimator.

The scattered $\gamma$-ray photons can make a second Compton scatter and then escape without further interaction. Also the photons already scattered inside the patient will deposit lower total energy. These events will produce a tail at lower energies in the energy spectrum. Such events can be discriminated effectively because the total energy detected is smaller than the known incident $\gamma$-ray energy. However, a high sensitivity mode may be applied with reduced angular resolution by adding the missing energy to the energy measured at the second scatter. This will dramatically increase the sensitivity but reduce angular resolution somewhat and will not allow the discrimination of the scattered photon background.

A calorimeter surrounding the silicon strip detector hodoscope absorbs the Compton scattered photons. The calorimeter can be fabricated from a few mm thick plane of silicon, CdZnTe strip detectors or CsI(Tl) crystals viewed by a photodiode. The calorimeter can be used as a second scatterer and/or a missing energy detector.

The double Compton scatter measurement determines the direction of the incident $\gamma$-ray to a cone with half angle equal to the scatter angle. This type of measurement is new in the nuclear medicine and requires special data analysis software. The data analysis can be carried out by cone interaction, Maximum Likelihood or Maximum Entropy techniques. These are iterative techniques and require long computation times. A new direct data analysis and imaging technique, Direct Linear Algebraic Deconvolution (DLAD) method, may be applied for real time imaging.

A new high sensitivity three-dimensional scintimammography system (ScintiMAM) is provided. The system is based on the higher malignant tissue uptake of Tc-99m SestaMIBI and/or Tl-201 chloride compared to benign masses (except for some highly cellular adenomas). Therefore, these radiopharmaceuticals can be used to help diagnose and differentiate breast tumors from benign growths. In clinical trials, the Tc-99m SestaMIBI has been found to be superior to Tl-201. Possible mechanisms for uptake of Tl-201 chloride into tumor cells include the action of the ATPase sodium-potassium transport system in the cell membrane which creates an intracellular concentration of potassium greater than the concentration in the extracellular space. Thallium is thought to be influenced significantly by this system in tumors. In addition, a co-transport system has been identified which also is felt to be important in uptake of thallium by tumor cells. The mechanism of Tc-99m SestaMIBI accumulation in tumors is not clear but appears to be related to a 170 kDa P-glycoprotein which is a plasma membrane transport protein.

The ScintiMAM system is a new approach to gamma ray imaging. It uses the Compton double scatter technique to determine the direction of the incident photon directly. This eliminates the requirement for a collimator and significantly increases the detection efficiency.

The Compton scatter PET (ComPET) system provided by the present invention can be designed as a cylindrical detector with substantial length, about 30 cm or longer. Cylindrical geometry will lead to the production of accurate 3-dimensional images. Another embodiment of the ComPET system is a ring detector with a $\leq 7$ cm width similar to multi-slice ring type PET systems presently available. The ComPET system is designed to have a maximum of 2$\times$2 mm² spatial resolution. A common technique to reduce the radial elongation error is building a detector with large internal diameter to use longer crystals without loosing spatial resolution. For example, HEADTOME-IV, a whole body PET, has 4 detector rings with a 566 mm inner diameter, each consisting of 768 BGO crystals of 3×18×24 mm³ (width×height×length). The thickness of each slice is 18 mm. New methods have been developed to lower the radial elongation of the point spread function (PSF) by measuring the depth of the interaction in the BGO crystal. The ComPET system has no radial elongation error because the active detector voxel size is 6 mm³ with about 1.5 mm length compared to 1,296 mm³ with 24 mm length for HEADTOME-IV. The reduced scattered photon background, low random coincidence rate, and lack of the radial elongation error may allow a significant reduction in the internal ring diameter which reduces the size and weight of the ComPET system and increases effective detector aperture.

The photon attenuation inside the patient can be corrected using the techniques already developed. For example, the boundary method has already been successfully applied to attenuation correction in PET image reconstruction. In this method, the organ boundaries are determined by transmission tomography, each region is enclosed by a boundary and assigned an average attenuation coefficient for that region. Attenuation correction factors for all angular views can be calculated from the quantized image. This method can be directly applied to the ComPET system. The high spatial resolution without radial elongation of the detector is improves the accuracy of the attenuation correction because the boundary of the organs can be determined with higher precision. Also smaller organs may be identified and corrected for attenuation independently from the larger organs.

The ComPET system does not use PMTs and supporting electronics which contribute largely to the bulkiness of current PET system. Consequently, the gantry needs less stringent structural requirements and will be easier and less costly to manufacture. A longer cylindrical full body detector can also be employed by placing several rings of 6 cm width side by side. This will provide true 3-dimensional imaging since the slice thicknesses will be ≦2 mm without septa and voxel size 2×2×2 mm³ uniform throughout the organ of the patient under study. (Septa at two sides of the active area of the detector will be used to lower background radiation from organs not imaged.) Having no radial elongation may make it possible to bring the front detector surface as close as possible to the patient. It increases overall detector sensitivity while still maintaining manageable count rate per each pixel. This also decreases the photon noncollinearity error.

The ComPET system preferably uses thin film strip detectors with high stopping power. The Cadmium Zinc Telluride (CdZnTe) detectors developed by the Aurora Technologies Corporation (ATC) for gamma ray application are presently the best choice for these detectors.

The ComPET system is constructed from newly developed position sensitive double sided CdZnTe strip detectors. The CdZnTe strip detectors can have ≧0.1 mm strip sizes both in the x and y dimensions on a single wafer with thickness varying from 250 mm to 2 mm. The ComPET system uses several planes of double sided CdZnTe strip detectors with approximately 2×2 mm² pixel size on an 1.5 mm thick wafer. The planes will be packed in near touching distance to detect a collinear photon pair. The incident photons undergo Compton scatter in one of the detector planes, which is the dominant process for photons above ≈200 keV in CdZnTe. The energy of the Compton recoil electron in this detector wafer is measured. This process is repeated till the scattered photon with reduced energy gets absorbed through the photoelectric effect in another detector plane or the scattered photons can escape without further interactions. If the scattered photon is fully absorbed the sum of the measured energiegives the total energy of the incident photon. The straight line (cord) joining the first interaction points of an annihilation photon pair at the CdZnTe strip detector in coincidence will determine the geometry. Escaped photons will produce a tail at lower energies in the energy spectrum. Such events can be rejected because the measured total energy is smaller than the expected energy of the known incident energy of 511 keV.

The proposed technique is new in nuclear medicine and requires special data analysis software. The raw data analysis for this application is much simpler than the normal Compton double scatter data analysis because the incoming photon direction is already determined from coincident observation of two interaction points. Backprojection and forward-projection (Radon transform), algebraic reconstruction technique (ART), Maximum Likelihood (ML) or Maximum Entropy (ME) methods can be used to form the PET images from the analyzed raw Compton double scatter data. The later techniques, ART, ML and ME, can be combined with the general methods such as the back-projection methods to improve PET imaging. These are, however, iterative techniques and require long computation times. A new data analysis and imaging technique, Direct Linear Algebraic Deconvolution (DLAD), has excellent potential for real time imaging and may be applied to PET. The new DLAD method is not an iterative process and is expected to lead to fast data analysis in real time with immediate visual output.

A further understanding of the nature and advantages of the present invention may be realized by reference to the remaining portions of the specification and the drawings.

BRIEF DESCRIPTION OF THE DRAWINGS

FIG. 5 is a table listing the physical properties of some high density radiation detectors that can be used as the calorimeter in the SACRED detector;

FIG. 48 is the surface image obtained for three 0.5 cm diameter 141 keV sources placed 10 cm above the top silicon strip detector plane by integrating the overlapped area of the event rings into the corresponding image pixels;

FIG. 49 is the density plot obtained for three 0.5 cm diameter 141 keV sources placed 10 cm above the top silicon strip detector plane by integrating the overlapped area of the event rings into the corresponding image pixels;

FIG. 50 is the surface image of the same data as illustrated in FIG. 48 using the DLAD technique of data analysis;

FIG. 51 is the density plot of the same data as illustrated in FIG. 49 using the DLAD technique of data analysis;

FIG. 52 is a table of some of the gamma ray sources used as radiotracers in scintimammography;

FIG. 62 is a table of some positron sources used as radiotracers in PET;

FIG. 66 is an illustration of the top view for the module shown in FIG. 65;

FIG. 67 is an illustration of a doublesided CdZnTe strip detector;

FIG. 68 is a table with the characteristics of HPB grown $Cd_{1-x}Zn_xTe$ crystals;

DESCRIPTION OF THE PREFERRED EMBODIMENT

Silicon Advanced Compton Recoil Electron Detector (SACRED)

The most probable interaction mechanism for 0.3 to 30 MeV gamma rays is the Compton scatter process. Therefore, the detection of gamma rays in this energy range must use Compton interaction to have maximum sensitivity. The detector must also have excellent angular and energy resolution and a wide field-of-view. The best detection technique that has all these features is the Compton double scatter method. This technique incorporates Compton scattering, photoelectric absorption and pair production. The three gamma ray interaction mechanisms are briefly discussed below.

Figure 1:
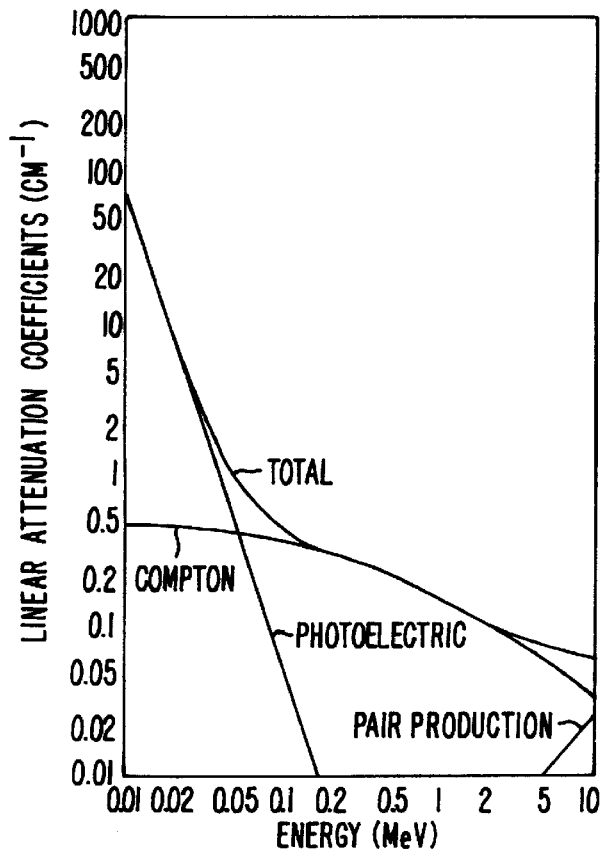
FIG. 1 is an illustration of gamma ray linear attenuation coefficients for silicon microstrip detectors for photoelectric absorption, Compton scattering, and pair production.

Although a number of possible interaction mechanisms are known to gamma rays in matter, only three major types play an important role in radiation detection: photoelectric absorption, Compton scattering, and pair production. All these processes lead to the partial or complete transfer of the photon energy to electron energy. They result in sudden and abrupt changes in the photon history where the photon disappears entirely or is scattered through a significant angle. FIG. 1 shows gamma ray linear attenuation coefficients for silicon microstrip detectors for these three processes. The photoelectric absorption dominates below 0.05 MeV for silicon. Compton scattering becomes important above 0.05 MeV and it stays the dominant process up to about 15 MeV, where pair production takes over. The important detection process for silicon microstrip detectors is Compton scattering for energies from 0.3 to 15 MeV. The Compton interaction will take place in the silicon hodoscope. The subsequent absorption of the scattered photon at the calorimeter is mainly through the photoelectric effect with possible Compton scattering prior to photoelectric absorption.

In the photoelectric absorption process, a photon undergoes an interaction with an absorber atom in which the photon completely disappears. In its place, an energetic photoelectron is ejected by the atom from one of its bound shells. The interaction is with the atom as a whole and can not take place with free electrons. The photoelectron appears with an energy $E_e$ given by $$E_e = h\nu - E_b$$

where h$\nu$ is the incident photon energy and $E_b$ represents the binding energy of the photoelectron in its original shell. For gamma ray energies, h$\sigma$, of more than a 0.05 MeV, the photoelectron carries off most of the original photon energy. For silicon microstrip detectors this process is important for low energy gamma rays only, 0.005 to 0.05 MeV. For CsI(Tl) crystals the photoelectric effect is dominant up to 0.3 MeV above which Compton scattering becomes important. Photoelectric absorption falls nearly exponentially with an increase in energy. Photoelectric absorption is excellent for the determination of the scattered photon energy as the photon is completely absorbed.

Compton scattering takes place between the incident gamma ray and an electron in the absorbing material. In Compton scattering, the incident gamma ray is deflected through an angle θ with respect to its original direction. The photon transfers a portion of its energy to the recoil electron initially at rest. Because all angles of scattering are possible, the energy transferred to the electron can vary from zero to a large fraction of the gamma ray energy. This has been a problem in the detection of gamma rays at energies dominated by the Compton scatter process, since the detected recoil electron alone does not give sufficient information to determine the energy and direction of the incident photon uniquely. This has been solved by the Compton double scatter technique described below.

For a gamma ray with energy larger than or equal to twice the rest mass of an electron, $\geq 2$ mc$^2$ (1.022 MeV), pair production becomes energetically possible. The probability of occurrence remains very low until the gamma ray approaches several MeV; therefore, pair production is confined to high energy gamma rays. The interaction takes place in the coulomb field of a nucleus. In the interaction a gamma ray photon disappears and is replaced by an electron-positron pair. All excess energy carried by the photon above 1.022 MeV, the energy required to create the pair, goes into kinetic energy shared by the electron and the positron. The positron annihilates with an electron after slowing down in the absorbing medium and produces two annihilation photons each with energy of 0.511 MeV in the para state or 3 photons with different energies adding to 1.022 MeV in the ortho state. The para state decay to 2 photons (99.7%) dominates ortho state decay.

For silicon microstrip detectors, pair production becomes significant for gamma rays above 10 MeV and dominates Compton scattering above 15 MeV. Pair events are easily distinguishable as they produce two tracks starting from a common vertex. Multiple scattering in the silicon planes quickly separate the two tracks which resemble an inverted V. Both the electron and the positron loose their energy in the silicon planes and stop. The positron quickly annihilates with an electron as it stops and creates back-to-back 0.511 MeV gamma rays. One or more of the annihilation gamma rays will likely be detected in the calorimeter in coincidence with the electron-positron pair observed in the silicon microstrip hodoscope. The detection of the pair produced events keeps the sensitivity of the proposed detector constant above 10 MeV and does not decline as is the case if only Compton scatters are detected.

Gamma Ray Detectors

Gamma ray cameras are designed for low energy photons up to about 1 MeV. They use the photoelectric absorption as the detection mechanism. This process does not produce information on the direction of the incident photon, therefore, lead or tungsten honeycomb collimators are used to determine the direction of the incoming photon. Collimators limit the field-of-view of the detector to small solid angles. The instrument would then require pointing and cannot image several sources separated by larger than few degrees simultaneously. To detect a weak signal the detector must also shift between the source and a designated background direction at regular intervals if there is significant diffuse background. The time lost in measuring the background can be gained by using a separate identical detector and have the two detectors switch directions measuring the source and the background at regular intervals. The weak signal is observed when there is a significant excess in the direction of the source after the background rates are subtracted. This method applies well to astrophysical observations but its application for the detection of nuclear warheads in space will be limited. An example of such a detector is the OSSE detector flown on Compton Gamma Ray Observatory.

A variation of this type of detector is to use several large area detectors without collimators facing different directions. In this case the direction of the point source is determined by the ratio of count rates at different detectors. An example of such a detector is the BATSE detector on the Compton Gamma Ray Observatory. The background and source are detected simultaneously. The direction measurements are hampered by different backgrounds for different detectors since they view different parts of the sky and also due to scattering of the signal from Earth's atmosphere which alters the background levels. The error on the direction measurement can be as large as 10° and it will be difficult to correct as the gamma ray background varies with time.

The coded aperture method has been used for imaging and spectroscopy of low and medium energy gamma rays. The single advantage of the coded aperture method over the usual on-source/off-source method with single-scatter detectors with relatively large fields-of-view is its improved angular resolution through imaging. That is the source counts (S) using one-half the sensitive detector area can be compressed statistically into one "sky element" (aperture opening). But the background count level (B) in this sky element is that of the entire position sensitive detector. Thus, the coded aperture does not enhance the sensitivity above that of the same detector without a mask. Also the presence of the mask reduces the area by a factor of 2 and the sensitivity by $\sqrt{2}$. Coded aperture instruments have been most successful at imaging sources in hard x-rays up to about 0.3 MeV region where S/B>>1%. Above 0.3 MeV, the sensitivities of coded aperture instruments deteriorate rapidly as source fluxes, instrument efficiencies and backgrounds, all decrease with energy but the signal-to-noise ratio ($=S/\sqrt{B}$) decreases faster. As a result, high quality imaging and good angular and energy resolution with the coded aperture technique have been restricted to energies below about 0.5 MeV.

In a single Compton scatter the detected recoil electron alone does not give sufficient information to determine the energy and direction of the incident photon. This problem has been solved by the Compton double scattering technique illustrated in FIG. 2. The total incident gamma ray energy $E_\gamma$ and Compton scatter angle $\theta$ for the double scatter process are given by $$E_\gamma = E_{e1} + E_{\gamma 1}$$

and $$\cos\theta = 1 - mc^2(1/E_{\gamma 1} - 1/E_\gamma)$$

where the $E_{e1}$ is the energy of the recoil electron at the first scatter, $E_{\gamma 1}$ is the energy of the scattered gamma ray and $mc^2$ is the rest energy of an electron. The time-of-flight (TOF) measurement of the gamma rays at the first and last scatters has been used effectively to discriminate against upward moving background gamma ray events. Upward moving backgrounds can dominate in certain circumstances such as detectors flown on balloons at about 130,000 feet due to gamma rays generated in the atmosphere. Over the past 20 years this method has been applied to both the detection of gamma rays (1 to 30 MeV) and high energy neutrons (2 to 100 MeV) with balloon-borne detectors. It was successful in detecting nuclear powered Soviet satellites, atmospheric gamma rays and neutrons and a wide range of celestial objects. The COMPTEL detector on the Compton Gamma Ray Observatory is another example for this type of detectors.

Figure 2:
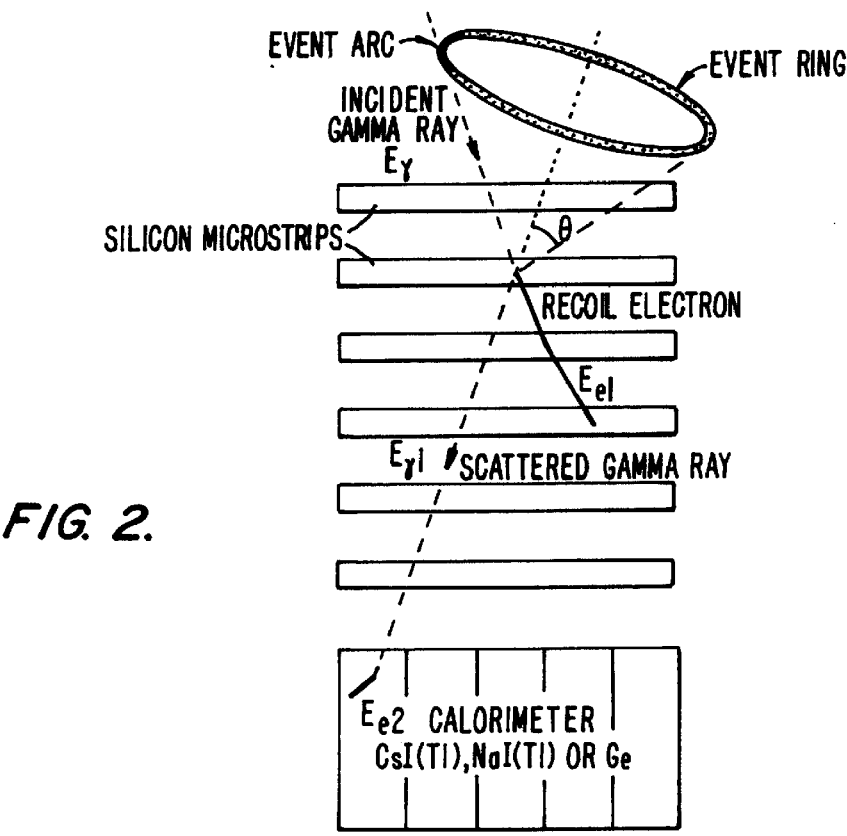
FIG. 2 is an illustration of the Compton double scatter technique for detecting gamma rays.

In a preliminary detector the incident gamma ray first scatters by the Compton process in one of the silicon microstrip detectors, losing electron recoil energy $E_{e1}$. If the recoil electron has sufficient energy it will penetrate several silicon microstrip planes and be deflected in each detector plane due to multiple scattering as illustrated in FIG. 2. The scattered photon is absorbed in the calorimeter. If the second interaction is photoelectric absorption the full energy of the scattered photon is measured ($E_{e1} = E_{e2}$) and the energy of the incident photon and the scatter angle is determined. This is the dominant process as photoelectric absorption increases rapidly with decrease in the scattered photon energy and increase with the atomic number Z of the calorimeter. Another possibility is that the second interaction can be another Compton scatter in a silicon microstrip hodoscope and the escaping photon is absorbed in the calorimeter. Such events are legitimate and the subsequent scatters can be recognized by the proposed prototype detector. To apply the Compton double scatter formula given above the sum of all the energy measured after the second scatter is added to the energy of the second scatter, $E_{e2}$. Since the calorimeter is a high-Z high density scintillator, the scattered photon, with high probability, is fully absorbed.

The incident gamma ray direction lies on a cone segment in the field-of-view with half-angle $\theta$. The cone axis is determined by the interaction positions in the first and the second scatters. Therefore, each detected gamma ray gives a ring in the field-of-view with thickness equal to the full width at half maximum (FWHM) of the scatter angle resolution which depends on the geometry of the pixel sizes at the first and second scatters and their energy resolution. The intersection of event rings images a discrete source on a two-dimensional "sky-map". This is true for the case where the direction of the recoil electron in the first scatter is not measured. If the recoil electron traverses $\geq 2$ adjacent silicon microstrip detector planes, its direction is measured by the electron track in the first and second planes the electron traverses and the event ring is reduced to an event arc as shown in FIG. 2. The thickness of the event arc is the same as the event ring and the length of the arc is determined by the FWHM multiple scatter angle at the first scatter. The time-of-flight measurement used to discriminate against upward moving background gamma ray events is replaced by a new technique which uses the scatter angle and energy deposition along the recoil electron track. The reduction of the event ring into an event arc dramatically reduces background and increases the signal-to-noise ratio. Elimination of the time-of-flight measurement allows significant reduction in the detector size without decreasing the sensitivity.

Pair production detectors use thin high Z converter planes interleaved with position sensitive detectors such as wire spark chambers followed by a calorimeter to absorb the escaping high energy electron-positron pairs. These detectors are sensitive to gamma rays above about 20 MeV. They can go up to 30 GeV in energy. Because the gamma ray is totally converted into an electron-positron pair the energy of the incident photon is determined. Photon energies above 20 MeV give most of their energy to the electron-positron pair and the direction of the incident photon is preserved in the velocity of the created particles due to conservation of momentum. Therefore, the direction of the incident photon is also determined. An example of such a detector is the EGRET detector on the Compton Gamma Ray Observatory.

The proposed prototype SACRED detector is designed to be sensitive to pair production events as well as Compton double scattered events. The pair produced events are recognized by their unique properties and treated separately. The inclusion of the pair produced events improves the sensitivity of the proposed prototype detector above 5 MeV.

Silicon Microstrip Detectors

The proposed prototype detector employs silicon microstrip detectors developed recently as the first scatterer (hodoscope). Silicon microstrip detectors have large active areas, excellent energy and position resolution and fast readout. Three inch diameter wafers, typically 200 to 500 microns thick with parallel readout strip of $\geq 25$ micron pitch on one side, have been available for few years. Pitch size can have any value from 25 micron to several cm.

On the average 1 electron-hole pair is produced per 3.6 eV energy deposited. The most probable energy loss for singly charged minimum ionizing particles in thin silicon detectors is 26 keV/100 micron which produce about 22,000 electrons (and holes) in 300 micron silicon which can be collected in <10 ns. Spatial resolutions of <10 microns in one dimension are obtainable by exploiting charge division between adjacent strips. The energy loss of minimum ionizing particles in a single detector is represented by a Landau distribution with 40% FWHM for 300 microns. Superimposed on the signal is Gaussian-distributed noise related to detector strip and preamplifier input capacitances. This noise or "equivalent noise charge" (ENC) can be typically 1,000 electrons. Thus, large signal-to-noise ratios (~22) are obtainable for minimum ionizing particles. Silicon detectors are not easily damaged by radiation and they can tolerate integrated charged particle fluxes of up to $10^{10}$ to $10^{14}/cm^2$ and still operate as efficient detectors.

Single sided silicon microstrip detectors are made with the junction side of a standard p+n diode segmented into many strips with a wide range of widths and pitch. The ohmic side is a single plane. These detectors are mainly used in high energy physics experiments to detect minimum ionizing high energy charged particles that go through all the silicon planes without appreciable energy loss. The Compton converter hodoscope in the proposed detector is new and somewhat different in that the recoil electron loses varying fractions of its energy at each detector wafer it traverses before it completely stops.

Figure 3:
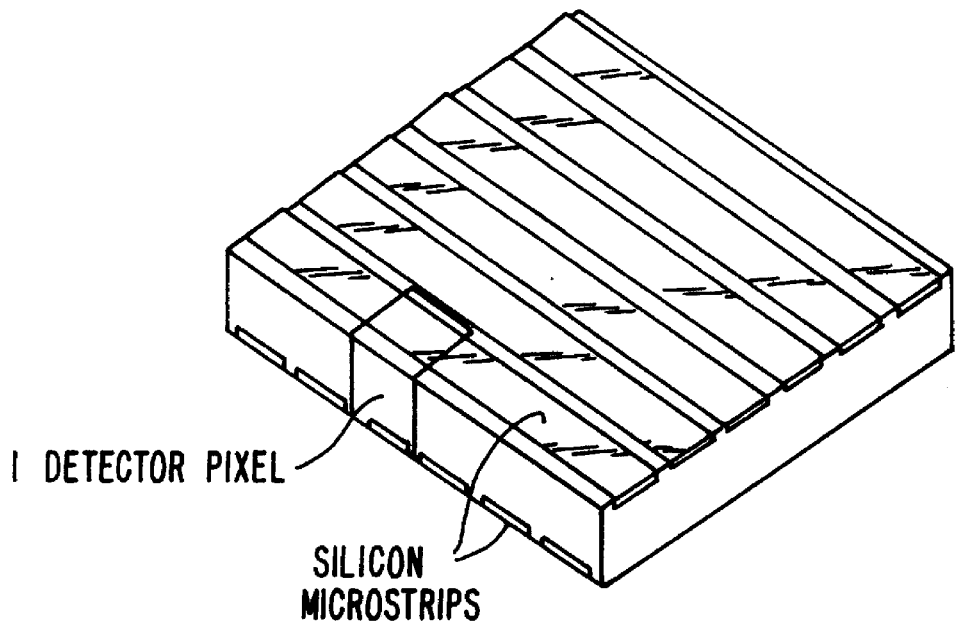
FIG. 3 is an illustration of a typical double sided silicon microstrip or strip detector.
Figure 4:
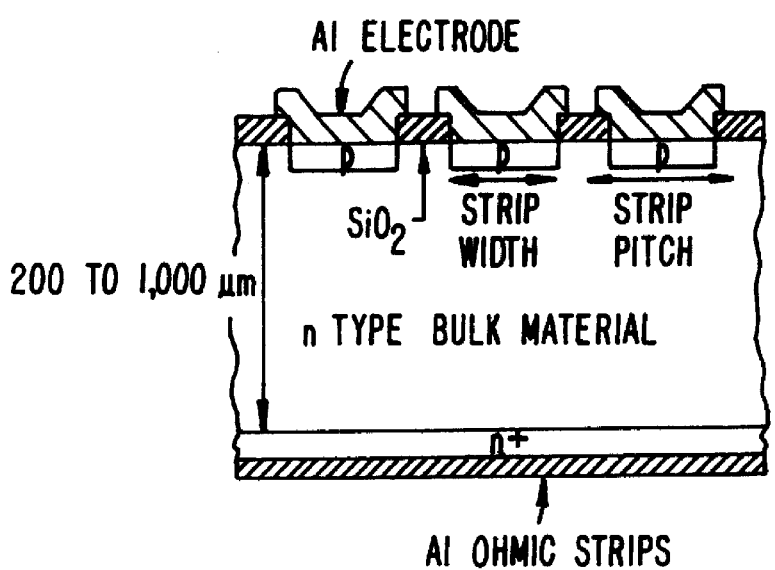
FIG. 4 is the schematic cross section of the detector illustrated in FIG. 3.

More recently, double sided readout silicon microstrip detectors with orthogonal strips on opposite sides have been developed. FIGS. 3–4 show the basic features of a double sided silicon microstrip or strip detector. The distinct advantage here is that both x and y coordinates of a traversing particle are determined in a single detector plane. For double sided detectors, both the junction and the ohmic sides of the silicon wafer are segmented with orthogonal strips to provide simultaneous readout of the particle impact point. Position resolutions well below 1 mm$^2$ on both sides can be achieved. The proposed prototype detector will use 200 to 300 micron thick double sided silicon microstrip detectors with about 1 mm spaced strips orthogonal on the top and bottom surfaces with about 6×6 cm area. Such detectors are now commercially available and fit well with the proposed design. The x and y position of the first two interaction points on the recoil electron track determines the electron direction. A summation of all interactions gives the energy of the recoil electron. It is anticpated that 14×14 cm$^2$ detectors from 6 inch diameter wafers will be available in the near future. Already, 9.4 cm diameter detectors have been fabricated from 4 inch diameter wafers. Bridged detectors with overall lengths exceeding 25 cm have been developed. Bridging allows one preamplifier to be connected to a series of strips on adjacent detectors with significant savings in electronics.

The energy resolution for silicon microstrip detectors are excellent because of the large number of electron-hole (e-hole) pairs created in silicon. For 0.5 MeV recoil electrons stopping in silicon, about 139,000 e-hole pairs (278 e/keV) are produced. The inherent energy resolution, $R_f$, is 0.6% if the recoil electron stops in one silicon wafer by assuming a Poisson process. The $R_f$ is calculated by $$R_f = FWHM/E_0 = 2.35/\sqrt{N}$$

where N is the number of e-hole pairs created. The Fano factor F (F=Observed variance/Poisson predicted variance) corrects for the departure of the observed statistical fluctuations in the number of charge carriers from pure Poisson statistics. This factor has to be determined experimentally when the prototype detector is built.

The limiting resolution, $R_L$, is determined by the number of 200 micron detectors the stopping electron traverses since the noise of each detector adds in quadrature. The formula for the limiting energy resolution now becomes $$R_L = (2.35\sigma/N)\sqrt{N_D}$$

where $\sigma$ is the noise fluctuation (ENC) and $N_D$ is the number of detectors traversed by the recoil electron. As an example, scattered 0.5 MeV electrons should traverse at most 3 detectors before stopping to give a FWHM energy resolution of 2.9% by assuming that the ENC is 1,000 electrons. For 5 MeV electrons, about 53 detector strips would contribute to the noise to give a 1.2% FWHM energy resolution. These Compton converter resolutions are dramatic improvements over organic scintillators (e.g. BC-523, 17% at 0.5 MeV). Increasing the thickness of the individual detectors improves the energy resolution but decreases the accuracy of the recoil electron direction determination because of the increase in the multiple scattering at the first interaction plane. The optimum thickness also depends on the energy range of the detector.

The FWHM angular resolution of the scatter angle in Compton double scatter detector depends on the geometry and the energy resolution. The FWHM uncertainty in the arc or cone half-angle, $\Delta\theta$, due to a detector of finite energy resolution, $\Delta E_{e1}$ and $\Delta E_{e2}$, at the hodoscope and the calorimeter can be calculated from the Compton scatter formula given above to be $$\Delta\theta = \{mc^2/(E_\gamma^2 \sin\theta)\}\{\Delta E_{e1}^2 + [(E_\gamma^2/E_{\gamma 1}^2)-1]^2 \Delta E_{e2}^2\}^{1/2}$$

where $mc^2$ is the electron rest energy (0.511 MeV), $\theta$ is the Compton scatter angle, and $E_\gamma$ and $E_{\gamma 1}$ are the incident and scattered photon energies, respectively.

For example, if the energy resolution for 0.5 and 5 MeV recoil electrons are used as calculated above and the Compton scattered gamma rays have incident energies of 1 and 10 MeV then Compton scatter angles can be calculated to be 33.9° and 18.4°. When these parameters are put into the above formula the angular resolution, $\Delta\theta$, can be calculated as 2.2° and 0.1° by assuming 7% and 4% energy resolutions for 0.5 and 5 MeV Compton scattered gamma rays in the CsI(Tl) calorimeter, respectively. The angular resolution improves significantly with an increase in the energy of the incident and Compton scattered photon. The position of a point source (the peak of the distribution) can be determined with an accuracy much higher than the angular resolution, a fraction of a degree for 1 MeV gamma rays, with sufficient statistics.

The geometric angular resolution, $\Delta\theta_{Geom}$, is the FWHM variation on the axis of the image cone and depends on the finite geometric pixel size of the silicon microstrip detectors (1 mm²) and the calorimeter (1 cm²), and the distance between the first and second interaction points. Normally the geometric angular resolution is kept smaller than the scatter angle variation, which depends strongly on the energy resolution as shown above. If the average distance between the two interaction points is 50 cm then the geometric angular resolution is about 1.2°. Such good geometric angular resolution complements the fine Compton scatter angle resolution. If the limiting pixel size, (1 cm2), at the calorimeter can be improved using a CsI(Tl) camera technique then the geometric angular resolution can be improved further.

Another important advantage of silicon microstrip detectors is that they do not need high voltages or cooling to low temperatures. Room temperature functionality is important to produce small size, low cost and low power detectors. They also have a strong potential for mass production. However, significant number of wafers are needed to achieve conversion rates required for high sensitivity. Their small thicknesses and ultrasonic wire bonding capability render them good candidates for compact PC mounting with data acquisition IC's placed next to them. The readout IC's can be designed to give fast trigger outputs when events occur and output the address and the analog content of the channel that have data.

Calorimeter

A calorimeter is placed around and at the bottom of the silicon microstrip detectors in the new detector design to absorb the escaping Compton scattered photons. FIG. 5 is a table listing the physical properties of possible high density radiation detectors for the calorimeter. Among these HPGe, BGO, $CdWO_4$ and CsF are higher cost detectors especially HPGe, which also needs cooling to liquid nitrogen temperatures.

Sodium Iodide is the most popular high density scintillator. Robert Hofstadter (1948) first demonstrated that crystalline sodium iodide, in which a trace of thallium iodide had been added in the melt, produced an exceptionally large scintillation light output compared with the organic materials that had been used before. This discovery, more than any other single event, ushered in the era of modern scintillation spectrometry of gamma radiation. It has a large light yield (FIG. 5) and its response to electrons (and gamma rays) is close to linear over most of the significant energy range. The NaI(Tl) crystal is fragile and hygroscopic. It has to be handled carefully and hermetically sealed. It has long decay time and is not suitable for fast timing applications.

Cesium Iodide is another alkali halide that has gained substantial popularity as a scintillator material. It is commercially available with either thallium or sodium as the activator material and has significantly different scintillation properties with thallium. CsI has a larger gamma ray absorption coefficient per unit size and is less brittle than NaI. The two forms of CsI scintillators, CsI(Na) and CsI(Tl), are discussed separately below with emphasis on the CsI(Tl) detector.

CsI(Na) has an emission spectrum similar to NaI(Tl). Its light yield is also comparable. CsI(Na) is hygroscopic and must be hermetically sealed. Therefore, CsI(Na) is similar to NaI(Tl) and has the same draw backs. CsI(Tl) is different than NaI(Tl) and has unique properties. It is also slightly hygroscopic. Energy resolution of 5% FWHM at 0.662 MeV have been obtained with 2.5 cm diameter×2.5 cm thick CsI(Tl) scintillation crystals coupled to large area (2.5 cm diameter) mercuric iodide photodetectors. This is about 50% better than the NaI(Tl) detectors. The mercuric iodide photodiodes are not yet available as commercial devices. Resolution of 6% at 0.662 MeV has been obtained for considerably smaller CsI(Tl) crystals using avalanche photodiodes. Large area P-I-N diodes coupled to 1 cm×2 cm CsI(Tl) give 7% resolution at 0.662 MeV. These crystals produce 35% more photons per MeV than NaI(Tl) and their light spectrum is much better matched to the sensitivities of the photodiodes. A key to improved energy resolution is good light collection by matching the areas of the crystals to those of the photodiodes.

An important property of CsI(Tl) is its variable decay time for different particles. Therefore, pulse shape discrimination techniques can be used to differentiate among various types of radiation such as electrons, protons and alpha particles. The CsI(Tl) light output is quoted lower than NaI(Tl) for bialkali photomultiplier tubes (PMTs) (FIG. 5).

The scintillation yield is actually found to be larger than that of any other scintillator because its light emission peaks at longer wavelengths. It can be used with photodiodes with extended response in the red region of the spectrum. Its energy resolution is equal or better to the energy resolution of the NaI(Tl) crystals. The CsI(Tl) has strong potential for application as the calorimeter in the proposed detector.

CdTe, CdZnTe, HPGe and $HgI_2$ are solid state detectors and can be made in arrays for position sensitive applications. They are high Z and high density crystals. They are used to detect x-rays and gamma rays directly without need for photomultiplier tubes or p-i-n and avalanche photodiodes. They produced much better energy resolution than the other detectors which require photomultiplier tubes or p-i-n and avalanche photodiodes because they convert the energy deposited by the x-ray and gamma ray photon into light not e-h pairs.

High purity germanium (HPGe) has ultra high energy resolution. Because of its exceptional energy resolution and excellent gamma ray absorption property, HPGe is the detector of choice for high accuracy spectroscopy. It only works at liquid nitrogen temperatures which require bulky refrigeration systems which further increases the cost of this expensive detector. HPGe is available in single small crystals and works by collecting the electron hole pairs produced inside the crystal similar to the silicon detectors and does not require PMTs. Because of the large cost this detector is mainly used for applications which require ultra high energy resolution and small size detectors.

BGO, CdWO4 and CsF are excellent high density and high Z scintillators. They have lower energy resolution and light output. Their maximum light emissions peak around 430 nm (FIG. 5) similar to the NaI(Tl) and require PMTs for detection. CdWO4 and especially CsF have shorter decay constants and faster rise times than the others and can be used for timing. The preferred detector of the present invention does not use time-of-flight to determine the direction of the scattered gamma ray photon, therefore, good time resolution is not important.

SACRED Detector

Figure 6:
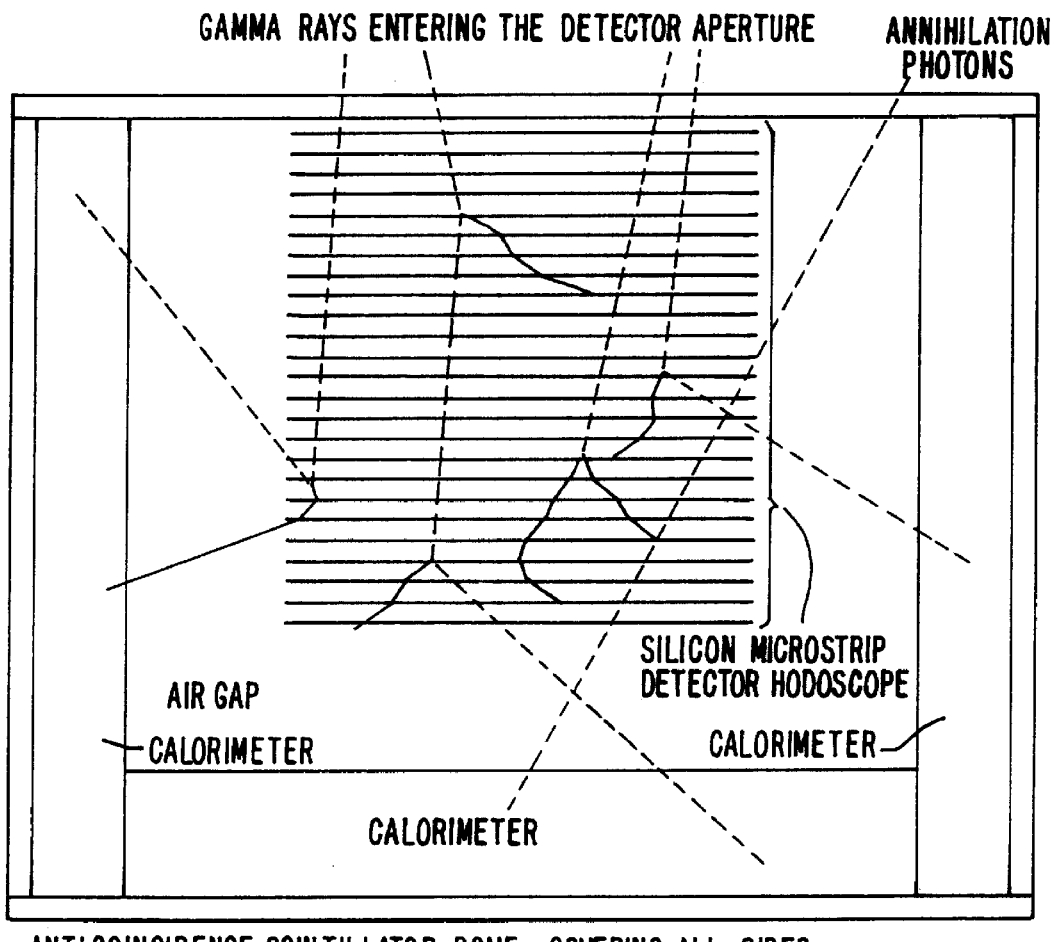
FIG. 6 is an illustration of the cross-section of the SACRED detector.
Figure 7:
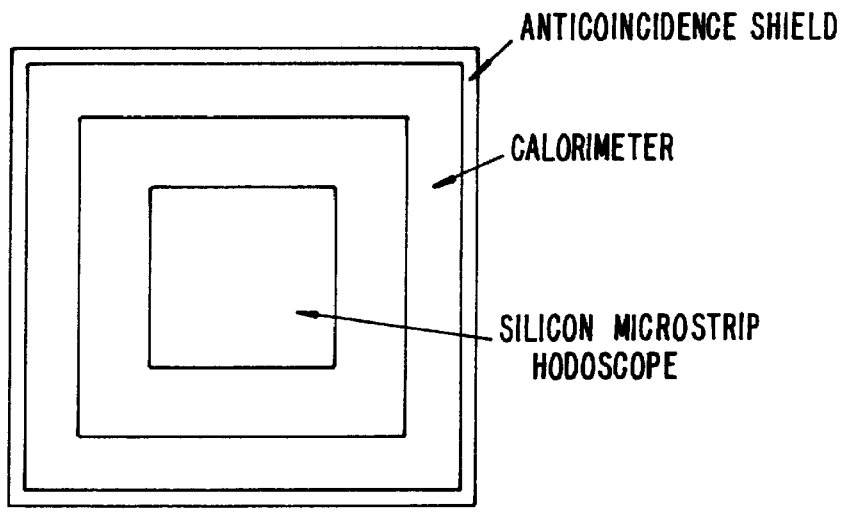
FIG. 7 is an illustration of the top view of the SACRED detector illustrated in FIG. 6 in which the cross-section is square.

FIG. 6 is an illustration of the cross-section of the SACRED detector. A top view of the SACRED detector illustrated in FIG. 6 is given in FIG. 7. In the preferred design, the calorimeter surrounds the hodoscope in the form of a well shaped to detect the large angle Compton scattered photons.

Figure 8:
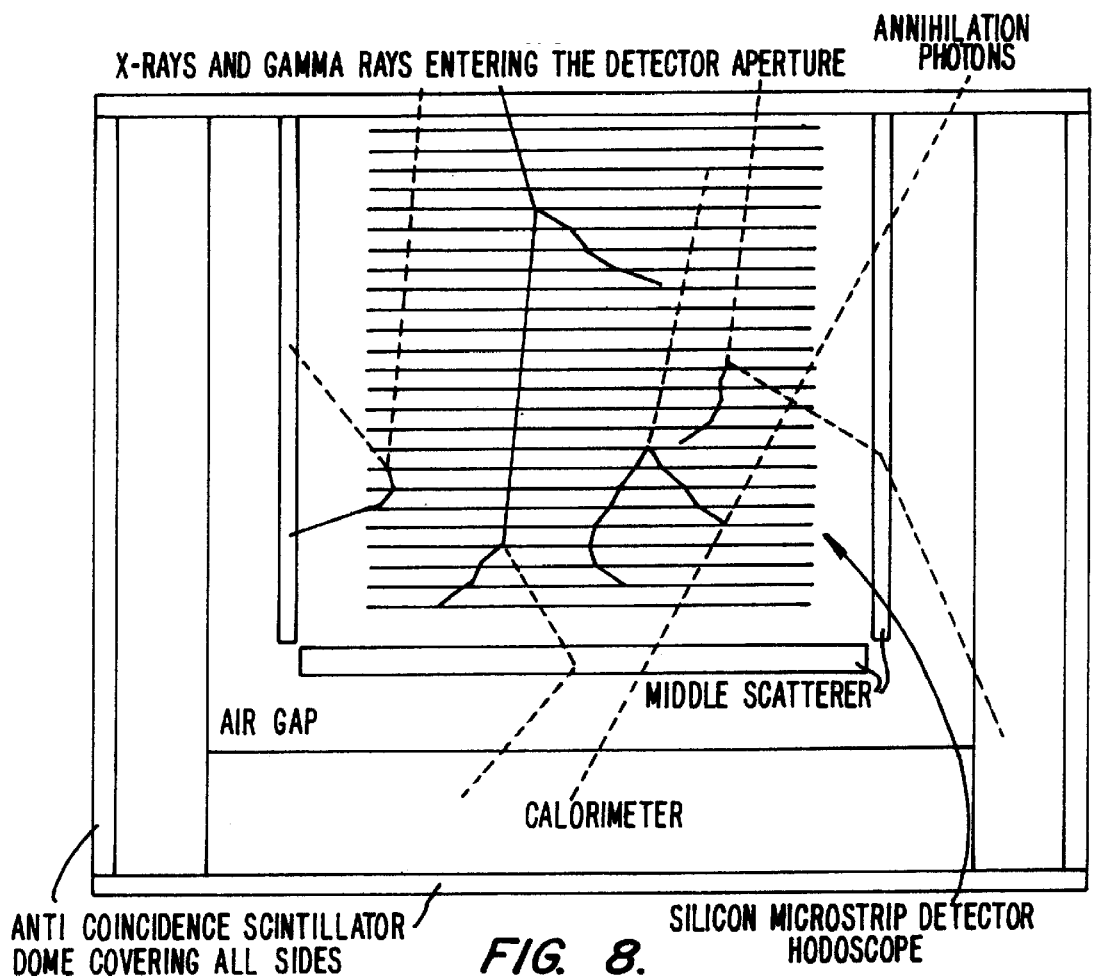
FIG. 8 is an illustration of the cross-section of an alternate design of the SACRED detector which includes a middle scatterer detector.
Figure 9:
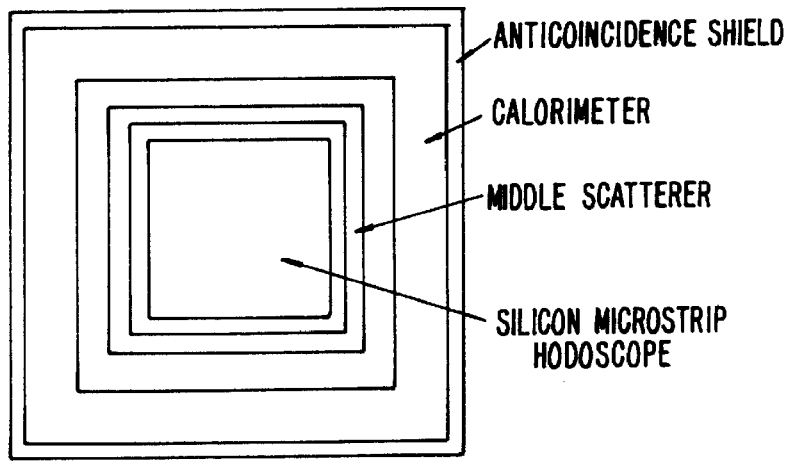
FIG. 9 is an illustration of the top view of the SACRED detector illustrated in FIG. 8 in which the cross-section is square.
Figure 10:
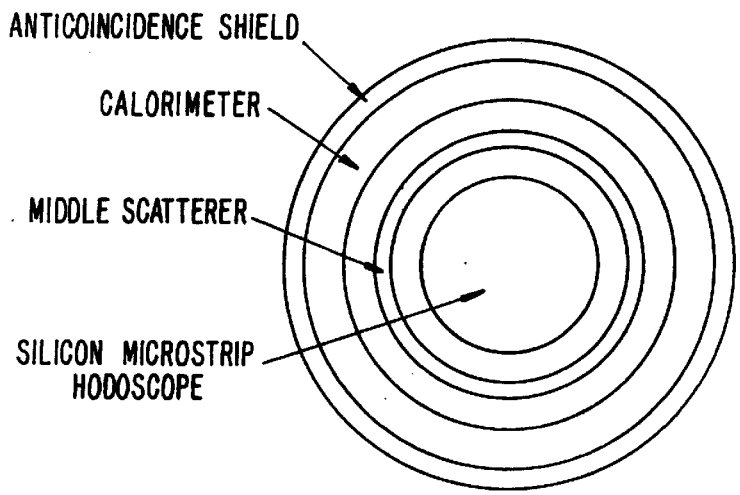
FIG. 10 is an illustration of the top view of the SACRED detector illustrated in FIG. 8 in which the cross-section is cylindrical.

FIGS. 8–10 illustrate a variation on the above design. In this design a middle detector layer is included which surrounds the hodoscope just like the calorimeter although more closely. This layer is made of position sensitive solid state or other type of x-ray and gamma-ray detectors. Preferably it is made from a thin detector layer of about 0.1 mm to 1 cm thickness. This layer performs two functions. First, it increases the energy and angular resolutions for the lower energy x-rays and gamma rays which will now mostly stop in this layer. Second, it allows for three level scatter instead of two (such as a Compton scatter in the hodoscope, a second Compton scatter in the middle layer detectors and get absorbed or make a third Compton scatter in the calorimeter) thus providing more information on the incident x-ray or gamma-ray photon. For example, the total energy and direction of the incident photon can be determined even if the photon makes a Compton scatter in the calorimeter and escapes. FIG. 8 illustrates this functionality.

Figure 11:
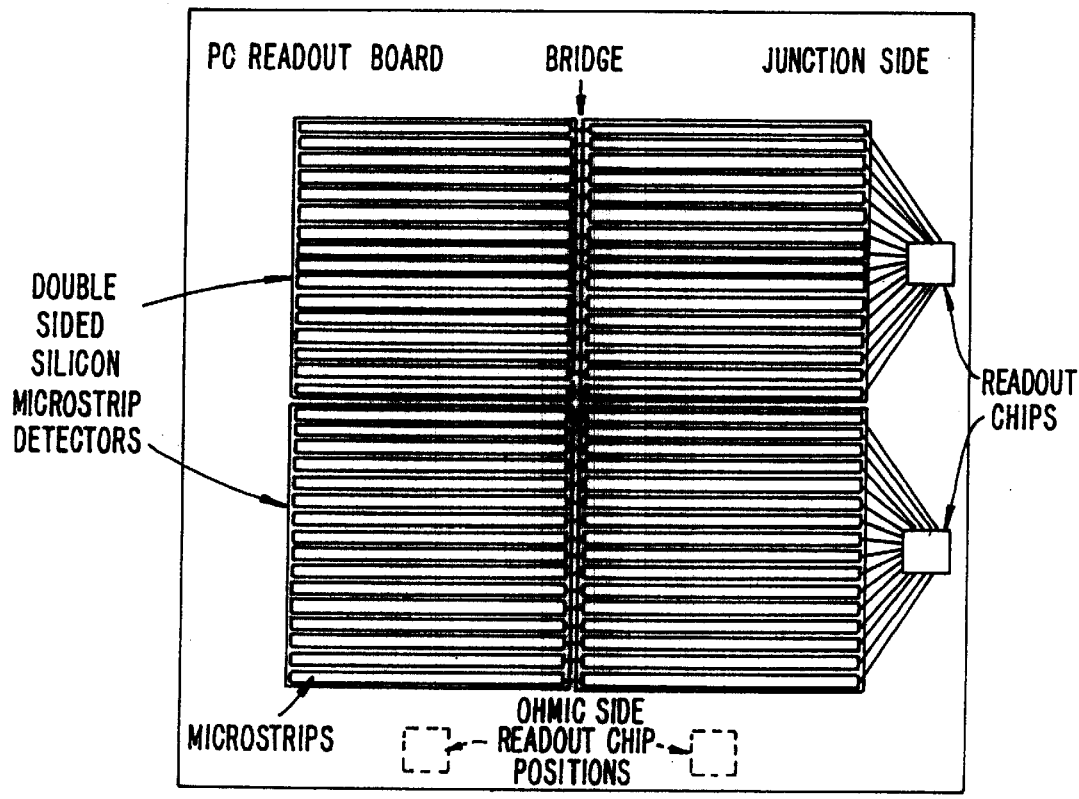
FIG. 11 is an illustration of the top view of a hodoscope detector plane in which four bridged double sided silicon microstrip detectors surrounded by the front end readout electronics PC board is shown.

The thickness of the silicon microstrip detectors is preferably between 200 to 300 microns. A double sided configuration is used with approximately 1 mm pitch strips orthogonal to each other on both sides. Each detector will be made from square silicon wafers with a minimum area of 5 cm by 5 cm. Four detectors will be bridged together to form a square plane of 10 cm by 10 cm area as shown in FIG. 11 surrounded by the front end readout electronics. The hodoscope will contain 20 to 25 detector planes.

Several silicon microstrip detectors can be connected together by bridging the parallel strips in series as illustrated in FIG. 11. Bridging microstrips decreases the readout channel number and related electronics significantly. The bridging silicon strip detectors together and connecting to the readout chip is preferably accomplished using ultrasonic bonding. The readout chips are mounted as near as possible to the silicon detectors to minimize the front end PC readout board size. The fan in from strips to the readout chip pins is gold plated for good quality ultrasonic bonding. FIG. 11 shows the Junction side. The ohmic side (back side) strips runs orthogonal to the junction side so that both x and y dimensions of an interaction in the silicon is measured simultaneously. The bridging on the ohmic side is done similar to the junction side. The position of the readout chips for the ohmic side is shown which are preferably mounted on the reverse side. The output and control signals for the readout chips are not shown as they depend on the chip design.

Figure 12:
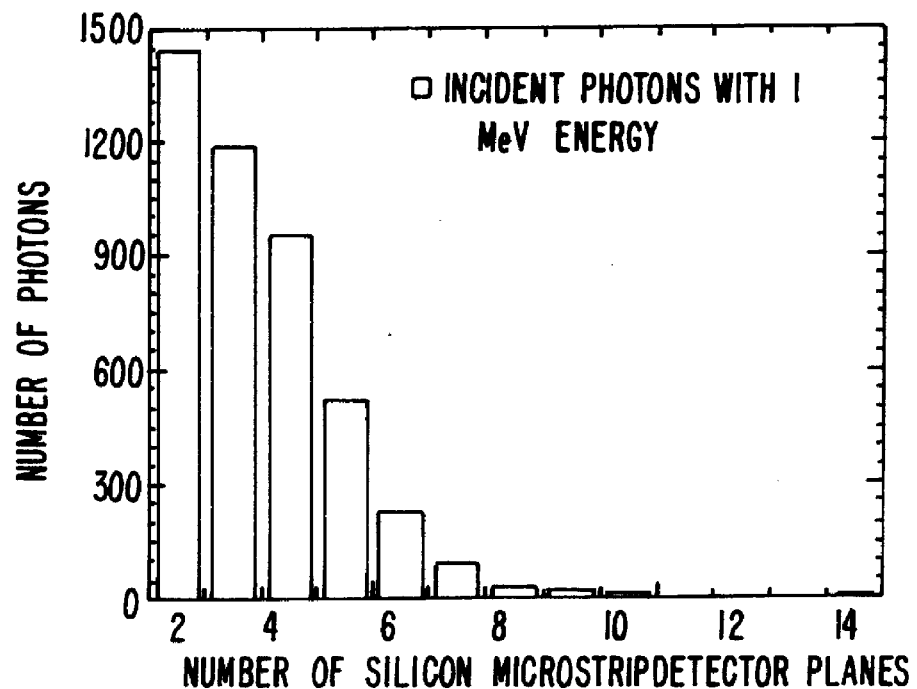
FIG. 12 is an illustration of the recoil electron track length distributions in a silicon hodoscope for 1 MeV gamma rays.
Figure 13:
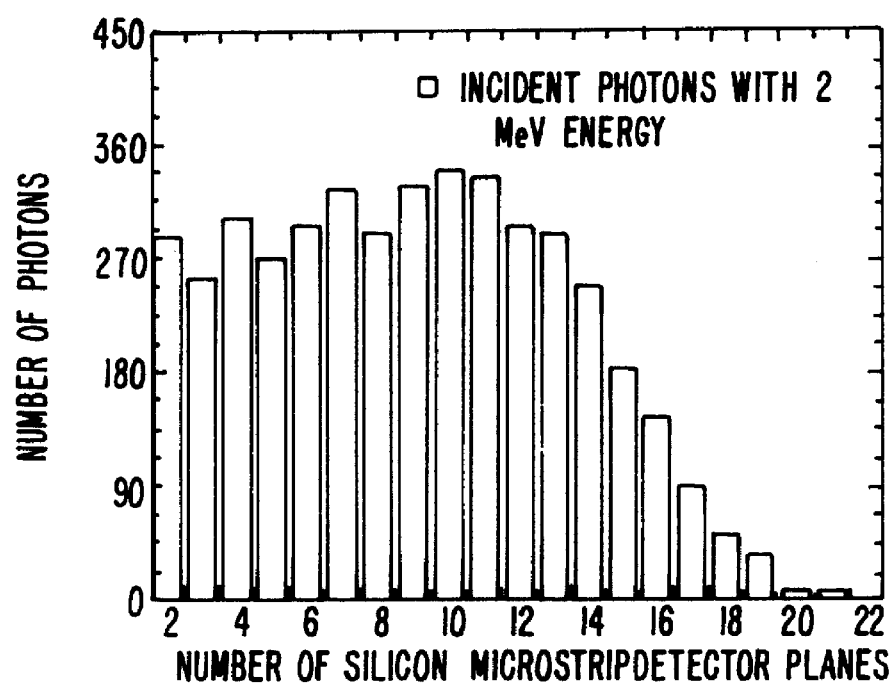
FIG. 13 is an illustration of the recoil electron track length distributions in a silicon hodoscope for 2 MeV gamma rays.

The recoil electron track length in the silicon hodoscope is calculated using the MCNP Monte Carlo program which was developed at Los Alamos National Laboratory. The track length is given as the number of silicon microstrip detector planes traversed by the recoil electron before it stops or drops below the 0.05 MeV detection threshold. The track lengths in number of 200 micron thick detector planes are shown in FIGS. 12–13 for incident photon energies of 1 and 2 MeV, respectively. For 1 MeV gamma rays the recoil electron traverses an average of 3 detector planes. This increases significantly as the energy of the incident photon increases. For 2 and 6 MeV gamma rays an average of 8 and 25 detector planes are traversed. The recoil electrons with long tracks will escape the hodoscope and enter the calorimeter. This is not a problem because the missing energy of the recoil electron in the hodoscope will be recovered by adding the energy they deposit in the calorimeter and the event is fully determined.

Figure 14:
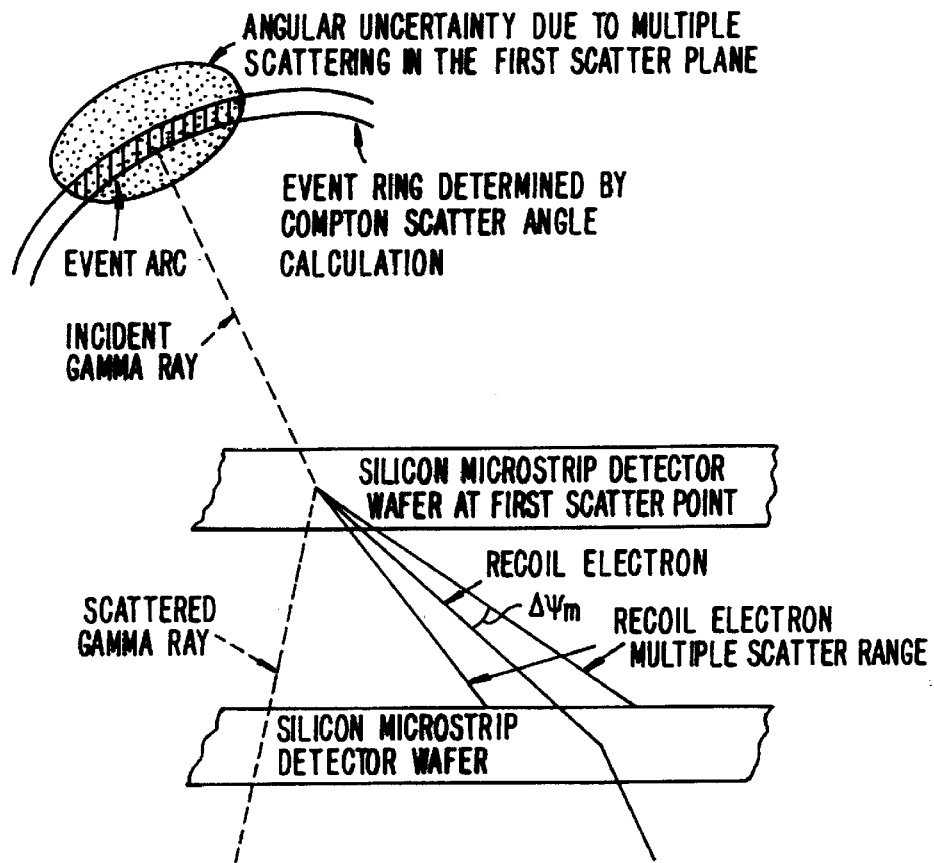
FIG. 14 is an illustration of a multiple scattering event in which the multiple scatter angles along the electron track can be used to determine the direction of motion of the electron.

The multiple scattering of a recoil electron is illustrated in FIG. 14. As the electron loses energy traversing silicon planes the deflection in its trajectory increases significantly. This means that the start and end of the recoil electron track can be identified by measuring the deflections in the track at each detector plane.

In a multiple scatter event, the multiple scatter angle $\theta_0$ is inversely proportional to the momentum and velocity of the particle. The multiple scatter angle increases strongly with the decrease in the momentum and velocity as demonstrated in the simplified formula:

$$\theta_0 = \{[14.1 \text{ MeV}/c]/p\beta\} \, Z_{inc}\{[L/L_R][1+(\tfrac{1}{9}) \log_{10}(L/L_R)]\}^{1/2}$$

where p is the momentum in MeV/c, $\beta$ is the velocity, $Z_{inc}$ is the charge number of the incident particle and L/LR is the thickness of the scattering medium in radiation lengths. This formula is accurate to about 5% for $10^{-3} < L/L_R < 10$ except for very light elements or low velocity particles where the error is about 10 to 20%.

The multiple scatter angles are calculated using the MCNP program which utilizes the more rigorous Moliere theory. There is a large increase in the multiple scatter angles towards the end of the track due to the decrease in the momentum and the velocity of the particle before it stops. At least 4 interactions are required to get the minimum 2 multiple scatter angles per track required to determine the direction of motion of the recoil electron.

The energy loss suffered by the recoil electron at each silicon detector plane is not uniform. The energy loss in each detector plane increases as the kinetic energy decreases. This gives another signature to measure the direction of motion of a recoil electron track. The energy deposited in the first interaction plane is normally much lower than the energy deposited in the last plane where it stops. The energy deposition of the recoil electron is also calculated by the Monte Carlo program. For high energy relativistic particles the energy loss in a medium is constant and minimum. Such high energy particles are called minimum ionizing. As the particle velocity decreases the energy loss by ionization increases. A minimum of 2 interaction points may be sufficient to apply this method since the energy deposition is a scalar quantity. This allows the determination of direction of motion of recoil electrons even with 2 interaction points, also the minimum required to calculate the direction of the recoil electron to reduce the event ring into an event arc. The formula to calculate the direction of motion factor, F, if there are only 2 or 3 interaction points in a track is given by $$F_{2,3} = [E_{Last} - E_{First}]/[E_{Last} + E_{First}]$$

where $E_{First}$ and $E_{Last}$ are the energies deposited in the first and last interaction points assuming the recoil electron is moving into the silicon hodoscope from front to back. The factor F varies from $-1$ to $1$. Positive values indicate that the recoil electron track is progressing from the front towards the back of the detector, and negative values mean the opposite is true.

One may also use differential scatter angle and energy loss, that is the differences not the actual values, to determine the direction of the motion of the recoil electron (possibly) more accurately.

For recoil electron tracks with $\geq 4$ interaction points the product of the two factors should give a more reliable determination of the beginning and end of a recoil electron track. The factor, F, based on track lengths of a $\geq 4$ interactions is revised making use of the large difference in the first and last energy deposition values and the strong difference between the sum of the first and second half of the multiple scatter angle distribution to determine the track direction of motion. The formula is given as $$F_{\geq 4} = \frac{E_{Last} \sum_{i}^{Second\ Half} \theta_i - E_{First} \sum_{i}^{First\ Half} \theta_i}{E_{Last} \sum_{i}^{Second\ Half} \theta_i + E_{First} \sum_{i}^{First\ Half} \theta_i}$$

where $\theta$ is the multiple scattering angle of the recoil electron at each detector plane, $E_{First}$ and $E_{Last}$ are the energy deposited in the first and last interaction points. Other techniques, which can be variations on these, can also be used to determine the direction of the recoil electron track (motion).

The two interactions of the incident photon in the hodoscope and the calorimeter produce an ambiguity which must be resolved. The ambiguity arises because it is not known whether the photon made a Compton scatter in the hodoscope or calorimeter first. The situation is completely symmetric. If this ambiguity is not resolved then the direction of the background photons incident from the back of the detector can be mistaken for true events incident into the detector aperture. Application of the new direction of motion determination discussed above can resolve this ambiguity. If the direction of the recoil electron can be determined the incident photon direction can be resolved.

The effectiveness of this method is demonstrated by the Monte Carlo results. Recoil electron tracks are analyzed individually and the direction of motion of the recoil electron tracks, the beginning and end points, are determined using the multiple scatter and energy deposition at each detector plane along the track.

The summation is carried out for the first and second halves of the recoil electron track, assuming the track is moving from the front to the back of the hodoscope. If F is positive the track is progressing from the front to the back of the silicon microstrip hodoscope and vice versa if opposite. If F is zero the direction is indeterminate. This factor is calculated for many tracks of certain incident gamma ray energies to determine the effectiveness of the new technique. The results of a calculation show that about 4% of the calculated events are negative and resemble upward moving recoil electron tracks progressing from the back of the hodoscope to the front. This is a small effect and decreases at higher incident photon energies. For example, the tracks mistakenly calculated to be moving backward increases to 11% at gamma ray energies of 1 MeV and decreases to 2% at 6 MeV.

The calorimeter is preferably made from CsI(Tl) crystals viewed by photodiodes. The CsI(Tl) has been found to be the most cost effective material for use as the calorimeter. However, the calorimeter can also be built from NaI(Tl) crystals or any other high density scintillator with good characteristics. The calorimeter is formed in the shape of a well surrounding all sides of the hodoscope except the front aperture. The amount of area covered will depend on the cost of the scintillator for a given thickness. The high density scintillator also acts as an excellent active shield for background gamma rays.

The position sensitive CsI(Tl) crystal calorimeter is preferably constructed from 1 cm×1 cm to 2.5 cm×2.5 cm rectangular bars with length varying from 1.5 cm to 2.5 cm. The wide variation of length is due to the energy range of detection. The bottom section of the calorimeter will need longer crystals because the forward scattered gamma rays carry most of the primary photon energy. The extra thickness will stop the higher energy forward scattered gamma rays. The CsI(Tl) crystals on the side walls of the calorimeter can be short, as the photons with large Compton scatter angles carry a much smaller fraction of the primary photon energy. Since the Compton scatter angle will increase with the height of the calorimeter at the side walls, a tapered crystal length may be used; longer CsI(Tl) crystals can be placed on the walls near the bottom of the calorimeter and the crystal length can be gradually reduced upwards toward the rim.

The cost of the side walls of the calorimeter can be further reduced by cutting the height to below the top of the silicon hodoscope. This will cause some backscattered gamma rays at large angles to miss the calorimeter and not be detected. Since the backscatters have lower probability than forward Compton scatters especially at higher primary photon energies, the loss may be negligible.

Figure 15:
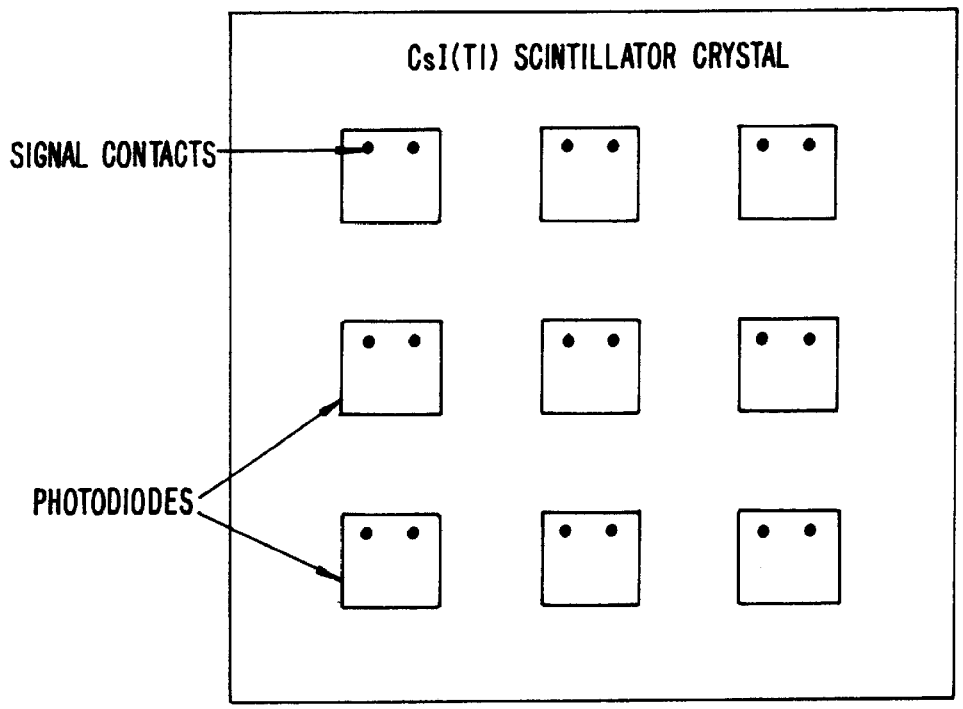
FIG. 15 is an illustration of the bottom of a CsI(Tl) gamma ray camera arrangement using an array of photodiodes viewing te crystal at equal distance to each other.

The above technique uses a mosaic of individual CsI(Tl) crystals for the calorimeter. Each crystal has to be individually viewed by a photodiode. This will require as many photodiodes as the number of crystals. An alternative method is to use flat CsI(Tl) crystals with sufficient size to cover the bottom and the sides of the calorimeter. Each flat crystal can be viewed by photodiodes placed at equal distance to each other on the back side of the crystal as illustrated in FIG. 15. This system resembles an Anger camera system with a flat NaI(Tl) crystal viewed by PMTs.

The position of the interaction point is determined from the centroid of the pulse heights observed by the adjacent photodiodes surrounding the interaction point. The Anger cameras normally use about 1.5 cm thick flat NaI(Tl) crystals. The thickness of the CsI(Tl) is greater for this application as it has to stop higher energy photons. The Anger camera and this application are not identical.

For Anger cameras, a better position resolution is normally obtained for the gamma ray interaction point compared to that of the cathode size of the individual PMTs. The same can be true for the CsI(Tl) gamma camera. In this case it may be possible to achieve pixel sizes smaller than 1 cm×1 cm at the calorimeter. This will improve the geometric angular resolution of the SACRED detector and enhance the angular resolution.

An anticoincidence shield usually surrounds all sides of the detector as shown in FIGS. 6–10. It is mainly used to veto charge particles such as electrons, positrons and protons incident on the detector from all directions. Charged particles deflect in the Earth's magnetic field and produce a nearly isotropic background. They cannot be used as a signal unless they are well beamed, as in the accelerated particle beam weapons. The best low cost material for an anticoincidence shield is a fast plastic scintillator such as NE-102A. Thicknesses between 0.5 to 1.5 cm are normally used for this purpose. Photomultipliers view the plastic scintillator from sides through Lucite light guides. Thinner scintillator is normally selected for the aperture of the detector to reduce the Compton scatter of gamma rays in the plastic which change the direction of the incident gamma rays. Since the plastic scintillators have low density and low average Z, the Compton scatter probability is very low and up to 1.5 cm thick scintillator can be used in front of the detector aperture without significant effect. For applications where charge particle background is not significant the anticoincidence shield can be omitted. This could be the case for observations on ground where the cosmic ray background may not be high enough to cause problems. Also the top hodoscope layer can serve as an anticoincidence shield by requiring that there is no track in this layer in all events that are accepted as x-ray and gamma-ray events.

SACRED Detector Data Acquisition System

The design of the data acquisition system is related to the front end electronics of the silicon microstrip hodoscope and the calorimeter. A detailed description of the electronics is included in co-pending application Ser. No. 08/460,489, which is incorporated in its entirety for all purposes. The electronics is considerably simplified by the elimination of the time-of-flight measurement which required the generation of separate fast timing signals from the silicon microstrip detectors and the CsI(Tl) crystals viewed by photodiodes. However, some dedicated fast CAMAC modules must used to readout the silicon hodoscope and the calorimeter.

Figure 16:
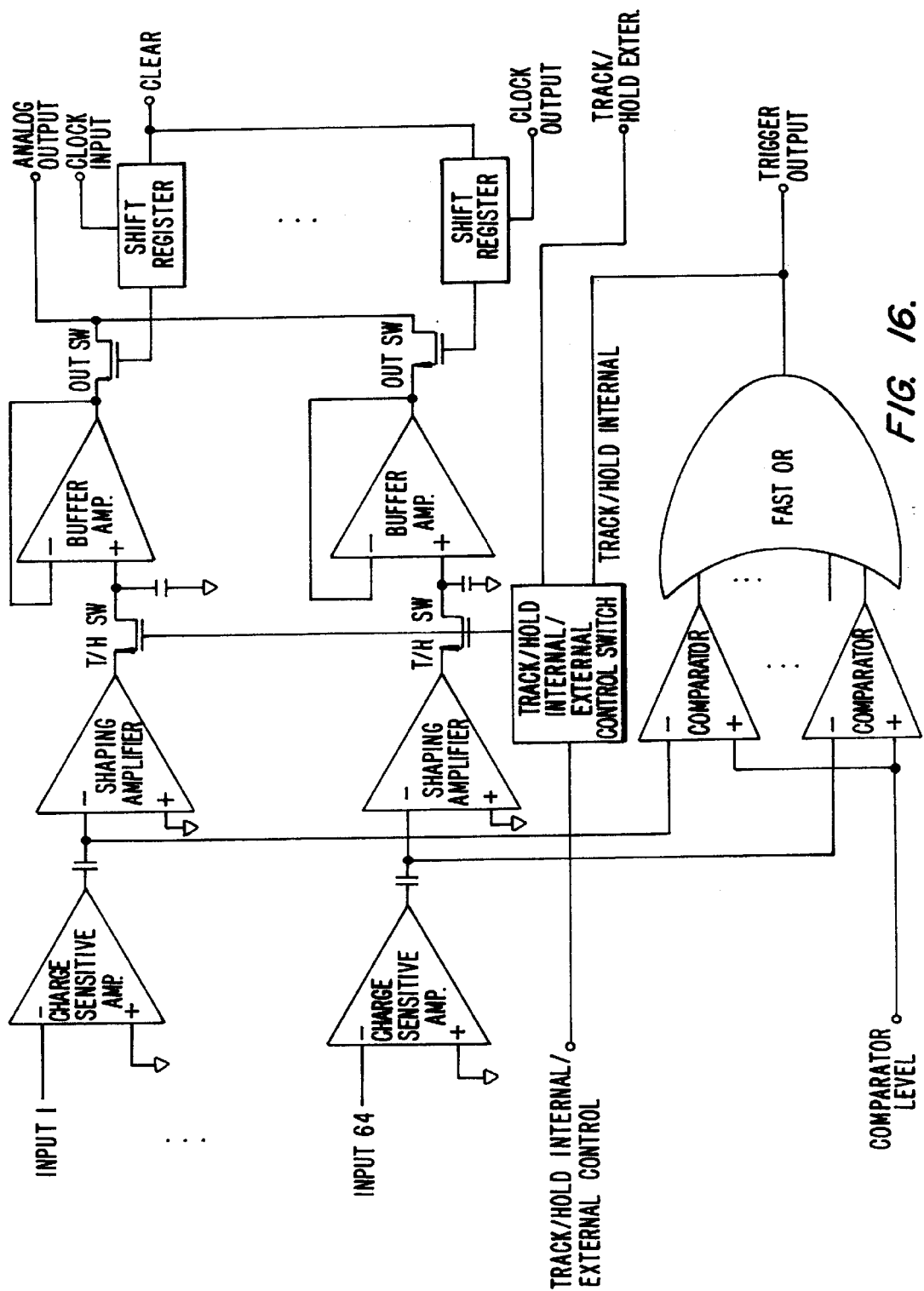
FIG. 16 is a schematic diagram of a possible 32 or 64 channel silicon microstrip detector readout chip with trigger output capability.

The most important part of the front end electronics for the silicon microstrip hodoscope is the microstrip readout chip. The Amplex chip is an excellent low noise, high gain and easy to use interface device. However, it does not have a trigger output capability. This limitation may be solved by using the trigger from a plastic scintillator placed behind the silicon microstrip detector planes. The signal generated by the calorimeter is used as the trigger to readout the silicon microstrip hodoscope. However, this is not an elegant solution since the calorimeter will have background triggers that are not coming from the Compton scattered photons. This will produce false readouts of the hodoscope and increase dead time. The legitimate events could be selected by software, but would increase the computation time. The best solution is to design a readout chip with a trigger output capability. This is not complicated as comparators can be incorporated into the readout chip to detect a strong signal above the externally set threshold and the outputs of the comparators can be fanned in using a fast OR circuit to produce the single trigger output. FIG. 16 shows a possible microstrip readout chip diagram based on the Amplex chip with the trigger output capability using comparators.

The circuit is preferably designed to have 16, 32 or 64 inputs with each input from the microstrip detector directly coupled to a charge sensitive amplifier. The outputs of the charge sensitive amplifier are AC coupled into a shaper amplifier with a time constant of about 1 ms. The output of the shaper amplifier goes into the track and hold (T/H) switch. The T/H switch can be controlled externally or can be activated internally from the trigger output with a delay set to turn the hold on at the peak of the shaped pulse. The T/H switch is connected to the input of the buffer amplifier through the voltage following capacitor. When the T/H switch is open the voltage on the capacitor is held constant and the voltage level is buffered on to the analog output switch. A shift register connects each buffer output to the single analog output pin in sequence, from input 1 to N, by an external clock input. The shift register also has an external clear input to reset it and a clock output to daisy chain it to other readout chips. Only one clock input is sufficient if the clock outputs are connected in serial to the clock inputs of the adjacent readout chips. The charge sensitive amplifier outputs can be fanned out to comparators with a common external level adjustment. The outputs of the comparators can be fanned in through a fast OR circuit which will produce a trigger signal if any comparator input exceeds the set threshold. The trigger signal can also be used with a suitable delay to control the T/H switches to apply a hold signal at the peak of the pulse coming out of the shaper amplifier.

It is possible to improve the functionality of the readout chip using the extra versatility introduced by the comparators. The design shown in FIG. 16 does not produce information on which strip has the information and all the strips are readout to find the strip that has the signal. A simple logic circuit could be added to the design which would detect the channel with the signal from the comparator outputs, apply track and hold signals and connect the strip with the signal to the analog output pin. At the same time it could encode the address of the strip that has the information and output it as the address of the strip with the signal. There can be an occasional signal on more than one strip. Multi-hits can be detected and an output can be generated to warn of a multi-hit signal. The trigger signals are generated for each readout chip. They have to be externally processed for the hodoscope in coincidence with the calorimeter to produce the single trigger signal to activate the data acquisition system.

The extra improvement described above to increase the functionality of the readout chip is not absolutely necessary, because the hodoscope can be formed from many silicon strip detectors and each detector can have at least two readout chips. Since the recoil electron track will activate several detectors, the serial readout shown in FIG. 16 will only be used for several chips. This does not constitute a major readout overhead.

Figure 17:
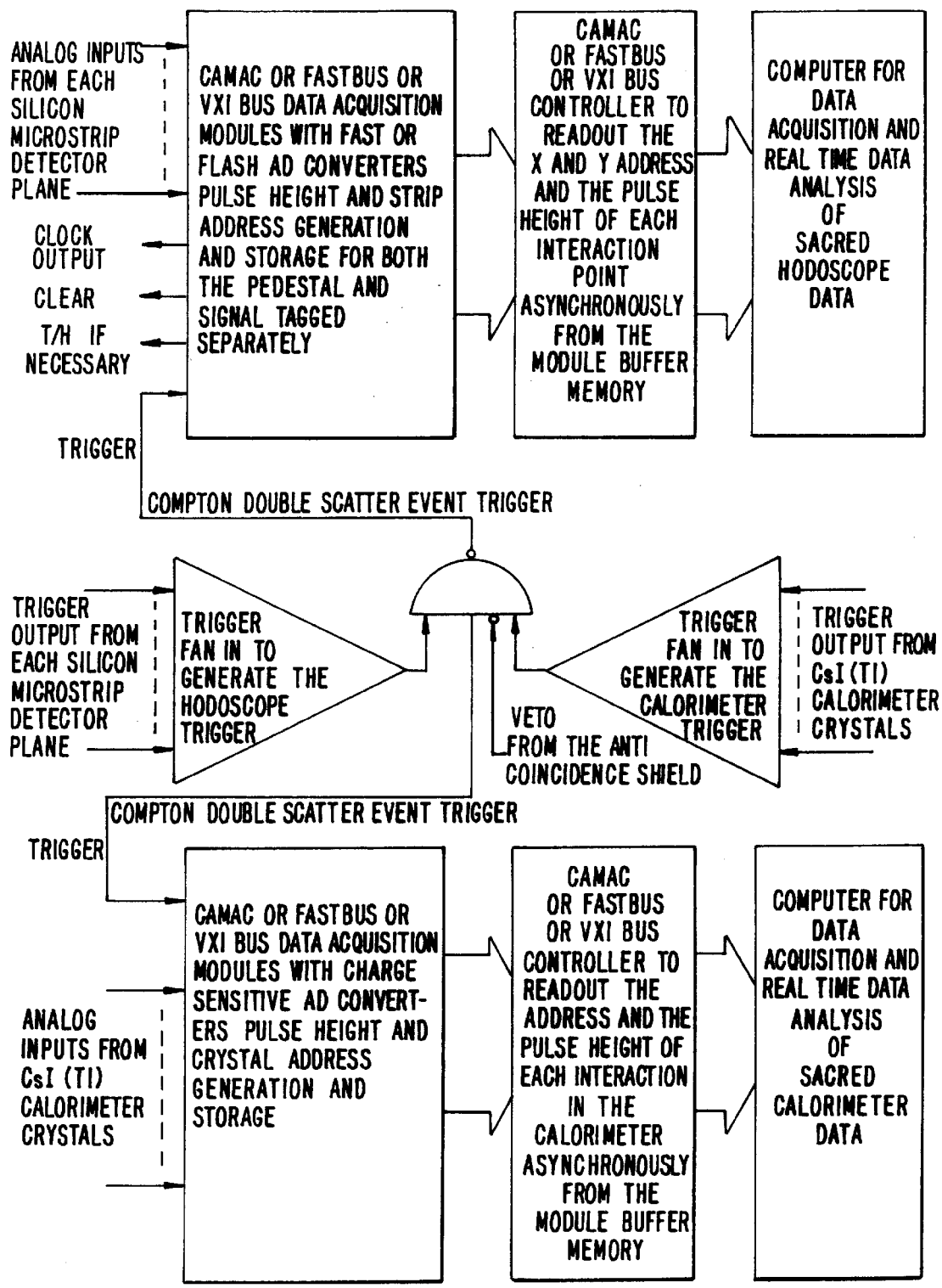
FIG. 17 is a block diagram of a real time data acquisition system.

A block diagram of a readout electronics system is shown in FIG. 17. The electronics has two similar sections for the hodoscope and the calorimeter readout. A true event is a coincidence between the hodoscope and the calorimeter.

Since most of the time both sides observe more than a single interaction, a fan in system will be used to convert the several trigger signals into one master trigger. The fan in can be designed to recognize a track with adjacent planes producing the signal and to reject random coincident events for the hodoscope.

The two master trigger signals from the hodoscope and the calorimeter are sent to a coincidence unit to create the Compton double scatter event trigger. The plastic anticoincidence shields to reject the charged particles are also fanned into one master trigger signal and the output is sent to the veto input of the coincidence unit. The Compton double scatter trigger signal is only generated if there is no veto input from the anticoincidence counters and there is a master trigger signal from both the hodoscope and the calorimeter. This arrangement does not effect the pair produced events because at least one of the positron annihilation photons is expected to be detected in the calorimeter.

The Compton double scatter event trigger activates data acquisition for both the hodoscope and the calorimeter simultaneously. Several CAMAC, Fastbus or VXI bus modules can carry out the data acquisition. The CAMAC system is the most cost effective system. The custom designed data acquisition modules for the hodoscope produce the necessary microstrip readout chip control electronics, such as the T/H (if not generated internally in the readout chip), a Clear signal to reset the shift registers and the Clock pulse to multiplex each strip to the analog output. The analog input channels from different hodoscope planes are read out synchronously with the Clock pulse output. The module converts the pulse height information received from the analog output pin to a digital number. In parallel to reading the hodoscope data, it also digitizes the signal(s) from the calorimeter. Immediately after reading out the last signal it clears the hodoscope to reset the readout chip so that it can receive the next event. It is assumed that the analog output of each readout chip in each detector plane is fanned in to allow a single signal to be sent to the readout module. It is also possible to design a microstrip readout chip that can internally connect the strip which has the signal to the analog output and also produce the encoded address of the strip. In such a case the clock output will not be necessary and the silicon microstrip detectors can be readout asynchronously and much faster.

The custom made CAMAC, Fastbus or VXI bus modules are connected to the bus or crate controllers which are standard devices and available off the shelf. The controllers connect the modules to the data acquisition computer. Depending on the data rate and readout overhead, a single or separate computers can be used to read the hodoscope and the calorimeter. The computer stores data on hard disk, optical drive or nonvolatile RAM depending on the application. If the data acquisition overhead is not high then one of the computers can analyze the data in real time or a separate computer can be used which can access the storage media asynchronously. The results of the data analysis are imaged onto the field-of-view through a display system and source positions are reported in real time.

Energy and Angular Resolution

Figure 18:
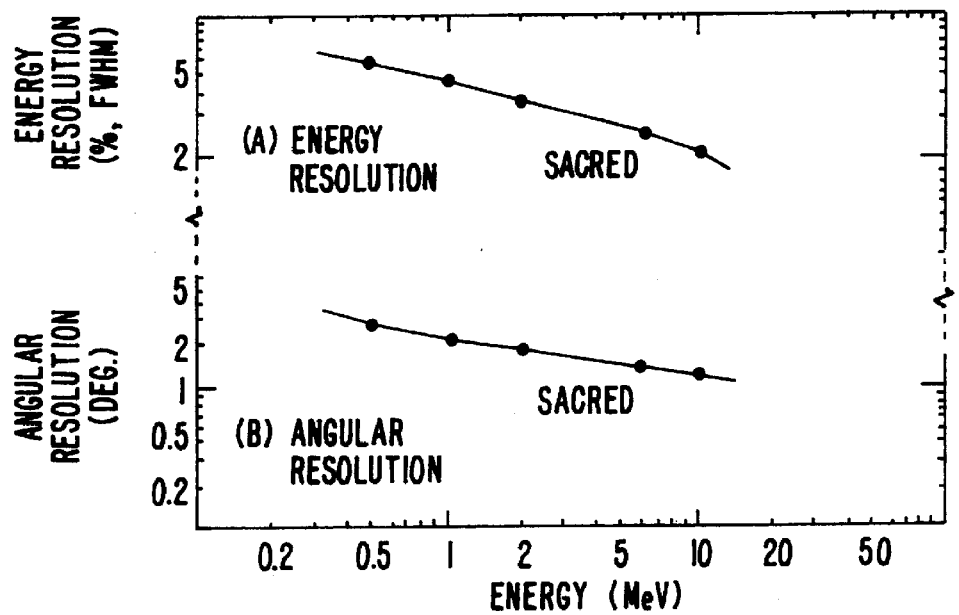
FIG. 18 is an illustration of the energy resolution and angular resolution for a SACRED detector.

FIG. 18 is an illustration of the calculated energy and angular resolution (FWHM) of the SACRED detector. A position resolution was assumed at the hodoscope of 1 mm×1 mm (double sided silicon microstrip detectors with 1 mm pitch) and at the calorimeter as 1 cm×1 cm. The calculations were carried out for 0.5, 1, 2, 6, 10, and 25 MeV. Compton scatter angles were not restricted and threshold energyies of 0.05 MeV were applied to the hodoscope and the calorimeter. The angular resolution is given here in the form of a FWHM value. The direction of a point source can be determined with much higher accurac compared to the angular resolution, to a fraction of a degree, with sufficient statistics.

Effective Area-Efficiency Factor and Sensitivity

The effective area-efficiency factor and sensitivity are the important characteristic of a detector. The calculation of these factors can be done in different ways.

Figure 19:
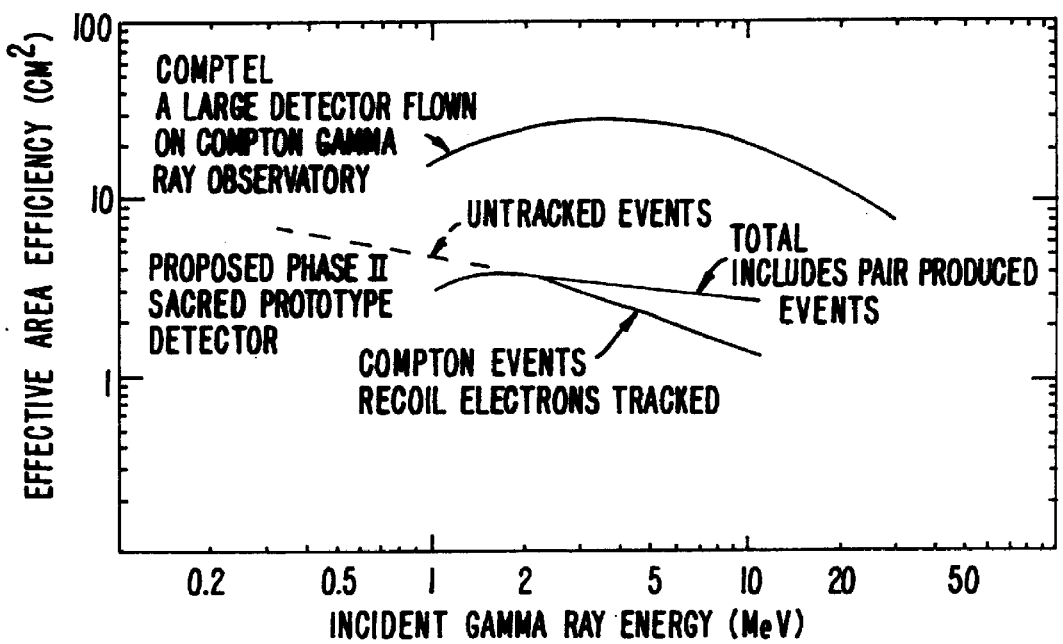
FIG. 19 is an illustration of the effective area-efficiency factors for Compton, pair produced and total events for gamma rays of normal incidence to the 0.46 m×0.46 m×0.43 m SACRED detector aperture and for the large 1.7 m diameter and 2.6 m high COMPTEL detector flown on the Compton Gamma Ray Observatory.

The effective area-efficiency factor is plotted in FIG. 19. The solid lines are the tracked events and the dashed line extending to low energies includes the untracked events which were analyzed as event rings. Untracked events are detected when the Compton scattered recoil electron stops in the same silicon detector it is created. Therefore, the recoil electron direction can not be measured and the direction of the incident electron is only known as a ring in the field-of-view. If the recoil electron traverses two or more silicon microstrip detectors then the incident gamma ray direction is restricted to a short arc in the field-of-view. Above 1 MeV incident gamma ray energies most of the events are tracked and below 1 MeV untracked, for silicon microstrip detector thicknesses of 200 to 300 micron.

The above efficiencies were calculated for a simulated gamma ray beam incident normal to the detector at its center. To find the effect of the angle of incidence on the detector efficiency, the response of the detector to gamma rays generated with uniform isotropic distribution must be studied. The results show that the detector efficiency for the gamma rays entering the detector aperture, zenith angles from 0° to 60°, is high. The gamma rays incident from the side and back of the detector at zenith angles from 90° to 180°, have low efficiency as expected since the new discrimination method that makes use of the direction of motion determination for the recoil electron track is effective. Also the CsI(Tl) calorimeter is a good gamma ray absorber. The efficiency for gamma rays incident from the front of the detector is about a factor 30 higher than for gamma rays incident from the back. This is important since the background produced by gamma rays incident from the sides or back will not be significant.

Figure 20:
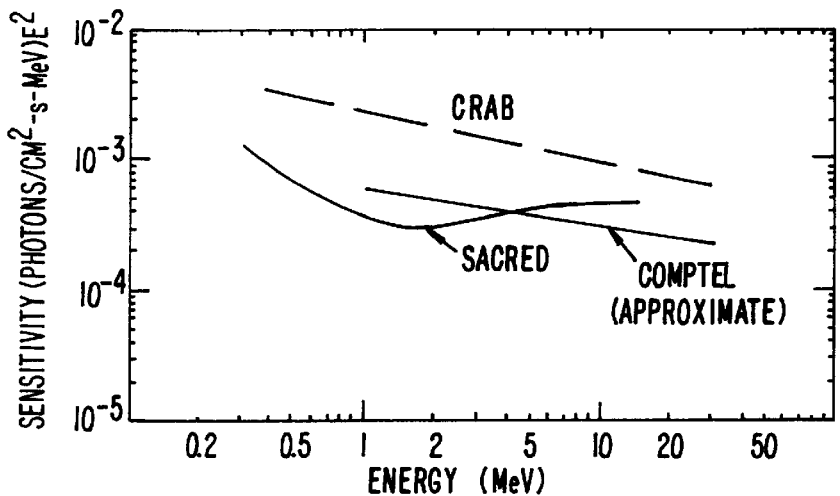
FIG. 20 is a graph of the δ sensitivities for an embodiment of the SACRED detector.

The calculated 5 σ sensitivity curve for an embodiment of the SACRED detector is shown in FIG. 20. Note that the sensitivity plotted is multiplied by $E^2$ to normalize to the spectral power law. The sensitivity of this detector is best for incident gamma rays between 1 and 5 MeV.

At higher energies the sensitivity is reasonably constant, but there is some loss of sensitivity as the stopping power of the detector decreases with an increase in the energy due to the smaller size of this version of the detector. At lower energies the sensitivity is also reduced as the large angle Compton scattered gamma rays that miss the calorimeter are lost. The sensitivity of the COMPTEL detector on Compton Gamma Ray Observatory is also shown. The COMPTEL detector is a conventional Compton double scatter detector without recoil electron tracking. Its diameter is about 1.7 m and its height is 2.6 m. The total, steady and pulsed, Crab flux is also shown. The volume of this version of the SACRED detector is 1.5% of the large COMPTEL detector. The area-efficiency factor for the prototype detector is about 10% of COMPTEL. However, due to the design and recoil electron tracking technique the SACRED detector has about equal sensitivity as shown in FIG. 20.

Compton Double Scatter Data Analysis

For each gamma ray detected by the first and second generation Compton double scatter detectors an "event ring" on the sky containing the source direction can be measured.

The half-angle of the cone (see FIG. 2) is the Compton scatter angle, σ. The overlap of the rings gives the source direction. The "angular resolution" is the angular width of the ring. This angular resolution depends on the energy resolution in the hodoscope and the calorimeter and the geometric uncertainty in the scattered photon direction. Measuring the recoil electron direction in the proposed Compton double scatter detector reduces the event ring to an arc centered on the source direction (FIGS. 2 and 14). It significantly reduces background and provides a "true imaging" capability for Compton detectors. The event arcs produces dramatic improvement on the signal to noise ratio compared to event rings. The data analysis methods discussed below can be applied to both types of data.

The "true imaging" is achieved by determining the x and y coordinates of the interactions in the first two planes of the Compton recoil electron track in the silicon microstrip hodoscope. With both the electron and scattered gamma ray directions known and their energies measured, a unique direction is found for each event.

Many different data analysis methods can be applied to the data of the prototype detector. Some of the methods that can be used are the standard technique, maximum likelihood and maximum entropy methods. A new method, direct linear algebraic deconvolution, is an alternative to the pervious data analysis techniques. Any of these methods can be applied for the SACRED detector data analysis.

The standard method has many variations but in general the field-of-view is divided into a two dimensional array of equal size angular bins. The bin size is normally set to the FWHM angular resolution. For each event a weight of 1 is uniformly distributed over the event ring (for untrackable recoil electron events) or event arc (for tracked events) and each bin that overlaps the event ring or arc are incremented by the probability value contained within its boundary. This technique normalizes the distribution so that the correct flux can be obtained. This method produces an inherent smooth background distribution because the image pixels are incremented by probabilities rather than single counts.

The track events can also be treated separately, because for a tracked event a unique direction is determined for the recoil electron which allows a unique direction attributed to the photon. Therefore, in this method the bin that the calculated incident photon direction falls into can be incremented by 1. The calculated incident photon directions will form an arc due to the multiple scattering in the first Compton scatter plane. This method produces a somewhat fluctuating background distribution. However, both methods can be used effectively.

The image is formed by incrementing the bins that are overlapped by the event ring or arc proportional to the projected area. To determine the correct gamma ray flux from the image, the event ring or arc is normalized to have unit area as described above. A point or an extended source appear where many event rings or arcs cross each other. The signal is much stronger for event arcs as they have much smaller area than the event rings and the contribution to the signal at the position of the source is higher.

The standard data analysis technique is the method of choice as it is well understood and extensively used. It is also a non-iterative technique and fast real time data analysis can be carried out.

The maximum likelihood and maximum entropy methods are iterative techniques and may not be suitable for real time data analysis unless fast computers are used. These techniques improve image quality, especially the maximum entropy method. They can sharpen the point source images and smooth background fluctuations. However, the normalization is lost and the source fluxes cannot be calculated.

Recently a new Direct Linear Algebraic Deconvolution (DLAD) method has been proposed for imaging Compton double scatter data. The present Compton detectors provide two basic parameters for each event that are related to the incident photon direction, the scattered photon direction and the Compton scatter angle. For a given scatter angle the pattern of scattered photon directions for a given incident photon direction is readily determined from the detector's calibration data. It is a ring for untracked and an arc for tracked recoil electron events about the incident photon direction.

As an elementary example, for fixed scatter angle and incident energy, a 2-dimensional source field can be converted into a 2-dimensional detector field of Compton scattered photon directions with a 4-dimensional response matrix. For a well-conditioned response matrix, its inverse can be used to generate an image field from the observed distribution of scatter directions. The matrix inversion only has to be done once. The technique can be extended to include a range of energies and scatter angles.

In general, the direct linear least squares solution of large linear Poisson problems, especially deconvolution problems, has not been done for the DLAD method. This can be attributed to: (i) numerical difficulties inherent in all large linear least squares problems; (ii) difficulties peculiar to Poisson data, mostly with the use of the "modified chi square method" and various close relatives; and (iii) problems associated with the finite resolution of the deconvolution kernel of the instrument.

Considerable progress in dealing with the purely numeric issues in the first case has occurred during the past decade or two. Problems in the third case result from attempting to extract more resolution information than the data allow, given the limitations of the instrument. Then the response matrix $R_{kj}$ becomes highly ill-conditioned (the condition number $\kappa = \|R\|*\|R^{-1}\|$, where $\|\bullet\|$ is the matrix norm, becomes large) or singular. It has recently been shown for direct algebraic spectral deconvolution how these difficulties may be overcome. Direct linear deconvolution of gamma-ray spectra has actually been standard for many years using these methods in the oil-well logging industry.

Detection of Pair Produced Events

The pair produced events are different than the Compton scattered events. The signature of a pair produced event in the SACRED detector is two simultaneous tracks in the form of an inverted V with a single common vertex point in the silicon hodoscope. The dual track is due to the electron-positron pair created in the hodoscope. The inverted V track is accompanied by one or two 0.511 MeV interactions in the calorimeter resulting from the absorption of the 0.511 MeV photon pair created by the annihilation of the positron. One or both of the electron-positron pair can escape the hodoscope and enter the calorimeter. These will be legitimate events and the missing particle energies can be obtained from the calorimeter since the tracks of these particles are already measured and their position of interaction at the calorimeter can be determined. The pair production starts to become important for incident photon energies above 5 MeV.

Application of SACRED to SDI Objectives

The application of the SACRED detector to SDI objectives is discussed below. The arguments given here are based on information obtained from public scientific publications and may not be very accurate since much of the required information on nuclear warheads is classified.

Figure 21:
FIG. 21 is an illustration of an application in which a SACRED detector is mounted on the cone of a scout interceptor missile, thus providing exoatmospheric midcourse discrimination of nuclear warheads from decoys.

One The proposed application is to mount a full size SACRED detector in the cone of a scout interceptor missile which is launched ahead of other interceptors. The scout is timed to intercept the ICBM bus at the initial stages of RV deployment. The SACRED detector measures the gamma ray output of the RVs in real time as it approaches them as illustrated in FIG. 21. The images of the RVs obtained by the onboard radar or infrared sensors can be superimposed on to the computer simulation of the SACRED field-of-view as illustrated in FIG. 22 so that fast identification of the RVs which contain nuclear warheads can be made.

The key to warhead identification is the detection of gamma rays emitted by the radioactive material contained in the nuclear warhead. The direction and the energy of the gamma rays that enter the detector aperture are measured. The SACRED detector has high sensitivity and wide field-of-view. The wide field-of-view, about 120°, is demonstrated in FIG. 21.

FIG. 22

Figure 22:
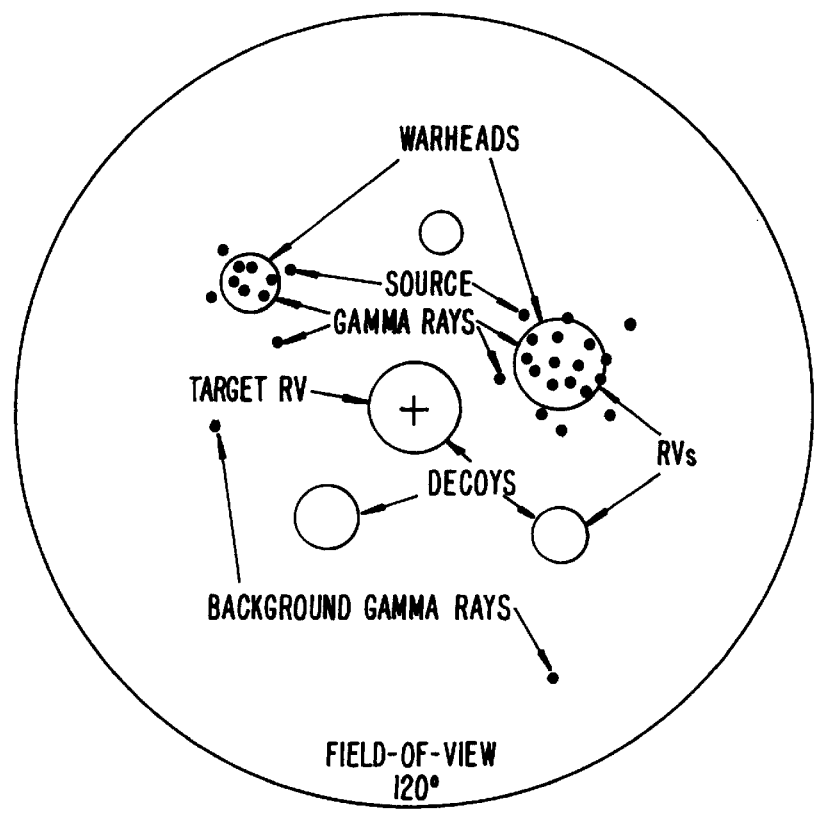
FIG. 22 is an illustration of a computer simulation of the SACRED field-of-view during approach to a target RV in which the radar or infrared images of the RVs are superimposed onto the field-of-view for warhead identification.

FIG. 22 shows a computer simulation of the SACRED field-of-view. It shows the target RV and the other RVs at various distances to the scout interceptor. The target RV is a decoy and two of the remaining RVs emit gamma rays which are identified as the warheads in this scenario. Due to short flight time before impact the diffuse cosmic background gamma ray flux is negligible, about 0.6 photons in 10 msec. The images of the RVs move radially outward from the center of the field-of-view as the scout approaches to its target. The direction of motion of the RVs can be determined from this information in real time and transmitted to the ground control or to the interceptors following the scout with the information on which RVs contain warheads. This information will enable the interceptors to select and track the correct RVs that contain nuclear warheads.

Figure 23:
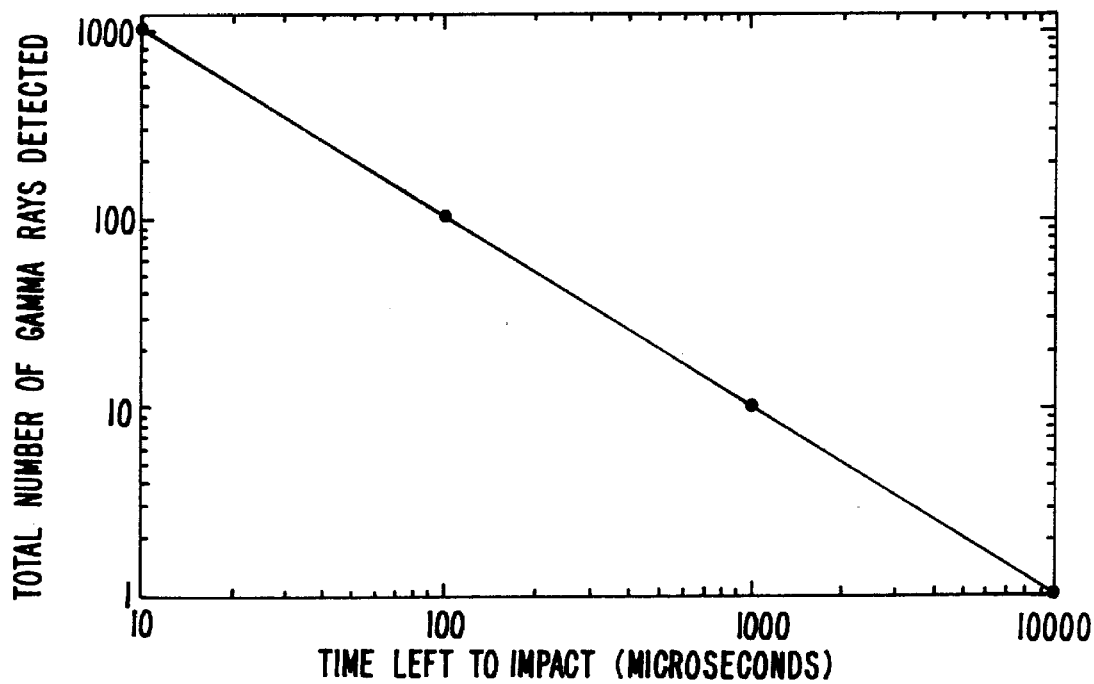
FIG. 23 is a graph of the number of integrated gamma ray photons detected from a nuclear warhead producing $5 \times 10^8$ gamma rays per second by a SACRED detector mounted on the cone of an interceptor missile where the data accumulation starts 1 sec before impact.
Figure 24:
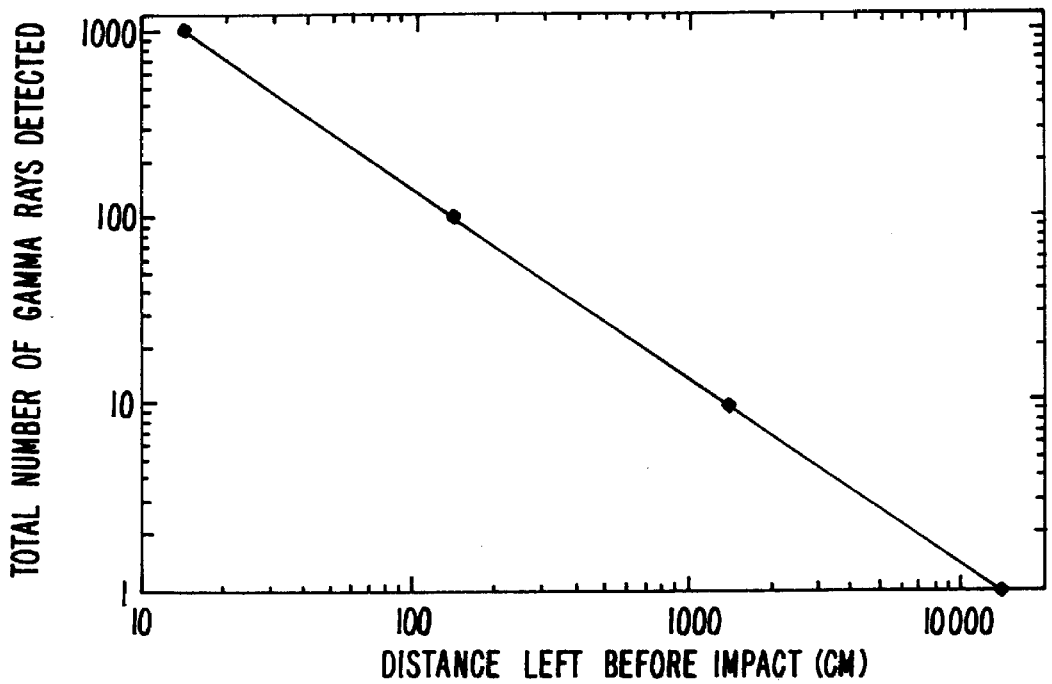
FIG. 24 is a graph of the number of integrated gamma ray photons detected from a nuclear warhead producing $5 \times 10^8$ gamma rays per second by a SACRED detector mounted on the cone of an interceptor missile where the data accumulation starts 1 sec before impact.

If a typical nuclear warhead encapsulated within the carrier missile produces $5 \times 10^8$ gamma rays per second then the detection of these photons with a full size SACRED detector mounted in the cone of a scout interceptor can be calculated. FIGS. 23–24 show the results of the calculation of the total number of photons detected against time or distance before impact. The area-efficiency factor of the SACRED detector is taken as 500 cm$^2$ for this calculation. The RVs and the scout missile are assumed to approach each other at 7 km/s. The time before impact calculation is based on 14 km/s speed. The formula for the accumulated counts C is derived by integrating the count rate formula $$dC/dt = (LA\epsilon)/(4\pi R^2) = \{(LA\epsilon)/(4\pi[vt]^2)\}$$

to obtain the formula for counts $$C = \{(LA\epsilon)/(4\pi v^2)\}\{(1/t_1)-(1/t_0)\}$$

where L is the source luminosity ($5 \times 10^8$ γ/s), $A\epsilon$ is the area-efficiency factor (500 cm$^2$), R is the distance to the source, v is the approach speed (14 km/s), $t_0$ and $t_1$ are the time to impact at the start and at the end of integration. If $t_0$ is large compared to $t_1$, C is proportional to $1/t_1$.

The closer the scout approaches the target the more photons are detected. The detection of a significant number of photons starts about 10 ms before impact. In 10 ms time interval the number of diffuse galactic background gamma ray photons ($F_{Diff} = 1.1 \times 10^{-2}$ E$^{-2.3}$ photons cm$^{-2}$ s$^{-1}$ sr$^{-1}$ MeV$^{-1}$) detected (about 0.6 photons enter the detector aperture) is negligible. The integration is started from 1 s before impact and only 1 photon is detected when integrated down to 10 ms before impact. The number of photons detected from the warhead increases as $1/t_{to\ impact}$ as the scout approaches the warhead. Since there is practically no background counts during the observation interval even a few gamma rays detected from the source are significant especially if coincides with the position of the RVs monitored by the radar or infrared tracking system (see FIG. 22).

The 10 ms time before impact is equal to a distance of about 140 m if the scout approaches the warhead at 14 km/s. Therefore, with such speeds the detection range of the SACRED detector is about 100 m. If the RVs are within this distance range during the early deployment, RVs mainly follow the ballistic trajectory of the ICBM bus at early stages, the proposed discrimination technique can be applied.

The proposed technique requires 10 ms to detect, analyze and transmit the information to the ground control or to the interceptors following the scout. This is a short time but with the computer power available it is technically feasible. The information to be transmitted is rather simple as soon as the analysis is complete. It should contain the number of RVs, their position and direction of motion (determined by the onboard radar or infrared tracking system), and the ones that contained the warhead (determined by SACRED). Such information can be transmitted within micro seconds.

The above calculations show that the SACRED detector has potential to carry out discrimination at the early stages of RV deployment. If a larger signal is required then there are two independent ways to increase the signal. The first is to use slower scout interceptor missiles. Speeds down to 1 km/s seems to be possible. This will give up to a factor of three increase in the number of photons in the same time interval before impact but only extend the detection range by about a factor of 2. The second is to increase the sensitivity of SACRED by increasing its area-efficiency factor. Any improvement on the area-efficiency factor will increase the number of gamma rays observed by the same factor. A factor of 5 improvement is possible. If both ways are applied together a factor of 10 increase in the count rates is feasible.

The application discussed here assumes that the RVs are deployed within a short time as shown in FIG. 21. It is possible that RVs can be deployed one by one with a booster which results in RVs separated by many kms. In such a case a different technique may be applied. The scout can approach the first RV in a collision course. If it is a decoy it bypasses it in the direction of the next one. It carries on until it finds the RV that contains a nuclear warhead and kills it. This assumes that RVs deployed by an ICBM bus follows the same ballistic trajectory very closely and large angle maneuvers by the scout are not necessary. If a slow scout with high maneuverability is used then the feasibility of this technique improves.

The above calculations are carried out for head on interception. It is feasible to launch a scout interceptor from a ship or a submarine. In this scenario the scout interceptor is aimed to meet and follow the ICBM bus or the RVs at their mid range. This will allow the scout equipped with a SACRED detector to have much larger observation times in the order of minutes compared to milliseconds for the head on interception. If we assume the observation time to be about 5 minutes and 20 counts are required per RV to detect the warheads with high significance and without ambiguity, then the maximum range of warhead detection is about 5.5 kms. (The same values for the source luminosity and the area-efficiency factor are used.) The diffuse galactic gamma ray background radiation in 5 minutes produces about 1 gamma ray event per 1° by 1° sky bin which is the FWHM angular resolution. Therefore, the minimum signal to noise ratio is about 20. This technique can be effective for exoatmospheric midcourse warhead discrimination if fast deployment of scout interceptors from marine vessels to follow ICBM busses and RVs can be achieved.

Another possible discrimination technique may use a directed energy weapon, particle beam or small scale neutron bomb to irradiate the RVs and discriminate the warheads from the secondary emission they produce such as neutron activation. The number of gamma rays detected from such interactions should be much larger and the discrimination of the warheads can be carried out from distances of the order of 1,000 kms. The estimated gamma ray rate that may be observed from a neutral particle beam irradiated warhead at a range of 1,000 km is 0.1–1 photons $cm^{-2} S^{-1}$. In 1 s 50 to 500 photons with energies reaching up to 10 MeV will be observed from such a interaction. In such a case the SACRED detector can be mounted on a stationary space based platform. Its insensitivity to neutrons, wide field-of-view and imaging capability will enable discrimination and/or kill determination during or a few seconds after the interaction. If gamma ray emission from nuclear warheads is higher than estimated the discrimination feasibility improves significantly.

A warhead can only be definitely killed if its structure breaks up. Therefore during a hit the radioactive material contained spills out. The warhead contains significant amounts of shielding inside and the amount of gamma rays observed outside is reduced significantly when the casing is intact. During a kill a much larger release of gamma rays should be observed which may last for seconds. If a factor of 1,000 increase in the gamma ray flux is assumed then the SACRED detector is expected to detect 100 gamma rays from the warhead killed for a duration of 1 s and at a distance of about 5 kms.

If particle or directed energy beams are used to intercept warheads the kill determination can be carried out from much larger distances. The estimated gamma ray rate observed from a neutral particle beam irradiated warhead at a range of 1,000 km is 0.1–1 photons $cm^{-2} s^{-1}$. This means that the SACRED detector will detect 50 to 500 gamma rays in 1 s and should be able to determine whether the warhead is destroyed. It will even be possible to carry out kill determination by particle beam directed energy weapons during a nuclear precursor blast if the angular separation of the explosion and the warhead to be destroyed is larger than the SACRED angular resolution for a point source. If the precursor blast is relatively close, the detector can be swamped by the large count rate but within few seconds the dead time will normalize and the detector will be sensitive again. The SACRED detector has excellent resistance to radiation and quick recovery from high count rates.

The scout missile carrying a SACRED detector can monitor kills within a few km radius from other interceptors engaging the RVs. If only the kill determination for the intercepted RV is required then only a small SACRED detector mounted on the cone of the interceptor missiles is required. The small imaging SACRED detector will be preferable to non-imaging detectors as it can definitely identify the target and show that the signal observed during the final milliseconds before impact is not due to statistical fluctuation in the background level.

Precursor nuclear blasts can be employed in space before a nuclear attack to disrupt communications and defense mechanisms. It will be important to monitor such explosions from a distance and determine their position, extent and duration. During a blast the number of gamma rays released is extensive. At 1,000 km and 100 s, the gamma ray flux from a one megaton fission yield will be about $10^7$ photons $cm^{-2} s^{-1}$ with energies reaching up to 10 MeV. Such yield shows that a small SACRED detector mounted on a fixed space platform should be able to monitor the precursor blasts from distances exceeding 10,000 kms.

The RORSAT type satellites which carry out active ocean surveillance and carry moderated nuclear reactors do not normally contain shielding and can be monitored easily with a wide aperture small SACRED detector. It could be mounted on a fixed space based platform which will increase its signal to noise ratio dramatically compared to balloon borne detectors. Therefore, the application for both the precursor blast and nuclear powered satellite monitoring can be carried by the same small SACRED detector.

Covert satellites that carry nuclear warheads can be placed into orbit. If the warheads in such satellites have similar gamma ray emission as missile based warheads they could be observed by the SACRED detector at tens of km away in time scales of hours. For full identification a statistically significant amount of photons must be observed and the energy spectrum generated. This will require more time or closer approach to the suspect satellite. An energy spectrum of 10,000 photons can be obtained within about one hr from a distance of 1 km. The higher energy photons above 1 MeV with the characteristic nuclear lines can be used as the signal for final identification.

Energy Resolution The energy resolution of a gamma ray photopeak depends upon the electrical noise, the light collection efficiency and the intensity spread of the collected light. The results show that the electrical noise contributes a small amount to the full width at half maximum (FWHM) resolution of the photopeak. With the measurement conditions outlined above, for the bare photodiode measurements of the $^{241}$Am photopeak, a typical FWHM was 20 channels. This width is completely governed by the electrical noise, including charge collection ability, and is consistent for all other peaks which occur at different channel numbers: for example, the $^{57}$Co peak at 121.9 keV will appear near channel 1,000 for the identical gain settings used to take the 60 keV $^{241}$Am photopeak. The FWHM is the same for both.

Figure 25:
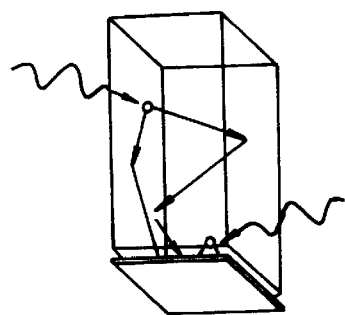
FIG. 25 is an illustration of the light collection from a CsI(Tl) crystal for incident gamma ray photons.

When a scintillator is mounted onto a photodiode, the photopeak width increases. The effect of the light collection efficiency from the scintillator results in a much broader peak than with a bare photodiode. For example, as shown above in FIG. 25, efficiency of light collection from a pulse close to the photodiode surface, near the center of the scintillator, may be significantly different from the collection efficiency when the pulse is from a skewed location. A measured photopeak will be a convolution of all these results of varying pulse locations. The result is a wide peak. Typical FWHM values even with low electrical noise are about 45 channels. This makes an interesting point. Since both sources of "noise" are independent of each other, the half width at half maximum (HWHM) a can be written as $$\sigma_{Total}^2 = \sigma_{Opt}^2 + \sigma_{Elec}^2$$

where $\sigma_{Total}$ is the total measured half-width, $\sigma_{Elec}$ is the half-width contribution due to electrical noise and $\sigma_{Opt}$ is the spread due to the scintillator/photodiode geometry. Since the electrical part and the total part are known from measurements, the optical component can be estimated to be $\sigma_{Opt}^2 = \sigma_{Total}^2 - \sigma_{Elec}^2$. Then a typical value for a 1.0×1.0× 1.75 $cm^3$ CsI(Tl) crystal is $2\sigma_{Opt}=40$. This means that the spread in the photopeak has very little to do with the electrical noise performance of the photodiode. That is, with these numbers, it makes little difference if the photodiode noise FWHM is 20 or 22 channels (10% noisier); the total photopeak width would only increase from 45 to 46 channels, causing the resolution to go from 5% to 5.1%. It also points out that any effort to reduce noise by lowering the temperature will only be beneficial if the noise is reduced by a large fraction. The best approach to increasing resolution is to try to understand the optical part of the problem, namely the physical reasons that limit light collection.

Silicon Detector Modular Design

Figure 26:
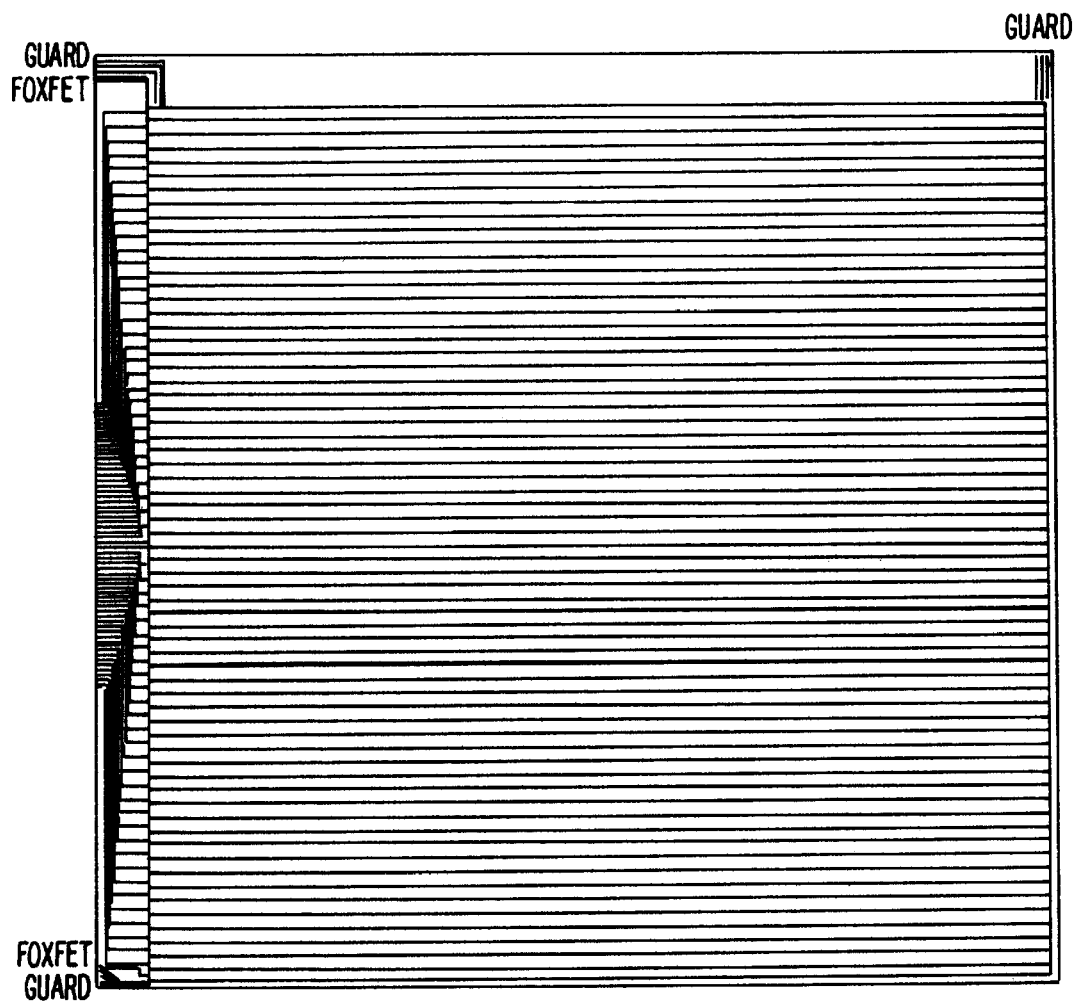
FIG. 26 is an illustration of an individual silicon strip detector design (the back side is the same as the front side but rotated by 90°)
Figure 27:
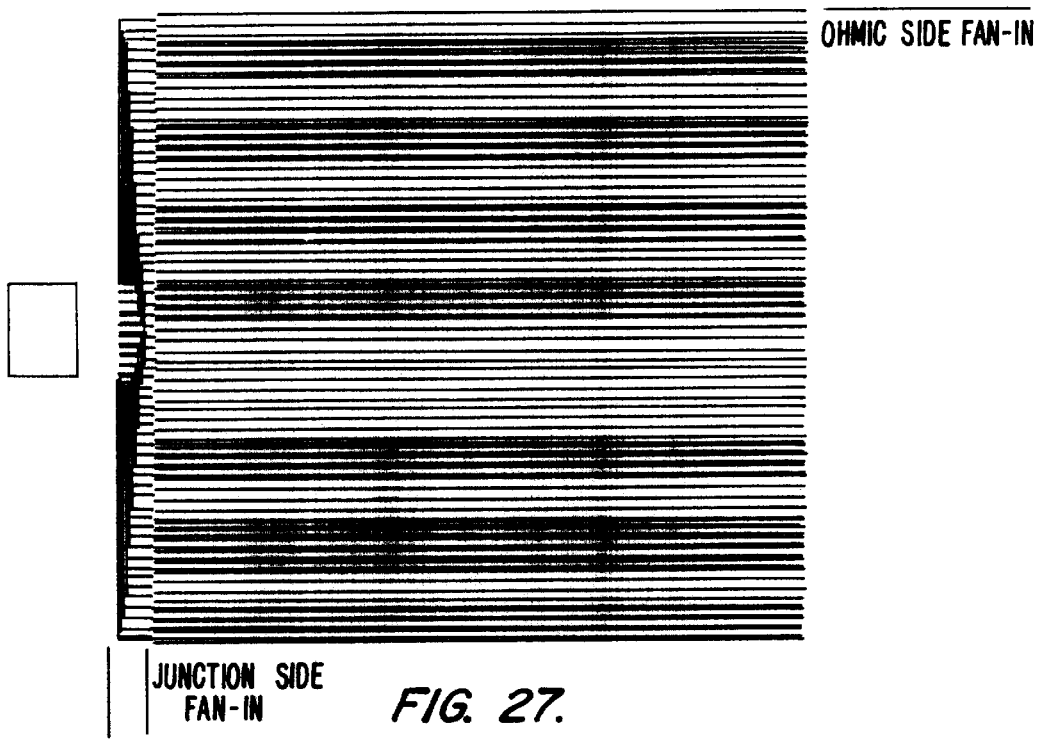
FIG. 27 is an illustration of the interface between the silicon micro-strip detector and the FEE chip/ceramic carrier combination.
Figure 28:
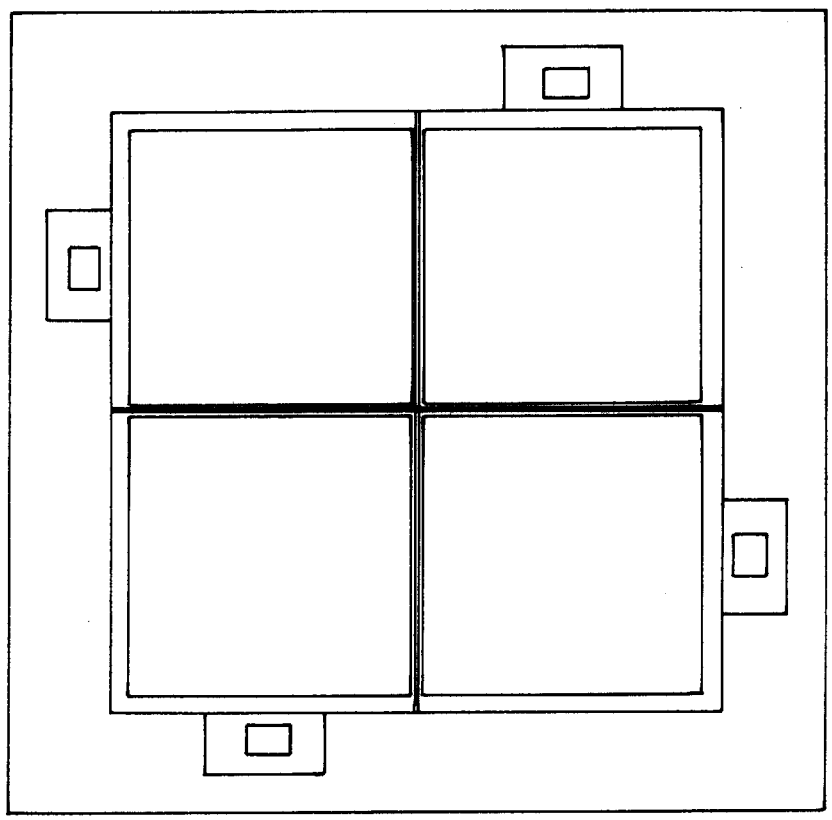
FIG. 28 is an illustration of a silicon micro-strip detector module which includes the four silicon strip detectors, the PC board, and eight FEE chips (four on each side) mounted on a ceramic chip carrier.

The schematic details of one embodiment of the individual silicon microstrip detectors of the present invention are shown in FIGS. 26–28. The design includes 64 pad output on both junction and ohmic sides, fanned in to 250×250 micron$^2$ linear pad array. Fan-in connection dimensions should be minimized, but certainly not to compromise performance. As viewed from one side, the opposite side is an exact copy, rotated once by 90°.

The actual silicon is exactly square so that it may be rotated and used in the three other locations on the detector module board. The number of guard rings are preferably set to 3, although the pad placement may work best if the guard ring pads are located toward the outside, so they are neighbors when the silicon is rotated.

The FEE chip is preferably mounted onto a ceramic carrier, along with the buffer electronics. The silicon strip detector output pads (see FIG. 26) are bonded to 64 input pads on the PC board (see FIG. 28) that support both the silicon strip detectors and the FEE chips. The ceramic FEE chip carrier is bonded onto the PC board pads. The FEE chip is bonded to the pads on the ceramic carrier. More detectors may be placed onto a PC board and connected to readout electronics ASIC chips to achieve large effective areas. The strips may also be daisy chained to decrease the number of readout electronics chips needed.

This technique will allow the fabrication of extremely fine fan-in with about 50 micron pitch required at the detector input side on the ceramic carrier. Such high resolution traces cannot be made easily on a PC board. However, it can be built on a ceramic substrate. The ceramic carrier can also be used for testing the FEE chips so that only the working chips will be mounted onto the detector modules, since it will be especially difficult to repair or replace bad chips once they are bonded onto the detector modules.

Figure 29:
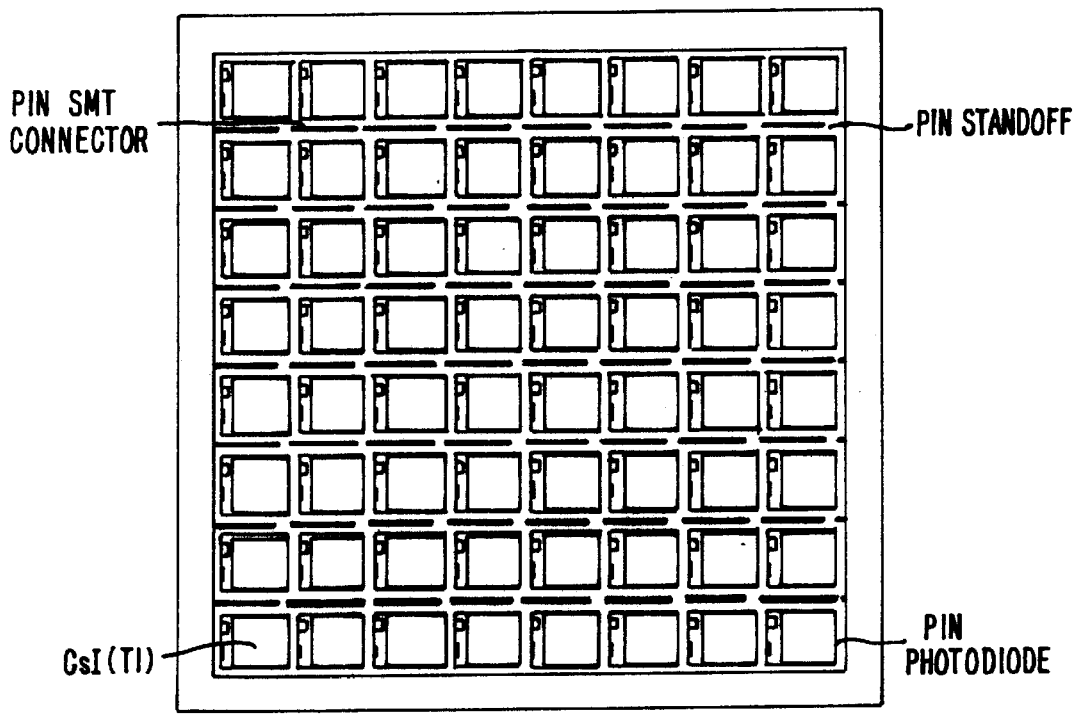
FIG. 29 is an illustration of a top view of a CsI(Tl)/photodiode calorimeter module design in which the 64 CsI(Tl)/photodiode arrays are surface-mounted on the PC board and the FEENA chip and the other analog components are mounted on the other side of the board.
Figure 30:
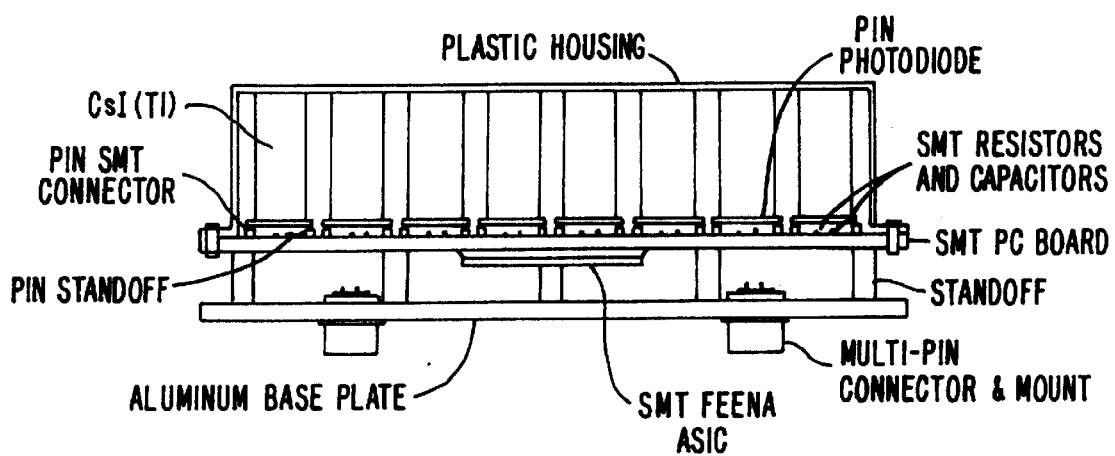
FIG. 30 is an illustration of a side view of the design illustrated in FIG. 29.

FIGS. 29–30 illustrate an embodiment of the invention utilizing surface mount technology (SMT) to mount the photodiode by surface mount connectors on one side of the board. This configuration is beneficial since it is desirable to minimize the length of the connections between the photodiode and the FEENA chip to lower electronic noise and therefore it is appropriate to mount the FEENA chip and the diode array on the same electronics board. Due to the density of diode pins, the through-hole design cannot allow the FEENA chip to be mounted on the other side of the board, thus making SMT useful.

As shown in FIGS. 29–30, the diode array is elevated from the board by the SMT connectors and standoffs which allow the surface mount GigaOhm bias resistors and the coupling capacitors to be mounted underneath the diode. The other side of the board is used to mount the FEENA chip, the other analog components and the by-pass filter network. As shown in FIGS. 29–30, a plastic housing is placed on the calorimeter printed circuit board to protect the CsI(Tl)/photodiode array from mechanical and humidity damage. This housing allows the heat generated by the electronics on the other side of the printed circuit board to easily dissipate away from the other side of the board. This overcomes the shortcomings of a closed module in which the heat enclosed inside the module may raise the temperature and degrade the electronics performance. In this approach, an individual cooling system for each calorimeter module may not be necessary. The whole silicon hodoscope and CsI(Tl) calorimeter will be sealed as a unit.

Figure 31:
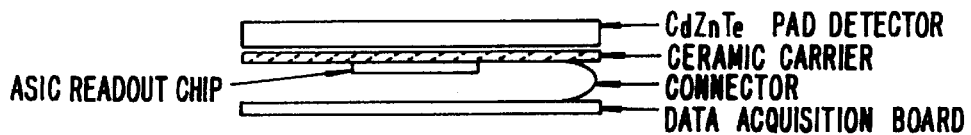
FIG. 31 is an illustration of the side view of an embodiment of a single module of a two dimensional detector module.
Figure 32:
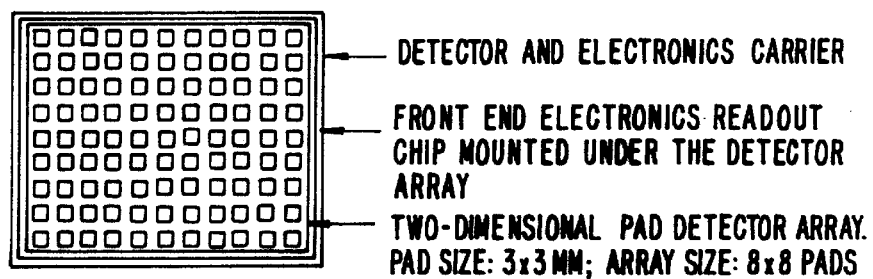
FIG. 32 is an illustration of the top view of the detector module illustrated in FIG. 31.

This design can also be applied to all other kinds of position sensitive solid state detectors such as CdTe, CdZnTe, HgI$_2$, HPGe, etc. The position sensitive detector modules (FIGS. 29–30) can be made by mounting individual units on the detector module as shown in FIGS. 29–30, or the detector itself can be position sensitive (single or two dimensional array of pads or pixels) and one or more of these detectors can be mounted together onto the calorimeter module board. Although a two dimensional 8×8 array is indicated here, the pixel dimensions can be in any size or form. A possible two dimensional (8×8) combination of a CdZnTe Pad detector is shown in FIGS. 31–32. These detectors can also be made with negligible dead perimeter area so that they can be abutted to form uniform large area two-dimensional arrays. The specifications of such a detector are given in Tables I and II.

TABLE I

CdZnTe Pad Detector Array Performance Specifications

| | |
|---|---|
| Field-of-view: | Approximately 20 × 20 cm (8" × 8") |
| Pixel size (step): | 0.1 × 0.1 to 5 × 5 mm |
| Insulated space between pixels: | 0.01 to 0.2 mm |
| Crystal thickness: | 1 mm or 10 mm |
| Energy resolution: | ≦5% @ 60 keV (≦4% @ 140 keV) |
| Percent of counts in ± 5% window: | 90% |
| Maximum count rate: | 1 kCounts/sec to 1,000 kCounts/sec |
| Flood field uniformity: | <4% |
| Energy range: | 60–511 keV |

TABLE II

CdZnTe Pad Detector Array Readout Specifications

| | |
|---|---|
| Accuracy: | X, Y position of interaction ≧ 6 bit Energy range ≧ 10 bit |
| Output: | Serial (parallel is possible.) |

Nondestructive Advanced Detector for Inspection Application (NADIA)

The most probable interaction mechanism for 300 to 2,000 keV x-rays is the Compton scatter process. Therefore, the detection of gamma rays in this energy range must use Compton interaction to have maximum sensitivity. The detector must also have excellent angular and energy resolution and a wide field-of-view. The best detection technique that has all these features is the Compton double scatter method. This technique incorporates Compton scattering and photoelectric absorption.

A strong x-ray source is required for realtime inspection of munition items with 2-dimensional imaging. Some sections of the NADIA detector will be in the direct x-ray beam path. This requires a detection system with high resistance to radiation damage. The present x-ray inspection systems using scintillators suffer degradation from radiation damage.

The NADIA detector only has the active area of the silicon microstrip hodoscope in the direct path of the x-ray beam. Therefore, it is only important to assess the resistance of the silicon micro strip detectors for radiation damage to find out if the proposed system is feasible. The radiation damage to silicon microstrip detectors have been investigated by several authors in recent years. These studies are mainly interested in the application of silicon microstrip detectors for the Superconducting Super Collider (SSC)

experiments. The SSC design luminosity is $10^{33}$ cm$^{-2}$s$^{-1}$ which will produce about $10^{14}$ cm$^{-2}$ charged particles, an equal number of gamma rays with average photon energy of about 250 MeV, and a few times $10^{13}$ cm$^{-2}$ neutrons in silicon strip tracking detector at an inner radius of 15 cm in ten years of operation time. The electronics associated with the SSC detector elements will be mounted either directly on those elements or will be an integral part of them and will also be subject to the same high radiation dose. Therefore, the vertex detectors and front end electronics at the SSC must have exceptionally high radiation resistance. The SSC is expected to run at 20 TeV per colliding beam which will produce very high energy secondary particles.

The damage to silicon microstrip detectors is mainly due to the displacement of silicon atoms from their lattice positions in clusters or singly. This process needs energetic particles, especially high energy protons and neutrons. The damage due the displaced silicon atoms can cause several effects. The main effect is the increase in the leakage current from a generation of carriers through defect levels in the band gap. Displacement damage leads to the creation of positively charged acceptor sites throughout the bulk of a silicon detector. That process changes the effective dopant concentration in the silicon. For the radiation doses expected at the SSC, the effect only impacts the lightly doped (~$10^{12}$ cm$^{-3}$) bulk depletion region which comprises the sensitive volume of the detector. The heavily doped (~$10^{18}$ cm$^{-3}$) contact regions are essentially unaffected by the acceptor creation. The lightly doped n-type material of which most detectors are made, is slowly turned into fully compensated material, as the newly created acceptor sites effectively neutralize the donor sites in the original n-type material. Slowly the material turns into p-type and as the doping increases the resistivity starts to drop. The decrease in resistivity translates directly into an increase in the voltage needed to deplete the detector. That eventually leads to depletion voltages which create local electric field strengths greater than can be maintained in silicon, resulting in the breakdown of the detector or forced into a mode where it operates without full depletion.

Other effects include carrier trapping by defects which removes carriers from the energy signal for periods longer than the electronic processing time and even longer term trapping which results in an effective increase in material resistivity by removing majority carriers. Carrier trapping mainly affects spectrometers and carrier removal leading to resistivity variations has been only observed in silicon microstrip detectors at extremely high charged particle doses.

The radiation environment for the proposed x-ray inspection of the munition items is quite different than the SSC background. Only x-rays of 300 keV to 2 MeV energies will be used with the NADIA detector compared to charged particles of hundreds of MeV, fast neutrons and high energy gamma rays at SSC. Even if the proposed detector is extended for gamma ray energies up to 10 MeV still the energies involved are low compared to the SSC background. Therefore, the radiation damage from x-rays of 300 keV to 2 MeV energies should be significantly less than the damage caused by the high energy particles. This is because the x-rays do not have as much power as the high energy particles to dislocate silicon atoms. The amount of damage caused by x-rays of 300 keV to 2 MeV is not considered significant for the SSC environment. However, the results of the SSC studies on radiation damage to silicon are relevant to understand what might be expected in the worst case scenario for the proposed detector.

The radiation damage studies carried out for silicon strip detectors show a relation which relates the leakage current density J to the fluence $\theta$, $$J = \alpha\theta + J_0$$

where $J_0$ is the initial leakage current density, J is the leakage current density after radiation treatment, $\theta$ is the fluence in particles/cm$^2$ and $\alpha$ is the leakage current damage constant. The value for $\alpha$ has been determined to be about $(4.8\pm0.5) \times 10^{-17}$ A/cm for 800 MeV protons and to be about $6.6\times10^{-17}$ A/cm for fast neutrons at room temperature. A test with penetrating beta rays shows the irradiation needed to reach SSC background radiation for 10 years integration time ($9.8\times10^{13}$ neutrons/cm$^2$ or $14\times10^{13}$ protons/cm$^2$) showed a pulse height degradation of about 15% and depletion voltage increased by a factor of 4 but reduced by a factor of 2 after 20 day annealing. After such high doses of radiation the silicon microstrip detectors were still usable.

A fluence of $10^{14}$ particles/cm$^2$ in 10 years corresponds to an isotropic source of about $4\times10^{11}$ particles/s if the detector is placed at 1 m from the source. This is equivalent to a 10 Ci radioactive source of high energy particles. Therefore, the proposed silicon microstrip detectors should be able to work without appreciable degradation for 10 continuous years with a 10 Ci isotropic x-ray source placed at 1 m from the detector. This is an extremely large radiation dose level and much lower strength x-ray sources will be normally used in the inspection of the munition items. This does not take into account significantly lower damage expected from x-rays compared to high energy particles such as protons and neutrons. The radiation damage to the proposed detector by x-ray and gamma ray sources of required strength is expected to be negligible.

The radiation damage to front end electronics required for the readout of the silicon microstrip detectors is not important as these chips will be placed at the perimeter of the hodoscope which will be effectively shielded in the preferred design. The shielding of the front end electronics is not absolutely essential as radiation hard electronic circuits are manufactured with excellent results. Some of these devices were tested for use in the SSC experiments. The radiation fluences of $10^{14}$ protons/cm$^2$ (2.7 MRad) was applied to bipolar and CMOS processes. The current gain, $\beta$, of the transistors changed by only about 10% for the bipolar process. The shift in the threshold voltage $V_{th}$, i.e., the gate voltage at which the CMOS transistor turns on changed by about −0.2 V for p-type and by about −0.1 V for the n-type. These results show that the front-end electronics for silicon microstrip detectors should be able to stand the SSC environment for 10 years of exposure. The proposed detector should have much lower radiation damage to front end electronics than from the SSC environment because it uses x-rays at much lower energies. Therefore, the degradation expected for the front-end electronics should be negligible for a 10 year life time of the prototype detector.

Another important advantage of silicon microstrip detectors is that they do not need high voltages or cooling to low temperatures. Room temperature functionality is important to produce small size, low cost and low power detectors. However, if higher energy resolution is required for special applications it could be achieved by modest reduction in the temperature using thermoelectric coolers such as Peltier devices.

The silicon microstrip detectors have a strong potential for mass production. Significant number of wafers are needed to achieve conversion rates required for high sensitivity. Their small thicknesses and ultrasonic wire bonding capability render them good candidates for compact PC mounting with data acquisition IC's placed next to them. The readout IC's can be designed to give a fast trigger signal when events occur and output the address and the analog content of the channel that have data.

The proposed new nondestructive inspection (NDI) technique is exceptionally versatile. It can be applied in many configurations, for many different test object sizes, materials and shapes, and a variety of x-ray sources with a wide range of energies. Several different embodiment are disclosed.

One embodiment of the device is a low energy (~300 keV) small object imager (SOI). This type of NDI detector is built using only the silicon microstrip hodoscope. The hodoscope dimensions can be between 4 cm×4 cm to 12 cm×12 cm with 0.5 to 1 mm thick silicon wafers. The total silicon thickness can be 2 to 10 cm with Compton scatter probability ranging from 45 to 95% for 300 keV x-rays. Pixel sizes can be as low as 25 m×25 m for super high resolution imaging. The object size must be at most equal to the detector area. Otherwise it will image a section of the object. This detector can be used with both energy and angular discrimination of the scattered photon background. In the single scatter mode it will accumulate all events without any cut. In the double scatter mode it will measure the total energy deposited in the hodoscope from multiple Compton scatters ending most likely with photo absorption. The direction of the incident photon can also be determined from the energies deposited at each interaction point and the pixel coordinates of the first and the last scatters. This detector is expected to have excellent energy and angular resolution as there is no calorimeter limitation. It can be used with both monoenergetic and continuous energy x-ray sources.

Figure 33:
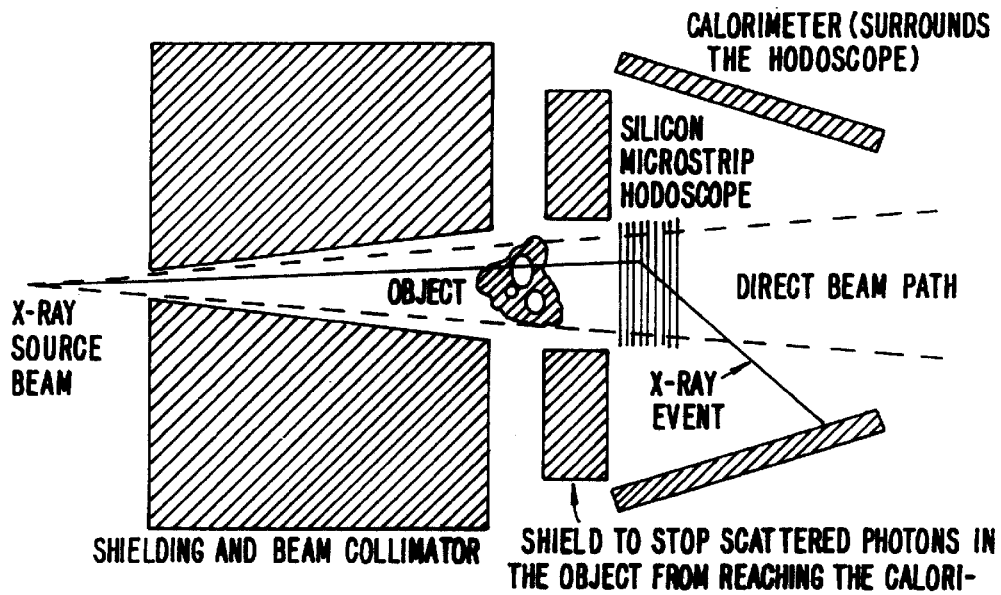
FIG. 33 is an illustration of an embodiment of the NADIA detector layout in which the calorimeter surrounds the hodoscope on all four sides.

Another embodiment of the invention applicable to large objects and higher energy x-ray sources is an object imager for a monoenergetic x-ray source (OIM). In this embodiment an NDI system built from a silicon microstrip hodoscope, only, is feasible. Such a detector with large area and many detector planes will be costly. A more practical solution would be a detector with a calorimeter placed behind the collimating shield as shown in FIG. 33.

The illustrated design shows the collimated x-ray beam incident on the object under inspection. The collimating shield is not necessary if the x-ray beam is already collimated to the size of the hodoscope. The hodoscope will be in the direct path of the incident x-ray beam. The collimator will be designed as a shield for the calorimeter and the hodoscope electronics if required. The calorimeter surrounds the silicon microstrip hodoscope on the sides. The unscattered x-ray photon makes a Compton scatter in one of the silicon microstrip hodoscope planes and stops in the calorimeter as shown in FIG. 33. Whether or not a detected photon from a monoenergetic source is scattered in the test object will be determined by the total energy of the photon deposited in the detector. The elimination of the photons scattered in the test object significantly decreases background and enhances the signal-to-noise ratio. The calorimeter can also be shielded from the background photons scattered in the test object by placing a separate shield between the testy object and the calorimeter. This will help reduce the calorimeter count rates.

The calorimeter scintillator normally has a worse energy resolution than the silicon microstrip hodoscope resulting in a lower angular resolution for the whole detector. The loss in the energy and angular resolution is balanced by the lower cost of the NDI system.

In this application monoenergetic sources from 300 to 2,000 keV such as $Cs^{137}$ and $Co^{60}$ can be used. Energy cuts within the detector energy resolution are sufficient to eliminate much of the scattered photon background. This embodiment will not, however, have the functionality of the full detector described below and cannot be used effectively with continuous energy x-ray sources.

A fully functional detector, similar to that illustrated in FIG. 33, can be used with both the monoenergetic and continuous energy sources (300 to 2,000 keV) for medium to large size test objects. In this embodiment the calorimeter must be position sensitive to enable the determination of the incident photon direction. To achieve sufficiently good direction determination the hodoscope pixel size should be $\leq 1$ mm$^2$ and the calorimeter $\leq 1$ cm$^2$. The hodoscope will be similar to but have larger area than the SOI. The calorimeter should absorb Compton scattered photons with about 90% efficiency.

Figure 34:
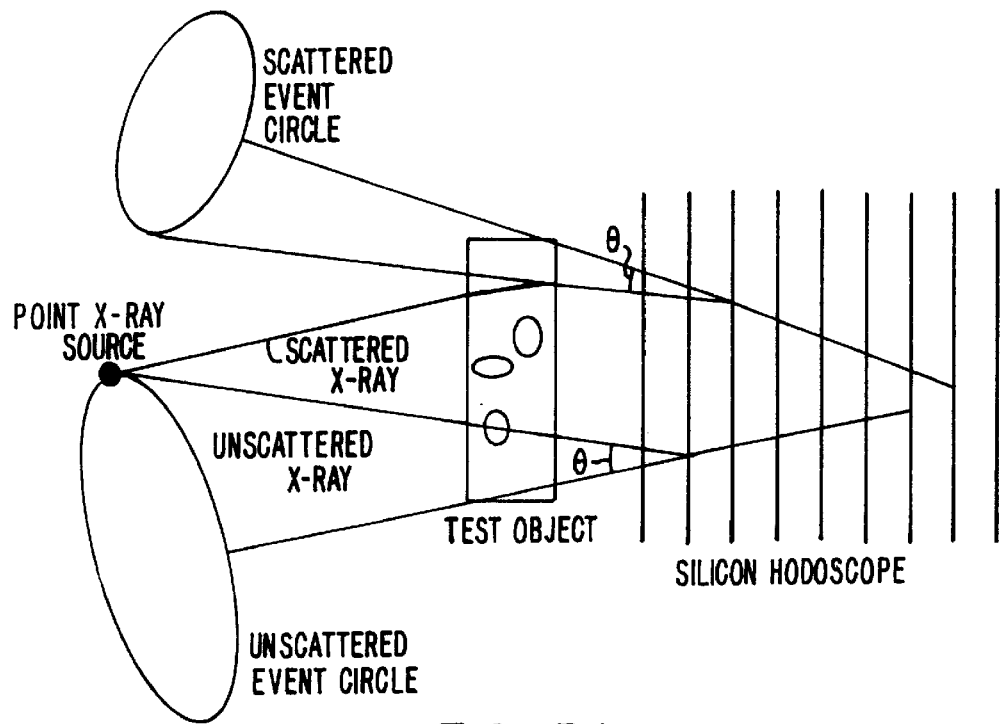
FIG. 34 is an illustration of the scattered photon background discrimination using the incident photon direction measurement, a method especially useful for a continuous x-ray source.

In this embodiment the scattered photon background is eliminated by measuring the incident photon direction. FIG. 34 demonstrates the method of discrimination of the scattered photon background. The figure shows one photon scattered in the test object and the other not. The Compton scatter angle is calculated using the formula given above from the energies deposited in the two interaction points (assuming that the photon is totally absorbed in the second scatterer). The scattered photon vector is determined from the coordinates of the first two interaction point pixels in the hodoscope. The event ring determined for the unscattered event passes through the known x-ray source direction and the event ring for the scattered event does not.

Depending on the energy resolution and the geometry of the two pixels some of the event rings from scattered photon background may overlap the point source direction. Higher energy and geometric resolution improves scattered photon background. A much more significant improvement can be made if the first recoil electron is tracked through the hodoscope. This will limit the event ring to an arc and the chance probability of a scattered photon arc with the x-ray source direction diminishes dramatically.

Another embodiment of the invention is an energy resolved tomography imager (ERTI) for use with a continuous x-ray source. In addition to background discrimination using the incident photon direction measurement for a continuous energy x-ray source the energies of the unscattered photons are determined. The energy spectrum for each image pixel can be measured that leads to energy resolved tomography imaging (ERTI) system if the test object or detector is rotated. This is new information never before available. This system can also produce two dimensional images with energy spectrum information.

The Compton scatter depends strongly on the electron content of the material the x-ray beam traverses. Therefore, the energy spectrum obtained for each pixel represents, with inverse proportionality, the electron content in the test object along that path. The different energy spectra can be represented by different colors. The intensity can now be shown as brightness of that color. This is the natural observation of the human eye. ERTI has the potential to bring a new dimension to the realtime inspection of munitions and other objects or materials. It can also be used in medical imaging and radiography.

Figure 35:
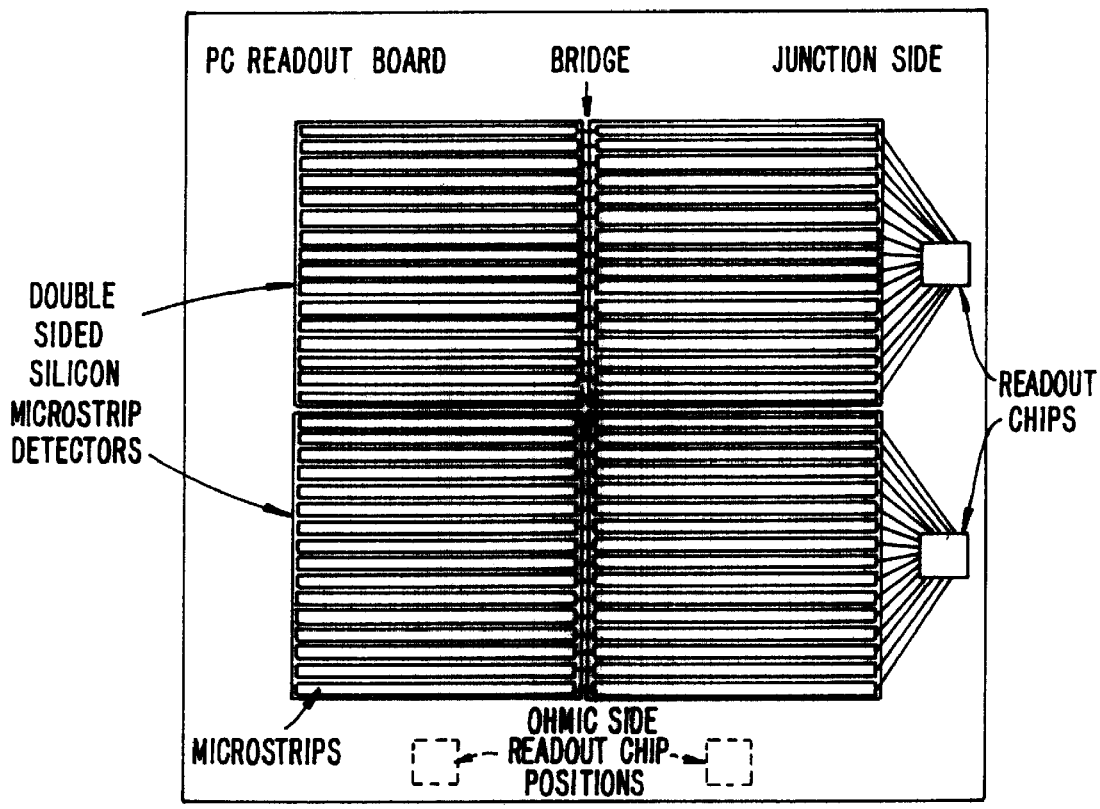
FIG. 35 is a top view of a hodoscope detector plane which includes four bridged double sided silicon microstrip detectors surrounded by the front end readout electronics PC board.

The thickness of the silicon microstrip detectors is between 300 to 1,000 microns. Double sided configuration can be used with approximately 1 mm pitch strips orthogonal to each other on both sides. Each detector will be made from square silicon wafers with minimum areas of 5 cm×5 cm. Four detectors will be bridged together to form a square plane of 10 cm×10 cm as shown in FIG. 35 surrounded by the front end readout electronics. The hodoscope will contain 20 to 25 detector planes. The hodoscope area can be increased by using larger silicon wafers, for example 6.4 cm×6.4 cm wafers. Several silicon microstrip detectors can be connected together by bridging the parallel strips in series (FIG. 35). Bridging microstrips decreases the readout channel number and related electronics significantly. The preferred detector bridging can save about a factor of 2 in readout channels and electronics. However, bridging also increases the data rate by a factor of two. If data rates in bridged silicon microstrip wafers becomes a problem bridging may not be carried out. The readout chips are mounted as near as possible to the silicon detectors to minimize the front end PC readout board size. The fan-in from strips to the readout chip pins are gold plated for good quality ultrasonic bonding. FIG. 35 shows the Junction side. The ohmic side (back side) strips runs orthogonal to the junction side so that both x and y dimensions of an interaction in the silicon is measured simultaneously. The bridging on the ohmic side is similar to the junction side. The position of the readout chips for the ohmic side will probably be mounted on the reverse side. The output and control signals for the readout chips are not shown as they depend on the chip design. The readout chips will be placed on all sides if the strips are not bridged.

The calorimeter is made from CsI(Tl) crystals viewed by photodiodes. The CsI(Tl) has been found to be the most cost effective solution for the calorimeter. However, the calorimeter can also be built from NaI(Tl) crystals or any other high density scintillator with fast decay time. The calorimeter surrounds the sides of the hodoscope. The amount of area covered is primarily driven by cost.

The calorimeter is position sensitive using CsI(Tl) crystals with 1 cm×1 cm to 2.5 cm×2.5 cm rectangular bars with length varying from 1.5 cm to 2.5 cm. The wide variation of length is due to the energy range of detection. The bottom section of the calorimeter needs longer crystals because the forward scattered gamma rays carry most of the primary photon energy. The extra thickness stops the higher energy forward scattered gamma rays. The CsI(Tl) crystals on the top side of the calorimeter can be short, as the photons with large Compton scatter angles carry a smaller fraction of the primary photon energy. The above technique uses a mosaic of individual CsI(Tl) crystals for the calorimeter. Each crystal has to be individually viewed by a photodiode; so as many photodiodes as crystals are required.

Figure 36:
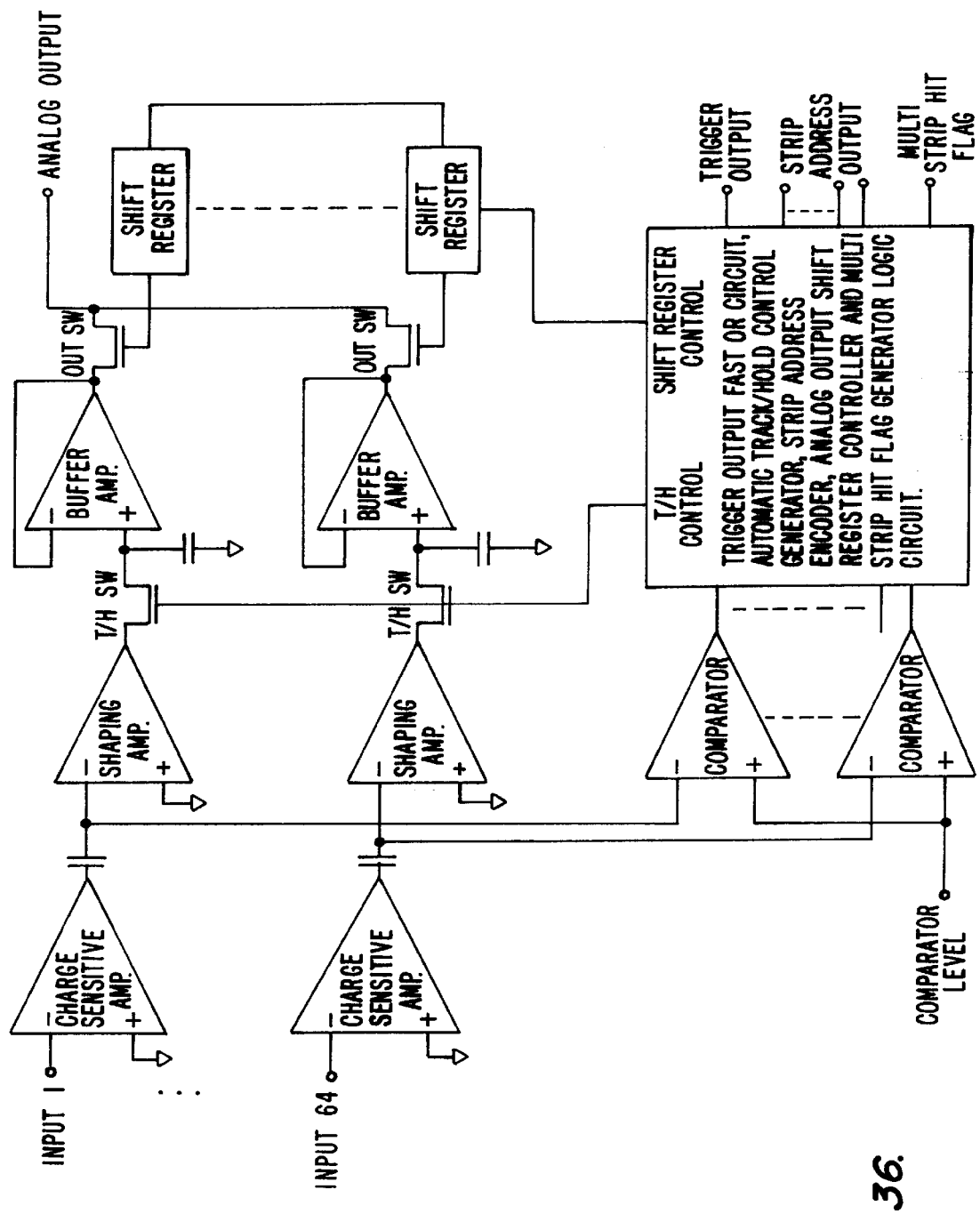
FIG. 36 is a schematic diagram of a possible 32 or 64 channel silion microstrip detector readout chip with fast data readout and trigger output capability.

The design of the data acquisition system is related to the front end electronics of the silicon microstrip hodoscope and the calorimeter. A schematic block design for the data acquisition electronics system is illustrated in FIG. 36 that will apply in general for most kinds of front end electronics. The important factor of the data acquisition system electronics will be fast readout.

The most important part of the front end electronics for the silicon microstrip hodoscope is the microstrip readout chip. The Amplex chip is an excellent low noise, high gain, easy to interface device. However, it does not have a trigger output capability. This problem may be solved by using the trigger from a plastic scintillator placed behind the silicon microstrip detector planes. The signal generated by the calorimeter can be used as the trigger to readout the silicon microstrip hodoscope. However, this is not an elegant solution since the calorimeter will have background triggers that are not coming from the Compton scattered photons. This will produce false readouts of the hodoscope and increase dead time. The legitimate events could be selected by software, but would increase the computation time. The best solution is to design a fast front end readout chip with a trigger output capability. This is not complicated as comparators can be incorporated into the readout chip to detect a strong signal above the externally set threshold and the outputs of the comparators can be fanned in using a fast OR circuit to produce the single trigger output. FIG. 36 shows a possible microstrip readout chip diagram based on the Amplex chip with the trigger output capability using comparators.

The circuit will have 16, 32 or 64 inputs with each input from the microstrip detector AC coupled to a charge sensitive amplifiers. The outputs of the charge sensitive amplifier are connected to a shaper amplifier with a time constant of about 100 to 200 ns. The output of the shaper amplifier goes into the track and hold (T/H) switch. The T/H switch can be controlled externally or activated internally from the trigger output with a delay set to turn the hold on at the peak of the shaped pulse. The T/H switch is connected to the input of the buffer amplifier through the voltage following capacitor. When the T/H switch is open the voltage on the capacitor is held constant and the voltage level is buffered on to the analog output switch. A shift register connects each buffer output to the single analog output pin in sequence, from input 1 to N, by an external clock input. The shift register also has an external clear input to reset it and a clock output to daisy chain it to other readout chips. Only one clock input is sufficient if the clock outputs are connected in serial to the clock inputs of the adjacent readout chips. The charge sensitive amplifier outputs can be fanned out to comparators with a common external level adjustment. The outputs of the comparators can be fanned in through a fast OR circuit which will produce a trigger signal if any comparator input exceeds the set threshold. The trigger signal can also be used with a suitable delay to control the T/H switches to apply hold signal at the peak of the pulse from the shaper amplifier.

The data acquisition speed of the readout chip will also be increased using the extra versatility introduced by the comparators. The design shown in FIG. 36 does not tell which strip has the information so all strips are readout to find the strip that has the signal. A logic circuit can be added to the design which would detect the channel with the largest signal from the comparator outputs, apply a track and hold signal and connect the strip with the signal to the analog output pin. At the same time it can encode the address of the strip that has the information and output it as the address of the strip with the signal. There could be an occasional signal on more than one strip. Multi-hits could be detected and an output could be generated to warn of a multi-hit signal. The trigger signals are generated for each readout chip. They have to be externally processed for the hodoscope in coincidence with the calorimeter to produce the single trigger signal to activate the data acquisition system. For extremely high signal rates this may not be possible. In such a case each wafer or front end readout chip can be separately readout in parallel by their own data acquisition electronics and tagging each event time by using an accurate clock. The calorimeter crystals will also be individually readout and event times tagged by the same clock. The calorimeter will be running at much slower speed, therefore, individual readout modules are not necessary and could be readout in groups.

The data readout can be carried out in parallel and can be stored on-board memory of individual modules. This will be the key to achieve fast data throughput rates. The data can be asynchronously accessed by the host computer, analyzed and displayed on screen in real time. Data acquisition rates of 1 to 10 MHz per readout chip (or silicon wafer) are achievable. Given a data rate of 100 KHz to 1 MHz a maximum of $2 \times 10^9$ photons $cm^{-2}$ $s^{-1}$ x-ray source (unattenuated at the hodoscope) with 662 keV energy can be utilized assuming 1 mm thick silicon wafers with 5 cm×5 cm area which have about 2% Compton scatter probability and a factor of 100 photon attenuation at the test object. This allows 100,000 events to be accumulated in 1 s per image pixel of 1 $mm^2$ area and 25 hodoscope planes at a maximum readout rate of 10 MHz. At a 1 MHz data acquisition rate 10,000 events per pixel will be accumulated. Therefore, sufficient statistics for real time imaging of munitions can be obtained in seconds.

A penetrometer 1/50th the thickness t of the object with three holes of t, 2t and 4t radius is normally used to test the image resolution. If we assume a 4" thick steel test object the penetrometer thickness will be 2 mm. If such a test object is imaged with a small 2 mm thick penetrometer placed in front using a NADIA detector with 10 detector planes, and each counting at 1 MHz, the smallest hole (3.14 $mm^2$ area) will produce 314 counts at each silicon plane and 281 for background. If all 10 silicon planes are combined the signal (difference) will be 330 and the background 2,810, resulting in a signal of 6.2 σ significance for 1 sec imaging time. This is a strong signal for a short observation. (An attenuation coefficient of 0.55 $cm^{-1}$ is used for steel for 662 keV x-rays.)

Figure 37:
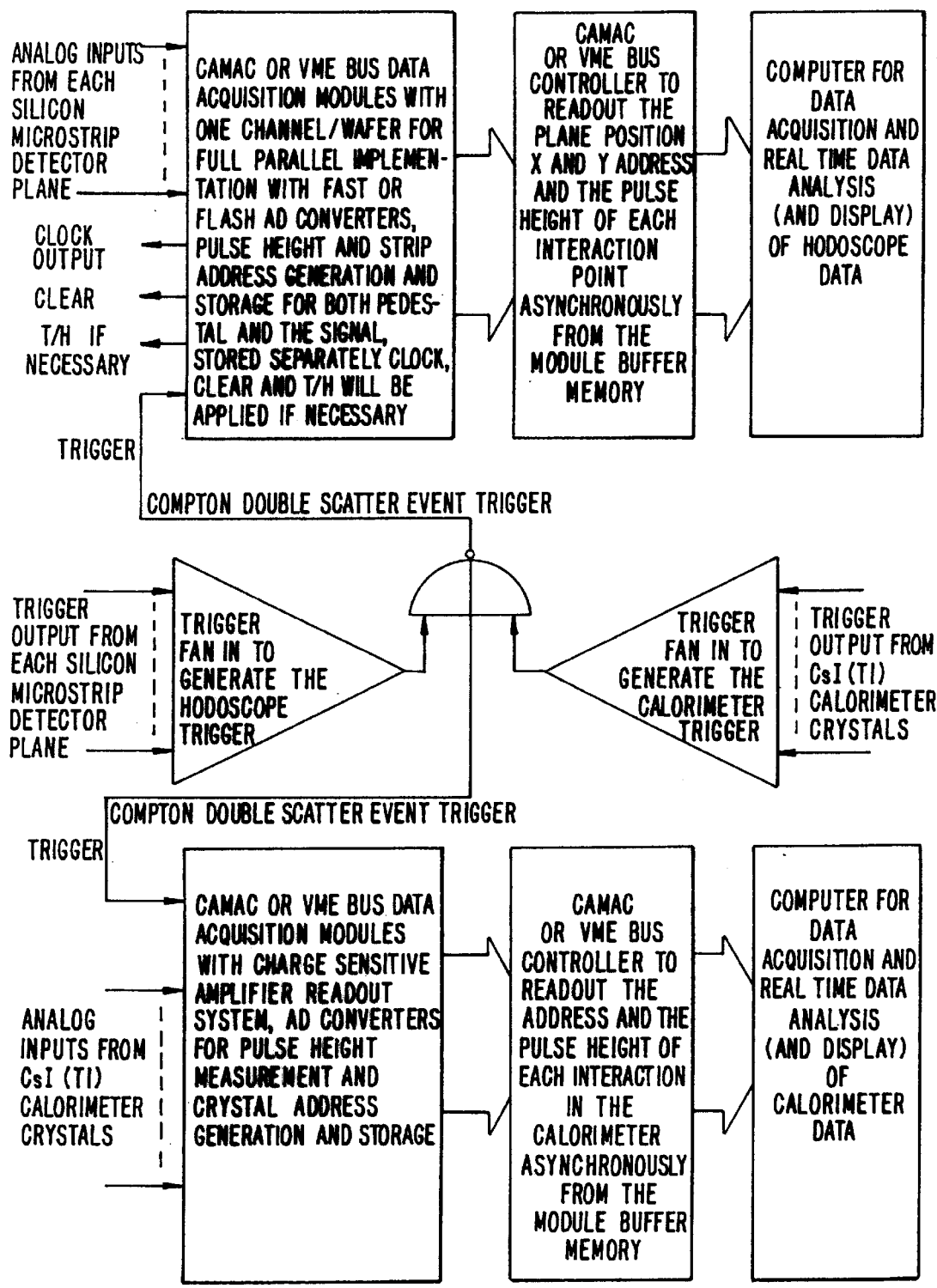
FIG. 37 is a block diagram of a real time data acquisition system for a NADIA detector.

A block diagram of the readout electronics system is shown in FIG. 37. The electronics has two similar sections for the hodoscope and the calorimeter readout. A true event is a coincidence between the hodoscope and the calorimeter. The two master trigger signals from the hodoscope and the calorimeter are sent to a coincidence unit to create the Compton double scatter event trigger. The Compton double scatter trigger signal is only generated if there is a master trigger signal from both the hodoscope and the calorimeter. This is the arrangement which does not employ the time tagged data readout method. Time tagged data acquisition will only be used if absolutely necessary.

The Compton double scatter event trigger activates data acquisition for both the hodoscope and the calorimeter simultaneously. Either CAMAC or VME bus modules can carry out the data acquisition. The CAMAC system is the most cost effective. Faster computer interface busses such as Fastbus, VME or VXI bus may also be used. The custom designed data acquisition modules for the hodoscope will produce the necessary microstrip readout chip control electronics, such as the T/H (if not generated internally in the readout chip), a clear signal to reset the shift registers and the clock pulse to multiplex each strip to the analog output.

The analog input channels from different hodoscope planes are read out synchronously with the clock pulse output. The module converts the pulse height information received from the analog output pin to a digital number. In parallel with reading the hodoscope data, it also digitizes the signal(s) from the calorimeter. Immediately after reading out the last signal it clears the hodoscope to reset the readout chip so that it can receive the next event. It is assumed that the analog output of each readout chip in each detector plane is fanned in to allow a single signal to be sent to the readout module. If a microstrip readout chip is used which internally connects the strip which has the maximum signal to the analog output and also produces the encoded address of the strip. In such a case the clock output will not be necessary and the silicon microstrip detectors can be readout asynchronously and much faster. In time tagged data acquisition each interaction can be read out asynchronously and tagged by an accurate clock. Computer will select the coincident events.

The custom made CAMAC modules are connected to the CAMAC crate controllers which are standard devices and available off the shelf. The controllers connect the modules to the data acquisition computer. Depending on the data rate and readout overhead, a single or separate computers can be used to read the hodoscope and the calorimeter. The computer stores data on hard disk, optical drive or nonvolatile RAM depending on the application. If the data acquisition overhead is not high then one of the computers can analyze the data in real time or a separate computer can access the storage media asynchronously. The results of the data analysis are imaged onto the field-of-view through a display system in real time.

The data analysis techniques for nondestructive evaluation inspection resemble closely those of medical Computer Assisted Tomography (CAT) imaging. This type of imaging is based on the Radon transform and back projection techniques and is standard in the industry. New iterative techniques such as Maximum Likelihood and Maximum Entropy methods can also be applied to enhance the image quality. The direct linear algebraic deconvolution (DLAD) technique is another alternative to produce fast images from the data as it is not an iterative process.

Figure 38:
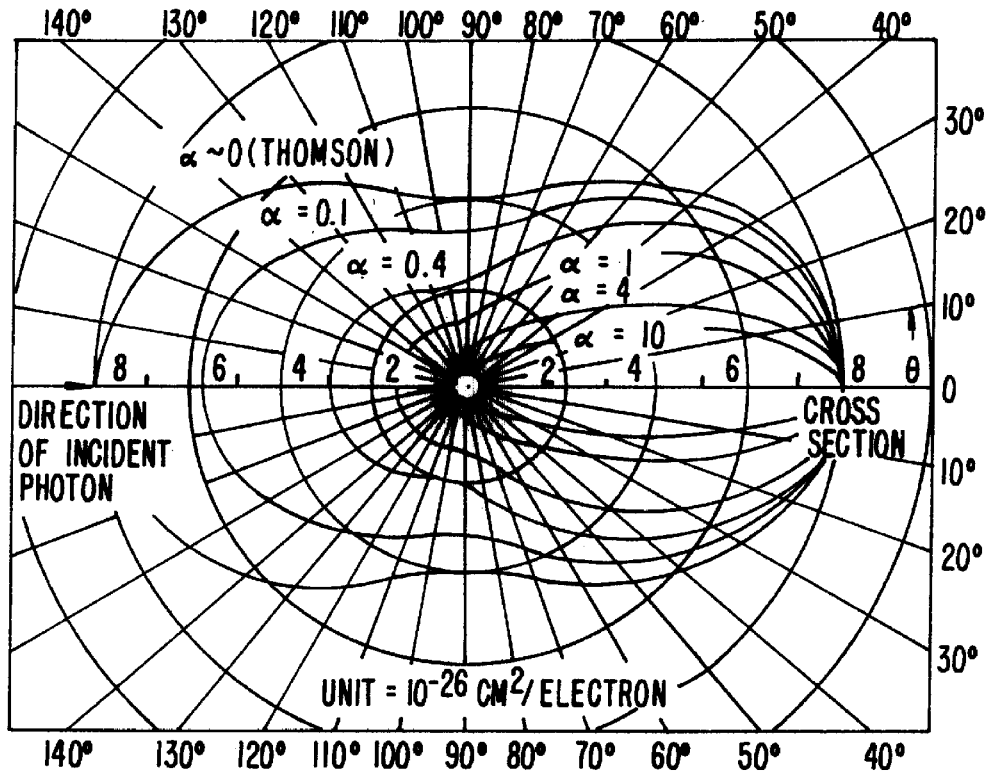
FIG. 38 is a graph illustrating the differential cross section per unit solid angle for the number of photons scattered into Compton angle $\Theta$.

The formation of the calorimeter modules around the silicon strip detector may be redesigned based on the analysis of the Compton scatter cross section and calorimeter angular resolution. In one embodiment, the calorimeter modules may be placed around the silicon detectors in a cylindrical form. In this way, the calorimeter will measure the Compton scattered photons with large scattered angle near 90 degrees. In a preferred configuration, the detector efficiency is improved by considering the Compton scatter cross section as a function of scatter angle. In FIG. 38, the differential cross section per unit solid angle for the number of photons scattered into Compton scatter angle θ is shown, where a is defined as the ratio of photon energy E and electron rest mass: $a = E/mc^2$. For x-ray photon energy from 300 keV to 2 MeV, a ranges from 0.6 to 4. FIG. 38 demonstrates that the Compton scattering probability is higher in the forward direction respect to the incident beam. By placing the calorimeter modules close to the forward direction instead of 90 degrees to the incident beam, the detector efficiency may be improved.

The angular resolution should also be considered in the design of the formation of the calorimeter modules. In the Compton scatter process in the silicon detector, the Compton scatter angle, θ, can be written as a function of the incident photon energy Eg and the scattered photon energy $E_{\gamma 1}$:

$$\cos \theta = 1 - mc^2 (1/E_{\gamma 1} - 1/E_\gamma)$$

where the total energy of the incident photon, $E_\gamma$, is the sum of recoil electron energy, $E_e$, and scatter photon energy: $E_\gamma = E_e + E_{\gamma 1}$. The angular resolution depends on the uncertainty of the energy in the double scatter process in silicon and CsI(Tl) crystal. Thus the FWHM angular uncertainty, Δθ, depends on energy resolution of both the silicon detector and the calorimeter. From the Compton scatter formula shown above, Δθ can be derived as:

$$\Delta\theta = \frac{mc^2}{E_\gamma^2 \sin\theta} \left\{ \Delta E_{e1}^2 + \left[ \frac{E_\gamma^2}{E_{\gamma 1}^2} - 1 \right]^2 \Delta E_{e2}^2 \right\}^{1/2}$$

where $\Delta E_e$ and $\Delta E_{\gamma 1}$ are the energy resolution of the silicon detector and the calorimeter. The relationship between the energy resolution $\Delta E_{\gamma 1}$ and photon energy, $E_{\gamma 1}$, was established by fitting to the experimental results:

$$\Delta E_{\gamma 1}/E_{\gamma 1} = 4.27\% / \sqrt{E_{\gamma 1}}$$

Figure 39:
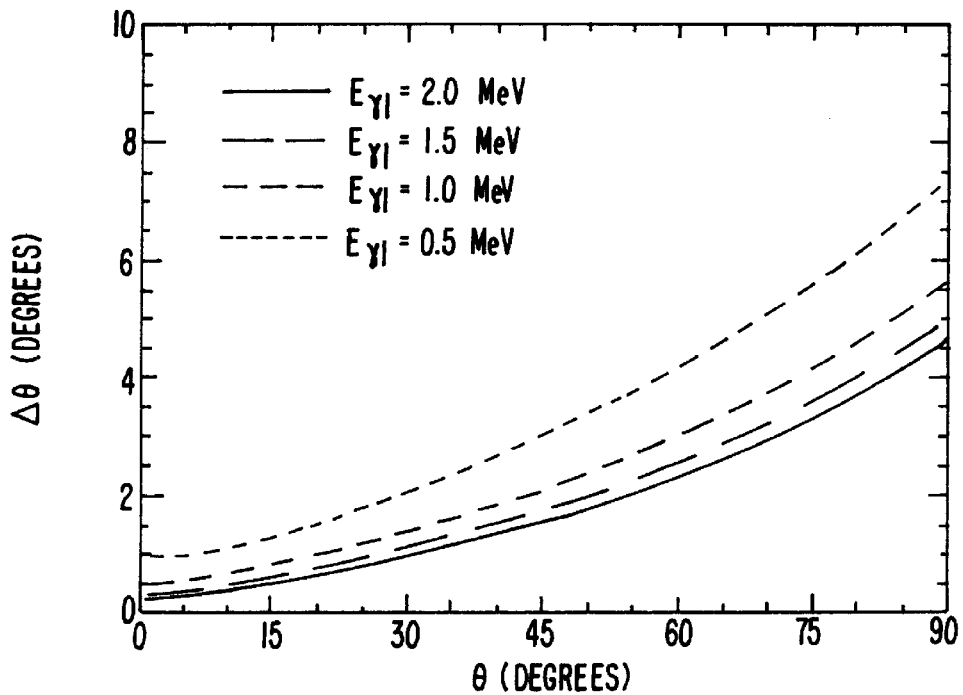
FIG. 39 is a graph illustrating the angular resolution as a function of Compton scatter angle for several different photon energies.

On the other hand, the energy resolution for the silicon detector, $\Delta E_{\gamma 1}/E_e$, can be calculated using the recoil electron energy loss in silicon. To simplify the problem, a minimum ionizing particle is used in the calculation. The energy resolution of the silicon strip detector is given by:

$$\Delta E_e/E_e = (2.35\sigma/N)\sqrt{ND}$$

where N is the total number of electron-hole pairs produced in silicon, σ is the noise fluctuation (ENC) and ND is the number of detectors traversed by the recoil electrons. Two 500 μm silicon detector planes would stop 0.5 MeV recoil electrons and the energy resolution is 2.4% when σ(ENC) =1,000 electrons is used. The energy resolution for different recoil electron energies can be calculated in the same way. Therefore, using the energy resolution for the silicon detector and the calorimeter, the angular resolution as a function of scattered angle is calculated and shown in FIG. 39.

The FWHM angular resolution also depends on the detector geometry and pixel size. The geometric angular resolution depends on the pixel size of the calorimeter (1 cm×1 cm) and the distance between the first scattering point and the second scattering point. The geometric angular resolution is about 1.2° when the calorimeter module is placed 50 cm away from the silicon strip detector. From FIG. 39, if the calorimeter modules are placed within 45° respect to the incident beam, the angular resolution should be less than 2°.

Figure 40:
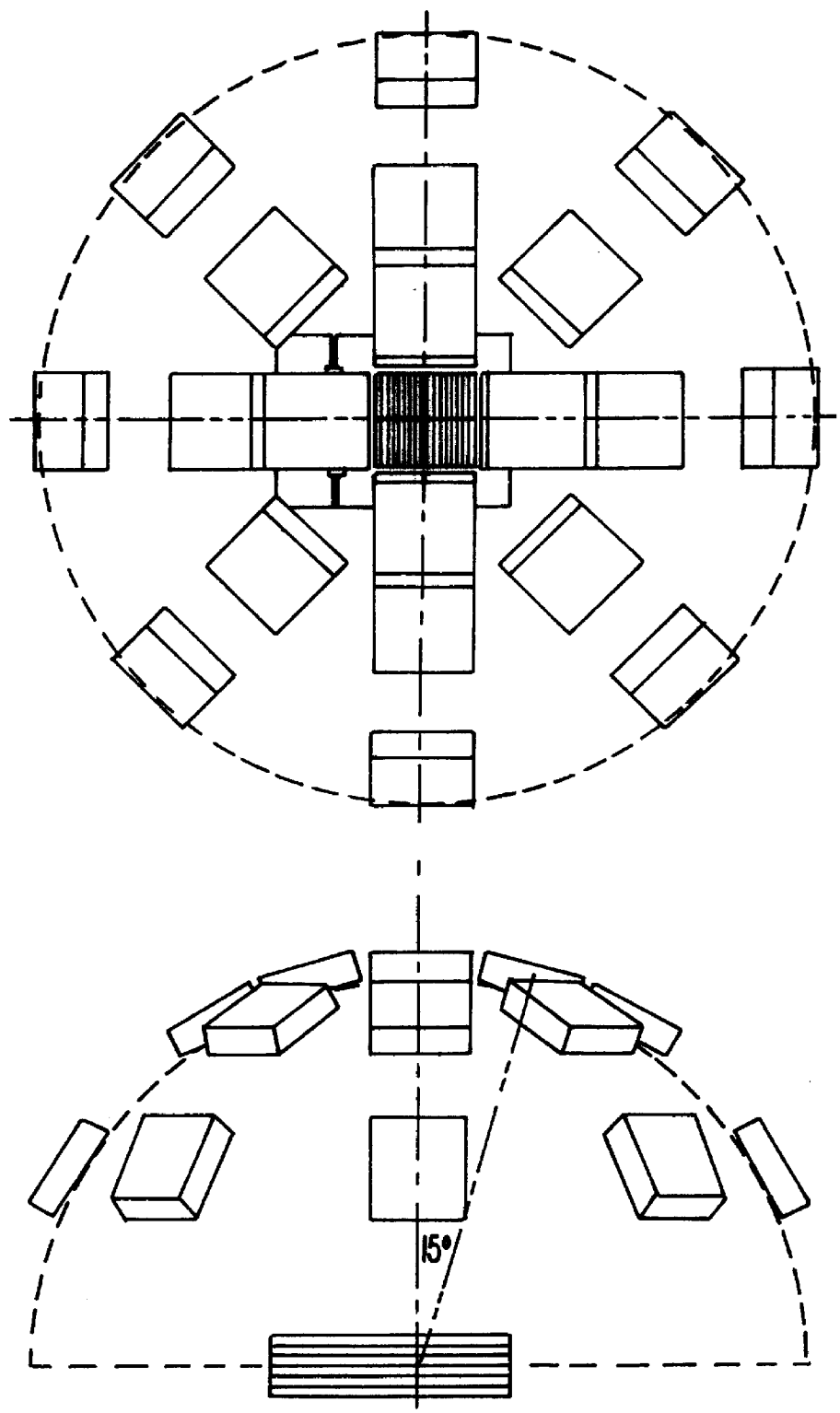
FIG. 40 is an illustration of a CsI(Tl)/photodiode module configuration for a NADIA detection system.

Therefore the calorimeter modules may be placed close to the forward direction in order to obtain higher angular resolution and detector efficiency. FIG. 40 is an illustration of a CsI(Tl)/photodiode module formation for a NADIA detection system. In this embodiment the modules are placed on a hemisphere with a radius of 50 cm. More detector modules are placed in the forward direction with respect to the incident beam. A hole with a 15° solid angle is left at the center of the calorimeter to allow unscattered photons to pass.

High Sensitivity, High Resolution Uncollimated Single Photon Emission Computed Tomography System (COMSPECT)

Present SPECT systems with Anger cameras that have acceptable resolution obtained with converging mechanical collimators have limited sensitivity, about 0.1%. Only about 1 γ-ray photon in 1,000 from the standard phantom passes through the collimator. Increasing the spatial resolution by tightening the collimator significantly decreases the sensitivity and vice versa. The elimination of the mechanical collimator improves the sensitivity by at least a factor of 100. This reduces the imaging time to 10 to 30 s from the current 20 min. Such fast measurement times enable physicians to perform dynamic clinical examinations regarding the metabolic processes that provide important data for medical diagnosis. For anatomical imaging a larger data sample with high statistics can be obtained in shorter time and/or patient dose can be cut significantly. High sensitivity may enable realtime cardiac imaging by applying the Multi-Gated Acquisition (MUGA) technique. This means that ≧30 images per second must be obtained.

The angular resolution of the detector is potentially 1.8° to 1° for 141 keV and 1° to 0.4° for the 364 keV forward scattered (θ≦90°) photons. This translates into spatial resolutions of 6 to 3.5 mm for 141 keV and 3.5 to 1.5 mm for 364 keV photons at a distance of 20 cm which is a typical distance in brain studies. The spatial resolution of the present SPECT instruments is about 7 to 12 mm for commercial systems governed by the collimator geometry typically about 1 mm×1 mm×¾" for high resolution systems. Significantly higher spatial resolution is important as the present SPECT technology is not expected to go below 6 mm without significantly reducing the sensitivity. The number of pixels forming the 3 dimensional image will also increase by about a factor of 8. If the total data acquisition time is kept constant the proposed system will have an SNR advantage 3.5 over the conventional SPECT systems for a voxel size which is ⅛th smaller due to the improvement in the spatial resolution by a factor of 2. This SNR advantage can be traded for faster data acquisition while keeping the SNR the same as the conventional systems. Thus, one can acquire the data 12.5 times faster by maintaining the same SNR as the conventional SPECT systems for a voxel size which is ⅛th smaller than such systems.

The scattered photon background and the γ-ray attenuation inside the patient can be corrected using techniques already developed. The energy resolution is about 3% (141 keV) and 2% (364 keV) compared to about 8 to 10% FWHM for the Anger camera at 141 keV. The improved energy resolution of the proposed detector may be used to reject a significant portion of the background photons. The remaining can be subtracted by techniques such as the Two-Window Correction method. The γ-ray attenuation inside the patient can be corrected with well known techniques such as preprocessing, intrinsic and postprocessing corrections for an uniform attenuating medium. The Anger camera is very sensitive to scintillator defects and photomultiplier tube (PMT) gain variations. Therefore, daily field uniformity correction floods are acquired in a clinical setting and the weekly "center-of-rotation" parameter is determined from a separate calibration study. The system of the invention does not use PMT's and therefore is simpler to maintain. The noise in SPECT is Poisson counting noise and proportional to the square-root of the number of events. The high sensitivity of the COMSPECT system (>100 compared to the Anger camera with mechanical collimator) is expected to reduce the Poisson counting noise by about a factor of 10.

Figure 41:
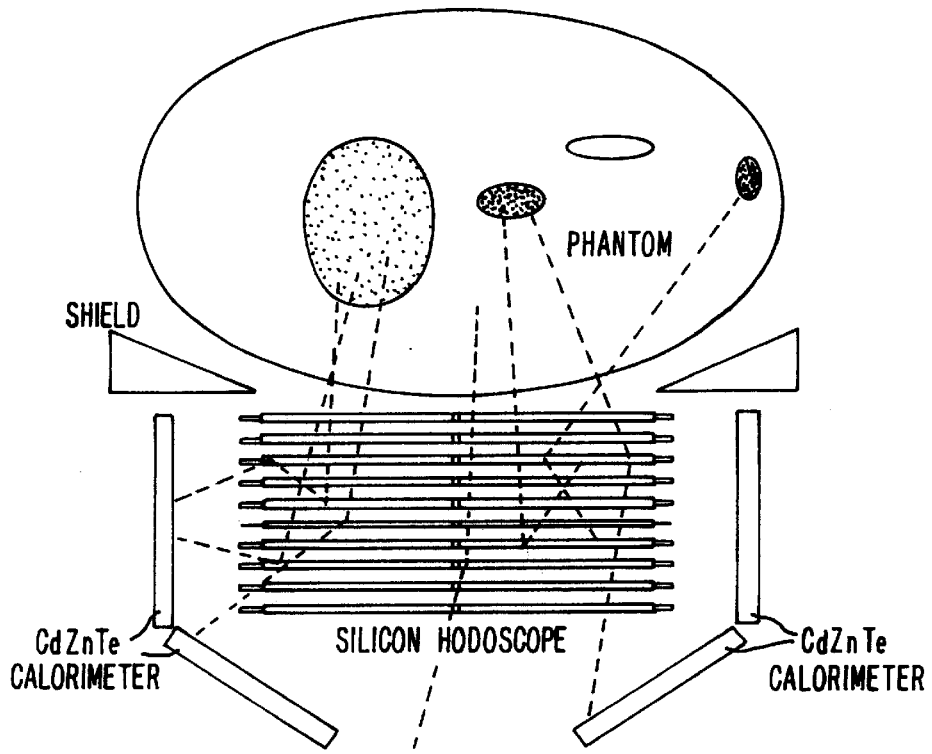
FIG. 41 is an illustration of a side view of an embodiment of the COMSPECT system.
Figure 42:
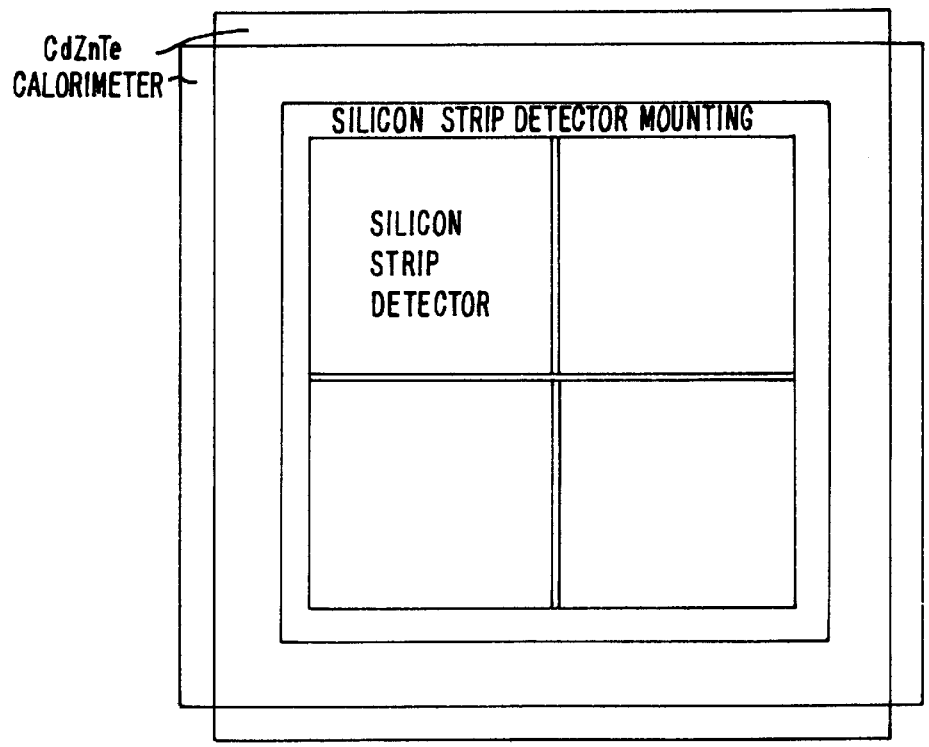
FIG. 42 is an illustration of a top view of the COMSPECT system illustrated in FIG. 41.

One embodiment of the COMSPECT system is illustrated in FIGS. 41–42. The hodoscope is made from 15 to 25 planes of silicon strip detectors of thickness varying from 0.5 mm to 1 mm depending on performance and availability. The total Compton scatter probability will vary from 40% for fifteen 1 mm thick silicon strip detectors to about 35% for twenty five 0.5 mm thick detectors. The active area of the silicon strip detectors can be increased by mounting four detectors side by side on each plane (FIGS. 41–42). The hodoscope height depends strongly on the silicon detector plane separation. If 1 mm thick detectors are used than the plane separation is about 1 cm and the hodoscope height about 15 cm. These values as well as the thickness and separation of the silicon detectors can be further optimized through Monte Carlo simulations and experimental study.

The calorimeter is made from about 2 mm thick CdTe or CdZnTe strip detectors. The reason for this selection is the higher energy resolution obtained from CdTe/CdZnTe detectors especially at lower energies. A CsI(Tl) calorimeter can also be used.

A single layer of calorimeter will be placed around the hodoscope as shown in FIGS. 41–42, as close as possible, without degrading the angular resolution significantly by introducing additional error from geometric combination of pixels. The gap at the bottom is due to the energy threshold at the silicon detectors which is expected to be >5 keV. The incident photons that deposit energy less than the threshold energy will not be detected in the hodoscope and such small angle scatters need not be stopped at the calorimeter. One such event is demonstrated in FIG. 41. A shield is placed in front of the calorimeter to decrease the background count rates. The geometry, strip pitch, thickness, shielding and the size of the gap at the bottom of the calorimeter may be optimized by Monte Carlo simulations. The detector geometry can be optimized to any form such as square, rectangular, cylindrical, spherical, parabolic, etc. that gives the best results for a specific application.

Figure 43:
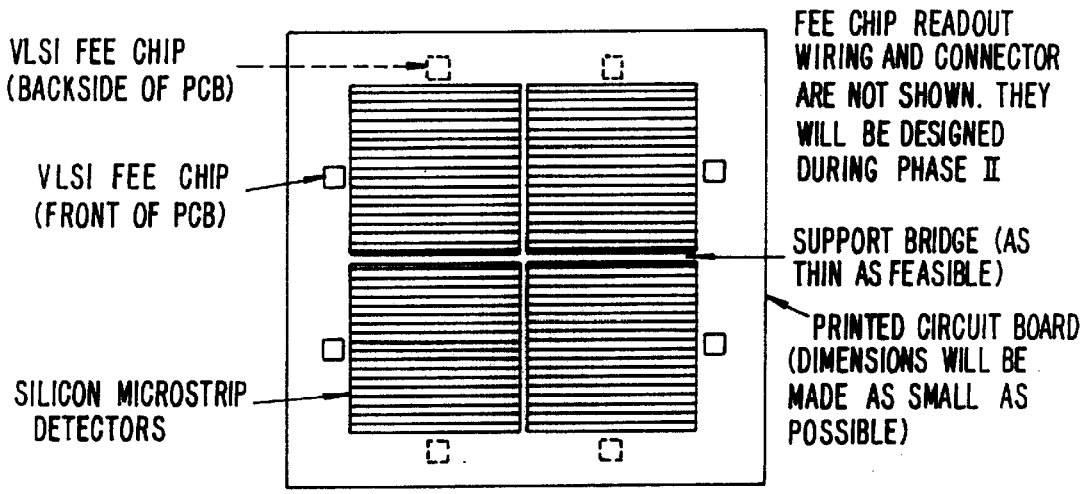
FIG. 43 is an illustration of the FEE readout chips and the cilison strip detector planes mounted on a PCB.

Each plane of the hodoscope is made from four silicon strip detectors of approximately 6.4 cm×6.4 cm active area and 1 mm thick mounted as close to each other as possible to increase the active area by a factor of 4. This will give an active area of 12.8 cm×12.8 cm equal to about 164 cm$^2$. Preferably the hodoscope includes about 15 to 25 detector planes. The separation of the hodoscope planes is approximately 1 cm. The silicon strip detectors are mounted on a printed circuit board (PCB) or a ceramic holder. The front end electronics (FEE) readout chip is mounted on the PCB in nearly touching distance to the silicon strip detector as shown in FIG. 43. The fan in from strip pitch to FEE chip pad pitch will be done on the silicon strip detector for reliability and ease of ultrasonic wire bonding. The FEE chip can be used in the wafer form to reduce mass near the hodoscope. Most of the electronics is preferably assembled outside the detector and only the most essential components are placed on the PCB. Small size surface mount components are used on the PCB to reduce mass. Preferably miniaturized connectors and cables are used to interface to the data acquisition system.

The small size of the active area and the dividers between the four silicon strip detectors at each plane do not cause any problem such as truncating the sides or producing gaps in the image. This is because the proposed technique inherently has a large field of view and the detector active area can be smaller than the imaged organ of the patient. Also any gaps or dead strips in the hodoscope can not produce gaps in the image. Smaller active area, small number of dead strips at each plane and gaps in between the silicon strip detectors can only reduce the detection efficiency and will not affect the image.

The silicon strip detectors are designed and fabricated using the FOXFET AC coupling technique on both the junction and ohmic sides. This technique improves the signal quality especially at the ohmic side mostly because the bias resistor formed through the FOXFET technique is much larger than other techniques. It also eliminates external capacitances and resistors which become bulky and costly when large number of channels are used. Preferably the FOXFET silicon strip detectors are highly radiation resistant.

Although the preferred embodiment includes a calorimeter, the COMSPECT system may be fabricated without a calorimeter to enhance energy and spatial resolution. In one embodiment of the invention, the calorimeter detectors are CdZnTe strip detectors. These detectors have excellent energy resolution for 10 to 250 keV γ-rays. Therefore, CdZnTe is especially useful to work with $^{99m}$Tc, the most commonly used radionuclide. The energy resolution of CdTe and CdZnTe decreases with increase in the energy of the incident photon. However, the CdZnTe strip detectors are just becoming available and unforeseen problems may come up.

The second choice for the calorimeter is the CsI(Tl) crystals coupled to specially developed PIN photodiodes. The energy resolution of these crystals, contrary to the CdTe detectors, increases with the increase in the γ-ray energy. Therefore, they are an excellent choice for source γ-rays>250 keV. At higher energies a calorimeter may also become more important because the thickness of silicon required to stop such high energy gamma rays will be large as the photon must go through multiple Compton scatters before it will be absorbed. If a calorimeter is used the incident photon only needs to make a single Compton scatter in the silicon hodoscope.

The energy resolution for 1×1×2 cm$^3$ crystals of CsI(Tl) are approximately 5% at 662 keV using a $^{137}$Cs source. These results show that a CsI(Tl) calorimeter is an excellent alternative and it can be used at lower energies by improving energy resolution by decreasing crystal size without significantly effecting its stopping power. For example, a 0.5 cm long CsI(Tl) crystal can absorb 95% of 141 keV photons.

The COMSPECT detector can be used at higher energies such as 511 keV. Prior art SPECT systems based on the gamma cameras loose their detection and collimation efficiencies at higher energies. The detection efficiency of the COMSPECT system can be adjusted for higher energies by increasing the total thickness of the hodoscope and the calorimeter. Also the electronic collimation efficiency is expected to improve significantly at higher energies due to the improved energy resolution. This new capability is especially important for use with positron emitting radiopharmaceuticals. Although, PET systems are used to image positron emitting radionuclides, lower cost high energy SPECT systems may become useful for certain applications, locations or circumstances. However, the need for a nearby radionuclide and/or radiopharmaceutical generator may limit such use.

In general there are two optimum configurations for the COMSPECT system within the capability of recently introduced detector technology. They are the low (81 to 250 keV) and high (250 to 511 keV) energy SPECT systems. In fact, each system can work throughout the extended SPECT energy range, 81 to 511 keV with somewhat lower efficiency and spatial resolution, for example by placing a CsI(Tl) calorimeter behind the 2 mm thick CdZnTe plane. The CdZnTe calorimeter is useful for low energy radionuclides while both the CdZnTe and the CsI(Tl) calorimeter can be used with the silicon hodoscope for high energy sources. In such an arrangement interactions in all three sections may happen and can be used as viable data for imaging. The low energy COMSPECT system can be fabricated as a hodoscope only instrument or with a calorimeter. The high energy COMSPECT system can be designed hodoscope surrounded by a thick CdZnTe or CdZnTe together with CsI(Tl) or similar capability detectors.

The origin of CdZnTe is the Cadmium Telluride (CdTe) detector. CdTe contains relatively high atomic numbers (48 and 52) with a large enough bandgap energy (1.47 eV) to permit room temperature operation. It has a density of 0.06 gr/cm$^3$ and energy required to create a single electron-hole (e-h) pair is 4.43 eV. The hole mobility is about a factor of 30 slower than the electron mobility. The hole life times are also very short due to the low mobility because the effects of trapping and recombination are enhanced. The hole collection efficiency improves with the purity of the material used. The probability of photoelectric absorption per unit pathlength is approximately a factor of 100 times larger than in silicon for typical gamma ray energies. For example, it is opaque to low energy x-rays for thicknesses in the range of a mm. Its energy resolution is not comparable to silicon detectors for low energy x-rays, because of the poor hole collection efficiency. The energy resolutions measured for CdTe detectors are 3.5 keV at 122 keV at room temperature.

Problems with CdTe detectors appear to be related to a large degree to the practice of growing CdTe detector by the travelling heater method (THM), using Te-rich solutions.

THM crystals must be doped with an element such as Cl to achieve high resisitivity, and chlorine doping has been associated with detector operating instabilities (counting rate polarization) and long-term reliability problems. Also, THM crystals are generally of small volume and have rather low yields of detector grade material, which leads to high detector prices. More fundamentally, the CdTe bandgap of 1.47 eV limits resistivities to the low-109 ohm-cm range, resulting in relatively large room temperature leakage currents.

The CdZnTe detectors were developed by Aurora Technologies Corporation (ATC) to improve the CdTe detectors they were manufacturing as gamma ray detectors. They added up to 20% high purity ZnTe to CdTe to obtain $Cd_{1-x}Zn_xTe$ ($x \leq 0.2$). ATC has developed a new high pressure Bridgman (HPB) approach to growing detector quality crystals of CdZnTe. HPB crystals are quite large (up to 10-cm in diameter and 10 kg), have yields of detector grade material of over 70%, and exhibit uniform near-intrinsic resistivity without doping. Detectors fabricated from HPB grown crystals exhibit excellent stability, reliability and lifetime. Furthermore, the HPB process can be used to grow high quality crystals of $Cd_{1-x}Zn_xTe$ throughout the entire alloy compostion range. Alloying ZnTe with CdTe increases the bandgap, resulting in much higher resistivities and correspondingly lower leakage currents than CdTe.

Growth of $Cd_{1-x}Zn_xTe$ and other wide bandgap II–VI compound crystals from the melt is generally complicated by relatively high melting temperatures and vapor pressures and the fact that the melting temperatures are comparable to or exceed the softening temperature of quartz. The CdZnTe crystal preparation has been extensively discussed in the literature. The results show that $Cd_{1-x}Zn_xTe$ detectors, especially $Cd_{0.8}Zn_{0.2}Te$, is an improvement over CdTe. However, there has been also significant improvement accomplished on CdTe detectors.

The long term stability of CdZnTe detectors has been demonstrated. Another study was also recently completed in which a CdZnTe detector was maintained under constant bias from March 1989 until April 1992, on-line in a factory environment. There was no measurable change in its counting efficiency over a three-year period. Furthermore, the ability to produce large, homogeneous boules raises interesting new prospects, such as 1) fabrication of large area strip detector arrays for the COMSPECT system and 2) large-quantity, low-cost detector manufacturing which could make the COMSPECT instrument a cost effective high performance solution.

Figure 44:
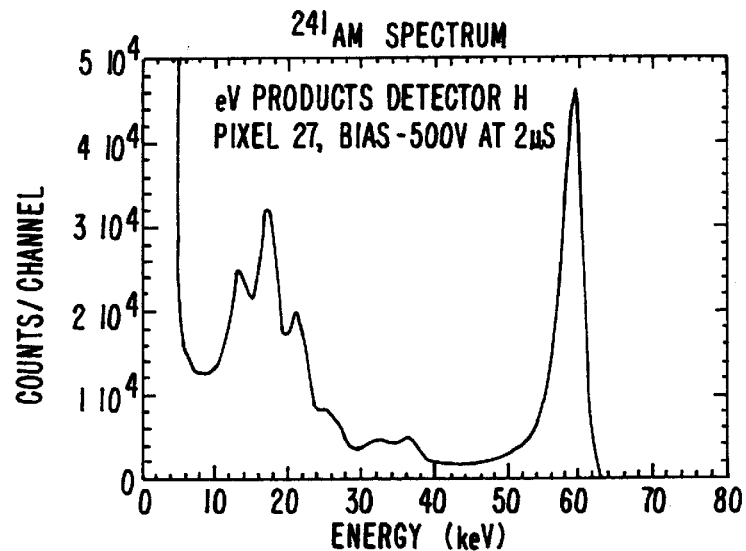
FIG. 44 is a graph illustrating the energy spectrum of Americium-241.

The energy resolution of both the CdTe and CdZnTe detectors to 10 to 250 keV energies is important for the proposed prototype SPECT system. FIG. 44 shows the energy spectrum of a Americium-241 source with a CdTe detector. The x-ray emission at 13.9, 17.7, 20.8, 26.4 and 59.5 keV (with its escape peaks from characteristic K x-rays from Cd at 36.5 keV and Te at 32.5 keV) are clearly seen with good energy resolution. The slight low energy tail observed for the 59.5 keV peak is typical of that observed with CdTe detectors and is due to incomplete charge collection for some of the events.

Figure 45:
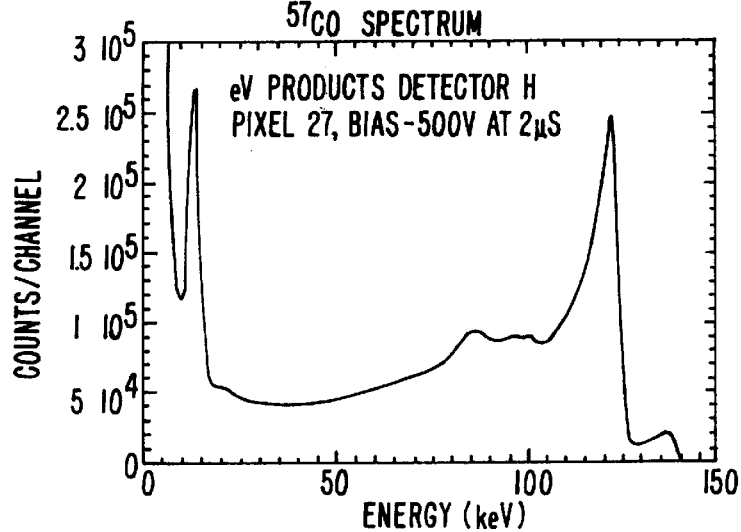
FIG. 45 is a graph illustrating the energy spectrum of Cobalt-57.

The energy spectrum of $^{99m}Tc$ obtained by a 2 mm thick CdZnTe crystal is shown in FIG. 45. The low energy tail is clearly seen at higher energies.

In one embodiment of the system, CdZnTe strip detectors produced from $Cd_{0.8}Zn_{0.2}Te$ wafers were used. The strip pitch was 1 mm. The 32 strips were constructed on each side on a 3.2 cm×3.2 cm active area. The strips on each side were made orthogonal to each other to give both the x and y dimensions of an interaction. The thickness of the CdZnTe strip detectors can be made from 1.5 to 2.5 mm.

Two-dimensional arrays of CdZnTe pad detectors can also be used with improved results over the strip detectors. This is because the pad detectors do not have the position ambiguity of strip detectors if more than one event interacts with each detector simultaneously.

A full size cylindrical COMSPECT system was modeled. The MCNP Monte Carlo code discussed above is used. The internal and external radii of the cylindrical COMSPECT were 15 and 50 cm, respectively, and 50 cm long. The phantom used at the center was the standard 20 cm diameter 20 cm long cylinder filled with water and 1 $\mu Ci/cc^{99m}Tc$ radiotracer. Double sided silicon strip detectors 1 mm thick and 1 mm strip pitch were modelled in cylindrical form. All together 36 planes were placed inside the detector with 1 cm separation between planes. The total thickness of the 36 planes is 3.6 cm corresponding to 72% Compton scatter probability. The 141 keV γ-rays, produced uniformly in all directions in the phantom, were tracked along their paths until they were fully absorbed or escaped through the back or sides of the detector. A 3 keV energy threshold of detection was imposed on each silicon detector. A calorimeter behind or at the sides of the model was not used.

Figures 46, 47:
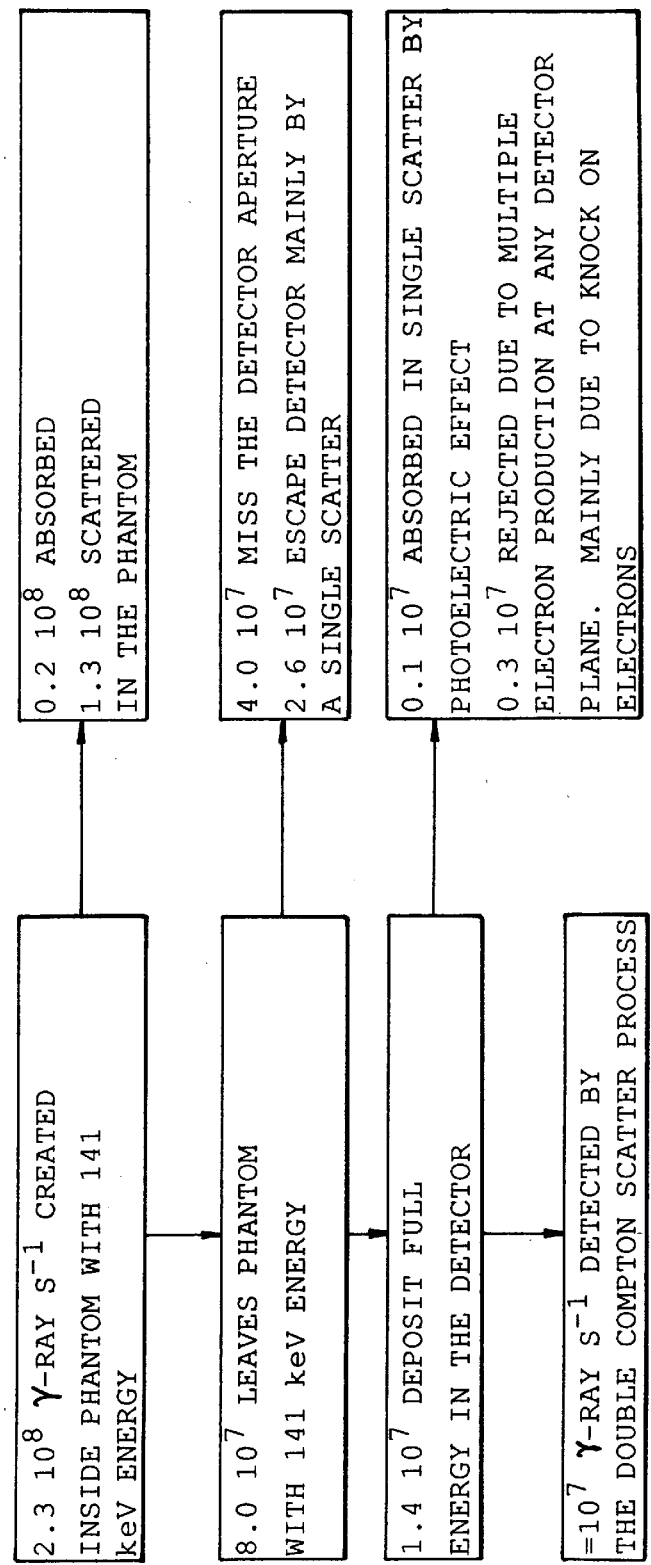
FIG. 46 is a flowchart outlining the Monte Carlo γ-ray history for the COMSPECT system.
FIG. 47 is a table of the sensitivity of the COMSPECT system compared to the Tri-SPECT system.

The history of the 141 keV photon was traced by Monte Carlo calculations. The results are shown in FIG. 46. The Monte Carlo calculations were carried out for about 100,000 events and the results scaled to the simulated phantom. The 141 keV photons scattered in the phantom are effectively discriminated by the high energy resolution. This significantly reduces the major scattered photon background in COMSPECT. The single scatter photons are rejected as their directions cannot be measured. The events which create multiple electrons in the same detector wafer are also rejected. Most of these are probably due to knock on electrons by the recoil electron. In most cases the secondary electrons are created and absorbed within the pixel size at the position of the interaction. These events are legitimate and can be used in imaging.

The forward and backscattered γ-ray events can be easily identified because of the strict relationship imposed by the Compton scatter formula especially at low photon energies. For 141 keV $^{99m}Tc$ γ-rays the energies deposited in the interaction point nearest to the patient are limited to 0 to 31.5 keV and 110.5 to 90.9 keV for forward and back scattered photons ($\theta \leq 90°$), respectively. For the interaction point farthest from the patient ($90° \leq \theta \leq 180°$) the energies deposited are 31.5 to 50.1 keV and 141 to 110.5 keV for the forward and back scattered photons, respectively. Since the energy at each interaction plane will be measured separately such widely different energy deposition for the forward and backward scattered photons should be easily identifiable and the direction cones can be calculated. Therefore, the backscattered events that deposit full energy in the detector are good events and can be used in imaging.

The point sensitivity is estimated to be about 1,500 Cts s$^{-1}$ $\mu Ci^{-1}$ (FIG. 47). This is an improvement of about a factor of 40 over the present systems with highest point sensitivity and about 150 times of the average point sensitivities reported by manufacturers. The volume sensitivity of the simulated detector is about 500,000 Cts s$^{-1}$ cm$^{-1}$ found by dividing the good event rate, 1×10$^7$ cts s$^{-1}$, by the length of the phantom (20 cm). High sensitivity and low spatial resolution SPECT instruments such as SME-810 claim 40,000 Cts s$^{-1}$ cm$^{-1}$ volume sensitivity. The simulated COMSPECT is about 12 times higher in sensitivity and also has high spatial resolution. If compared to low sensitivity high resolution instruments such as Tri-SPECT by Technicare, ASPECT by Digital Scintigraphics and TRIAD by Trionix it is 150 to 500 times more sensitive. The sensitivity of the COMSPECT instrument strongly depends on the amount of silicon used and can be improved further by increasing the number of silicon detectors. The number of silicon strip detectors can also be decreased substantially to reduce cost since the sensitivity is exceptionally high and significant sacrifice is affordable.

The FWHM uncertainty in the cone half-angle, $\Delta\theta$, due to a detector of finite energy resolution (FWHM), $\Delta E_{e1}$ and $\Delta E_{e2}$ at first and second scattering planes can be calculated using the Compton scatter formula:

$$\Delta\theta = \frac{mc^2}{E_\gamma^2 \sin\theta} \left\{ \Delta E_{e1}^2 + \left[\frac{E_\gamma^2}{E_{\gamma 1}^2} - 1\right]^2 \Delta E_{e2}^2 \right\}^{1/2}$$

where $mc^2$ is the electron rest energy (511 keV), $\theta$ is the Compton scatter angle and $E_\gamma$ and $E_{e1}$ are the incident and scattered photon energies. The energy resolution for electrons stopped inside silicon microstrip detectors varies from 6% at 5 keV to 0.75% at 350 keV using the formula. The angular resolution, $\Delta\theta$, for forward scattered γ-rays ($\theta<90°$) varies from 1° at $\theta=30°$ to about 1.8° at $\theta=90°$ for 141 keV ($^{99m}$Tc) incident photons. The same calculation carried out for the 364 keV $^{131}$I γ-rays give angular resolutions varying from 0.4° to 1° for $\theta=15°$ to 90°. The angular resolution improves significantly with an increase in the energy of the photon. Also the effect of the amplifier noise reduces as more electron-hole pairs are created by higher energy scattered electrons. At a distance of 20 cm these angular resolutions produce effectively 6 to 3.5 mm spatial resolutions for 141 keV and 3.5 to 1.5 mm for 364 keV γ-rays.

The energy resolution due to the statistical fluctuation for electrons stopped inside silicon microstrip detectors varies from 1.33% at 100 keV to 0.75% at 350 keV using the formula. The electronics noise of the detector is about 2 keV. Therefore the total energy resolution will be dominated by the electronics noise. The angular resolution is calculated with energy resolution of 2 keV (FWHM), where $\Delta\theta$, for forward scattered γ-rays ($\theta<90°$) varies from 5° at $\theta=30°$ to about 3.2° at $\theta=70°$ for 141 keV ($^{99m}$Tc) incident photons. The same calculation carried out for the 364 keV $^{131}$I γ-rays give angular resolutions is approximately 1° from $\theta=20°$ to 90°. The angular resolution improves significantly with an increase in the energy of the photon. At a distance of 10 cm these angular resolutions produce effectively 8.7 to 5.5 mm spatial resolutions for 141 keV and 1.7 mm for 364 keV γ-rays.

The geometric angular resolution, $\Delta\theta_{Geom}$, which gives the axis of the image cone, depends on the silicon microstrip detector pixel size and the distance between the first two scatters. The FWHM value can be calculated similar to that for a collimator. Normally the geometric angular resolution is kept much smaller than the scatter angle variation, which depends strongly on the energy resolution as shown above. It is easier to adjust the geometric angular resolution in a silicon microstrip detector as the pixel dimensions can be as small as 25 microns. The pixel size for the simulated model was 1 mm by 1 mm. The average distance between the first two interactions was about 28 cm, which translates to 0.2° geometric angular resolution.

The Monte Carlo analysis shows that about $1\times10^8$ photons s$^{-1}$ out of $2.3\times10^8$ enter the detector. The simulated detector has 36 cylindrical planes with about $10^4$ cm$^2$ average area and about 75% of the photons making an interaction ($7.5\times10^7$ photons s$^{-1}$). If each silicon microstrip detector wafer used is 5 cm×5 cm dimension then the singles rate in each wafer is about 5,000 Cts/s. Such singles rates are not excessive for silicon microstrip detectors which produce about 20 ns long pulses. The coincident requirement will further reduce the actual readout rate to about 670 s$^{-1}$. Therefore, dead time per detector is not a problem. However, the total count rates of the whole detector will be very high. This is also the case for silicon detectors that are used as vertex detectors in high energy physics experiments. This problem is solved by establishing high level parallelism in readout electronics for which the silicon microstrip detectors are highly suitable. One possible way is to divide the detector into many radial sections and read each section individually. If it is divided into 20 sections than readout rate at each section will be about 500 KHz which can be easily handled by the old industry standard CAMAC data acquisition system. The data rate will be even smaller due to some loss of events at the edges when the photons scatter into adjacent sections. This will also reduce sensitivity somewhat unless such events can be recovered by the electronics. There is also a large number of channels to readout. This is solved by using high density ASIC chips directly connected to the microstrips. Chips which produce a trigger signal when there is valid data and connect the strip that contains information to the output can be used.

The energy resolution is expected to be about 2% for a 300 keV photon and 1,000 electrons ENC noise. This is an approximate estimation assuming that the 300 keV photon produces a substantial Compton scatter in the first scatter plane and the recoil electron is fully absorbed in the same wafer. The scattered photon is also fully absorbed at another plane or calorimeter. The energy resolution decreases with decreasing energy. The angular resolution depends strongly on the energy resolution as given by the Compton double scatter formula. The angular resolution of the COMSPECT system is approximately 1° for 300 keV. The spatial resolution at the center of the body at about 30 cm distance is 5 mm and for the head at 15 cm distance is 2.6 mm. The angular resolution also decreases at lower energies. A 4° angular resolution expected at lower photon energies will produce spatial resolutions of about 1 cm for head and about 2 cm for body. The peak position of the distribution can be determined more precisely than the angular resolution which could be useful for small point type sources or organs in the patient.

A simple model of a single head COMSPECT system is simulated. Ten layers of 12.4 cm×12.4 cm area and 1 mm thick silicon strip detectors stacked up with 0.5 cm spacing in between the detector planes to form the hodoscope. A single sheet of 50 cm×50 cm area and 2 mm thick CdTe detector calorimeter is symmetrically placed 6 cm under the last silicon plane. A 141 keV gamma ray source with 0.5 cm diameter is centrally placed 10 cm above the first silicon plane. A threshold energy of 10 keV was applied to the silicon strip detectors. An event is generated only if the incident γ-ray makes a Compton scatter in one of the silicon planes and also interacts at the calorimeter. There were a total of 56,234 triggers out of $10^6$ incident γ-rays. The low efficiency, about 5.6%, was due to small silicon thickness, 1 cm (about 30% Compton scatter probability), and because the calorimeter did not cover the sides of the hodoscope (most of the photons scattered >70° were not detected) and its thickness was 2 mm (about 85% to 50% absorption probability for 90 to 131 keV scattered photons due to the Compton geometry). About 0.56% of the incident photons produced a photoelectric absorption inside the silicon hodoscope. The total number of events that deposited full energy in the detector is 4.2%. If the events are restricted to total absorption in the calorimeter after Compton scattering once in the silicon hodoscope about 2.8% of the incident photons were detected. This excludes totally absorbed events in silicon after $\geq 2$ Compton scatters in the hodoscope which can be used for imaging.

Two more sources were added to the above single 0.5 cm diameter source discussed above. They are placed collinear, one 2 cm from the center source in −x direction and the other 1.5 cm at +x direction. All the sources produced 141 keV γ-rays sprayed into a cone the size of the hodoscope. The photons produced by the sources at the sides missed part of the detector aperture due to their position. Therefore, the strongest source imaged was the centrally placed one. The images were obtained using a standard analysis program. This program integrated the overlap of each event ring at the corresponding pixel. The energies deposited at the hodoscope and the calorimeter are randomly Gaussian distributed using the calculated energy resolutions for the proposed prototype detector to simulate authentic spatial resolution. The results are shown in FIGS. 48–49. The first is a surface and the second a density plot.

The same data was also analyzed using the DLAD technique with positivity requirement. Positivity requirement is based on the fact that the resultant image must be comprised of zero or positive numbers. Within the time available only a simple detector response function can be calculated. Geometric effect was not included. This gave rise to some distortion to the position of the source images especially to the ones on the sides. The results are shown in FIGS. 50–51. The DLAD analysis results show the effectiveness of this method. The standard technique produces a large tail due to the overlapping event rings near the source position. DLAD technique eliminates this effect and gives sharp images. Improving the detector response function and adding the geometric factor are expected to improve these images further.

The new front end electronics (FEE) readout chip is a 64 channel, charge sensitive, mixed signal ASIC CMOS chip. Each channel of the chip consists of an analog section and a digital section. The input from the silicon strip detector comes directly into a low noise charge sensitive amplifier. The output of the charge sensitive amplifier goes into an optional inverter and a shaper amplifier. The inverter enables the use of both positive or negative input signals. A two stage trigger circuit consists of two comparators before and after shaping amplifier. The first one provides a fast trigger signal with small timing jitter through a high precision threshold level. The second trigger signal is slower than the first but has high pulse height accuracy and used to label the channels that have a signal. The fast triggers from all channels are sent to an OR circuit to produce the external trigger output to signal external readout interface that an event is occurred and the chip contains valid data. There are three readout modes for the chip: 1) a sparse readout mode which allows the readout of only the strips that have a signal, 2) a nearest neighbored readout mode which allows the readout of the strips with a signal and the two nearest neighbors, and 3) an all channel readout mode which allows the readout of all the channels of the chip in sequence. It also has 4 different integration speeds (200 nsec to 4 msec) for application to detectors with different speeds such as fast silicon strip detectors and slow CsI(Tl) crystals. The noise performance of the chip is about 1,000 e (noise equivalent charge: NEC) per 20 pf input capacitance, and readout speed of the chip is well above 1 MHz.

If a calorimeter is not used the direction and the energy of the incident photon has to be measured in the hodoscope. This can be achieved by increasing the total thickness. These measurements can be made by two scatters where the second scatter is a photoelectric absorption or by $\geq 3$ scatters where the system is over determined. The energy and the scatter angle can be determined in more ways then one and the last scatter need not be an absorption. The last case also has interesting consequences. The Compton scatter direction depends on polarization and, therefore, direction of the incident photon can be limited to a portion of the event ring. This can dramatically improve the imaging. However, there is one problem remains to be solved, in what order the γ-ray scattered. Since the $\geq 3$ scatters in the hodoscope is over determined there is ample information to solve the hiearchy of the interaction points. For example, $E_\gamma = E_{e1} + E_{\gamma 1}$ requirement at each scatter can be applied, polarization can be used, the event ring can be checked to cross the organ imaged and Compton scatter formula can be applied to rule out unphysical combinations.

Monte Carlo simulation of a hodoscope only system has been carried out using the same geometry as discussed above without a CdZnTe calorimeter and with 20 silicon strip detector planes. Out of $3 \times 10^6$ 141 keV γ-rays incident on the detector, 22% made a single scatter and escaped out of which about 10% were absorbed by photo electric effect. The 7.7% of the incident gamma rays made two scatters and 20% of these (1.6% of total incident) deposited their full energy in the hodoscope. The 4.2% of the incident γ-rays produced $\geq 3$ scatters. Most of these, in theory, may be used to determine the incident photon energy and scatter angle. If the CdZnTe detector calorimeter is used to surround the sides and the bottom of the detector than >10% efficiency is expected from the COMSPECT system which is at least 100 times the gamma camera with collimator.

If a pure single line source is used then a high sensitivity imaging mode can be applied with some reduction in spatial resolution. In this mode the background discrimination cannot be applied for double scatters. The requirement that the double scattered photon must deposit all its energy in the hodoscope reduces the number of useful events for imaging by 80%. Since the energy of the incident photon is known than the missing energy of the escaped photon can be added to the second scatter and the scatter angle can be determined. This method applied to the experimental data and the signal is improved somewhat but the background is also increased. The increase in data rate was not high as the experiment used a CsI(Tl) calorimeter which stopped about 80% of the Compton scattered 511 keV photons ($\approx$395 keV). For a hodoscope only system it may increase good data rate by a significant factor.

Scintimammography is a new field and there are no dedicated instruments yet available. Therefore, all the published studies are carried out using gamma ray (Anger) cameras. The majority of the commercial Anger cameras are made of NaI(Tl) crystal plates. A collimator is used for the determination of the direction of the incident gamma rays to produce a two-dimensional image. The main types are parallel and converging collimators. The converging fan or cone beam collimators produce higher sensitivity but increase the complexity of the data analysis. The collimators for high resolution systems eliminate at least 99.9% of the incident gamma rays. A typical collimator hole is about 1 $mm^2$ in area and ¾" long. Increasing collimator resolution decreases sensitivity, and vice versa. Collimators are made of high atomic number, Z, materials such as lead or tungsten which also produces a considerable amount of scattered gamma rays on the inside surface of the collimator, increasing the scattered photon background. The spatial resolution is limited to about 8 to 12 mm and is expected to reach 6 mm soon. The best energy resolutions at the usual gamma ray energies, applied in these studies, are about 10% which limits their ability of the camera electronics to discriminate against the scattered photon background.

Small gamma ray cameras with dimensions of about 10×10 cm² are being developed at several research institutions. New detectors such as CdTe and CdZnTe are being introduced into this field. Such cameras may be more suitable for scintimammography compared to the full size Anger cameras, because they can be placed closer to the breast due to their small size and are designed to improve spatial resolution somewhat. However, they still require a collimator which keeps the efficiency low. They can only produce two-dimensional images and at least two views are needed to locate the lesion.

The primary radiopharmaceuticals presently studied for scintimammography are Tc-99m SestaMIBI, Tc-99m MDP and Tl-201 Chloride. FIG. 52 lists the Tc-99m and Tl-201 and other possible radionuclides that may be used for malignant tumor detection according to the present invention. Some positron emitters are also included because the 511 keV annihilation photons they produce could be detected by the ScintiMAM both as a single photon mode and/or dual coincident photon, positron emission tomography (PET), mode using two ScintiMAM cameras in coincidence.

Although a large number of interaction mechanisms are known for gamma rays in matter, only two major types play an important role in emission imaging: photoelectric absorption and Compton scatter. These processes lead to the partial or complete transfer of the photon energy to electrons in the detector. They result in sudden and abrupt changes in the photon history. The photon either disappears entirely or is scattered through a significant angle. The photoelectric absorption dominates below about 50 keV for silicon. Silicon is, therefore, an excellent Compton scatterer above 50 keV. In the nuclear medicine energy range of 81 to 511 keV it can be used effectively for the ScintiMAM system.

Figure 53:
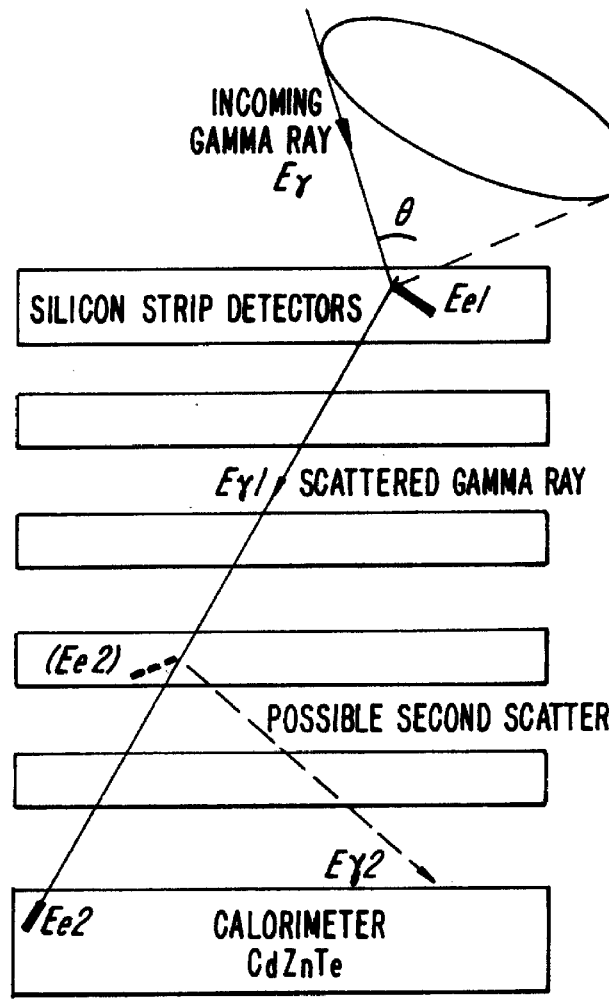
FIG. 53 is an illustration of the double Compton scatter technique used for detecting gamma rays.

Photoelectric absorption decreases exponentially with an increase in energy. This is the dominant interaction in present gamma cameras in the detection of gamma ray photons emitted by radionuclides. Since the incident photon is totally absorbed it is not possible to determine the direction of the incident photon and collimators must be used to determine the direction of origin of the photon. Compton scatter takes place between the incident gamma ray and an electron in the absorbing material. In Compton scatter, the incident gamma ray is deflected through an angle $\theta$ with respect to its original direction (FIG. 53). The photon transfers a portion of its energy to the recoil electron, which was initially at rest. Because all angles of scatter are possible, the energy transferred to the electron can vary from zero to a large fraction of the gamma ray energy. This has been a problem in the detection of gamma rays with energies dominated by the Compton scatter process, since the detected recoil electron alone does not give sufficient information to determine the energy and direction of the incident photon. This angle can be determined by using the double Compton scatter technique (FIG. 53). The total incident gamma ray energy, $E\gamma$, and Compton scatter angle, $\theta$, for the double scatter process are given by:

$$E_\gamma = E_{e1} + E_{\gamma 1}$$

and $$\cos\theta = 1 - mc^2(1/E_{\gamma 1} - 1/E_\gamma)$$

Over the past 20 years this method has been applied to both the detection of gamma rays (1 to 100 MeV) and high energy neutrons with balloon-borne and space detectors and applied for nuclear medical imaging research. FIG. 53 shows the double Compton scatter process. The incident gamma ray first scatters by the Compton process in one of the silicon strip detectors, losing recoil energy $E_{e1}$. The scattered photon continues on until it is absorbed by the calorimeter.

If the second interaction is photoelectric absorption the full energy of the scattered photon is measured and the energy of the incident photon and the scatter angle determined. This is the dominant process for the calorimeter as it is made of high Z material and photoelectric absorption increases exponentially with decrease in the scattered photon energy. Another possibility is that the second interaction can be another Compton scatter where the photon escapes with a small part of the energy. If the energy of the escaping photon is sufficiently low the energy determination is not affected significantly. A calorimeter is placed to surround the sides and the bottom of the silicon strip detector converter as a second scatterer to measure the energy and direction of the Compton scattered photon. Since the calorimeter is a high-Z and high density material, the scattered lower energy photon is fully absorbed with high probability. If the Compton scattered photon makes a second scatter in one of the silicon strip detector planes and then absorbed by the calorimeter as shown in FIG. 53 it is still a good event when full energy of the incident photon is deposited in the detector. The events that do not add up to the full energy of the incident photon are rejected to reduce scattered photon background.

The incident gamma ray direction lies on a cone segment which crosses the field-of-view (FOV) with half-angle $\theta$ whose cone axis is determined by the interaction positions in the top and the bottom detectors. This is because the direction of the scattered electron in the top scintillator is not measured. The Compton scattered electrons with energies 81 to 364 keV are fully stopped within 0.03 to 0.3 mm thickness of the silicon strip detectors, respectively. Therefore, silicon strip detectors with 0.5 to 1.5 mm thickness are ideal for ScintiMAM.

The proposed scintimammography system employs silicon strip detectors. Silicon strip detectors have large areas, excellent energy and position resolution and fast readout. Four inch diameter wafers, typically 300 microns thick with parallel readout strip of $\geq 50$ micron pitch on one side, have been available for several years. Recently up to 1,000 micron thick detectors became commercially available. On the average 1 electron-hole pair is produced per 3.6 eV energy deposited in silicon. The energy deposited by an 80 keV recoil electron fully stopped in silicon is about 22,000 electrons (and holes) which can be collected in <10 ns, leading to <1 ns pulse rise times. Spatial resolutions of <10 microns in one dimension are obtainable by exploiting charge division between adjacent strips. Superimposed on the signal is Gaussian-distributed noise related to detector strip and preamplifier input capacitances. This noise or "equivalent noise charge" (ENC) can be typically 1,000 electrons at room temperature for detector capacitances of about 20 pF. Thus, large signal-to-noise ratios (~22) are obtainable for 80 keV electrons.

Silicon strip detectors have been mainly used in high energy physics experiments to detect minimum ionizing high energy charged particles. The Compton converter in the ScintiMAM detector is new and somewhat different in that the Compton recoil electron loses its entire energy in a single detector wafer of about 1 mm thickness instead of depositing only part of its energy like the minimum ionizing particles. The energy and angular resolutions improve by the increase in the number of the e-hole pairs created in silicon. For a 300 keV recoil electron stopping in silicon, about 83,000 electrons (278 e/keV) are produced with an inherent energy resolution (FWHM/$E_0$=2.35/√N where N is the number of e-hole pairs of 0.8%. For 141 keV electrons stopping inside the silicon wafer the theoretical energy resolution can be calculated to be about 1.2% and stopping distance for the recoil electron about 0.1 mm. The theoretical resolution can be approached in detector application if the input capacitance and preamplifier noise can be kept low. The input capacitance can be decreased substantially by mounting the chips next to the strips or building them on the same silicon.

The individual detector thicknesses can be increased to decrease the number of required planes. The energy resolution of silicon strip detectors is a dramatic improvement over scintillators (e.g. BC-523, 17% at 0.5 MeV).

More recently, double-sided silicon strip detectors with orthogonal strips on opposite sides have been developed. The distinct advantage here is that both x and y coordinates of an interaction are determined simultaneously, within the substrate of a single detector. With single sided detectors, the junction side of a standard p+n diode is segmented into many strips. For double sided detectors, the ohmic side of the n-type silicon wafer is also segmented with orthogonal strips to provide simultaneous readout of the particle impact point. Position resolutions well below 1 mm² on both sides can be achieved. In one embodiment of the ScintiMAM instrument 1 mm thick double sided silicon strip detectors with 1 mm pitch strips orthogonal on the top and bottom surfaces are used. The x and y position of the first two interactions determines the geometry. A combination of all interactions gives the energy and determines the scatter angle.

Figure 54:
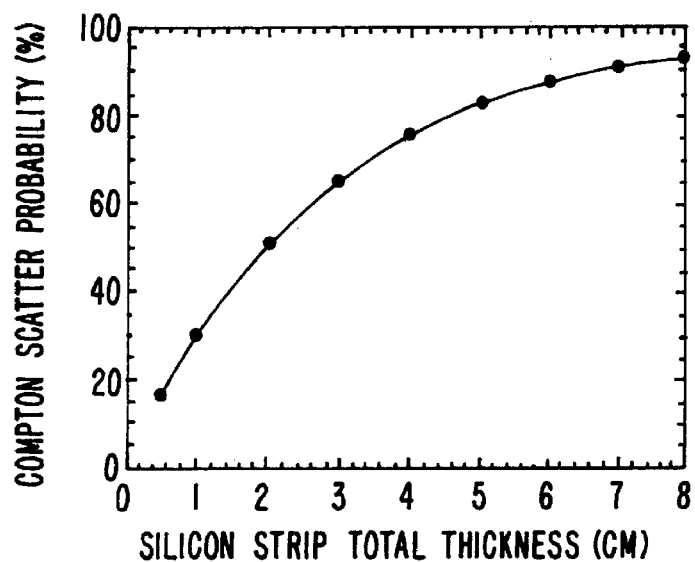
FIG. 54 is a graph illustrating 141 keV x-ray Compton scatter probability against silicon hodoscope total thickness.

The silicon strip detector area for the preferred embodiment of the ScintiMAM detector will be 6.4 cm by 6.4 cm made from 4 inch wafers that are now available. It is anticipated that 10 cm×10 cm detectors from 6 inch diameter wafers will be available in the near future. The results of a simple Monte Carlo calculation using Monte Carlo Neutron Photon (MCNP) software from Los Alamos National Laboratory is shown in FIG. 54. It gives the probability for a 141 keV photon to Compton scatter in varying total silicon thicknesses. For example, about 20% of the 141_keV photons will Compton scatter in a silicon detector 1 cm thick. If 1 mm thick silicon strip detectors are used then 10 planes will be required. For lower energy photons the total thickness required will be lower.

Another important advantage of silicon strip detectors is that they do not need photo multiplier tubes, high voltages or low temperatures. Room temperature functionality is important to produce small size, low power and low cost detectors. They also have strong potential for mass production. However, significant numbers are needed to achieve conversion rates required for high sensitivity. Their small thickness and robustness render them good candidates for low cost printed circuit board (PCB) mounting with front end electronics readout ASIC chips placed next to them. These features could lead to the development of a compact portable scintimammography system.

Figure 55:
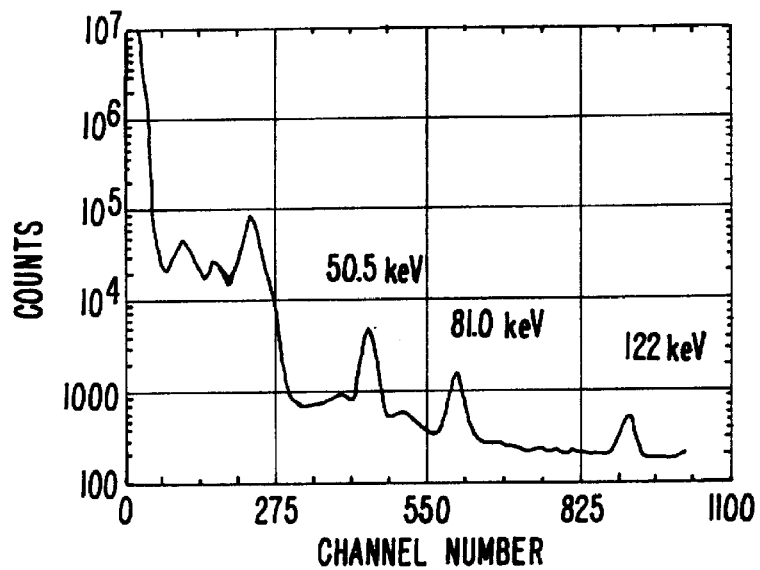
FIG. 55 is a graph illustrating the energy spectrum of a silicon detector at 22° C.

The potential of silicon detector performance was measured for low energy gamma rays using a silicon PIN diode with the same structure and similar detector capacitance as the silicon strip detector. The silicon detector response to gamma rays from 6 to 120 keV was measured. The tests were done at room temperature, 22° C. and the result is shown in FIG. 55, where the energy resolution is dominated by electronic noise. The photopeaks observed have the same FWHM throughout the energy range from 6 to 120 keV. The energy resolution is 3.6 keV for 22° C.

When the detector was cooled to −5° C. it was measured to have 2.2 keV energy resolution. This test has shown that with moderate cooling, silicon strip detectors can achieve an energy resolution of 2.2 keV FWHM for detecting 80–511 keV gamma rays. The temperature measurements demonstrate the high energy resolution capability of silicon detectors.

One of the greatest challenges to the ScintiMAM system is the imaging of Compton double scatter data which is significantly different than the present gamma cameras. The Compton double scatter data gives event cones partially going through the organ under observation. The intersection of these cones produces the image. Although cones are expected to produce a uniform background they also introduce the possibility of three-dimensional imaging with a two-dimensional detector. If an incident photon makes multiple Compton scatters in the silicon converter, the process is over determined if the number of scatters is ≧3. That is the Compton scatter angle and the energy of the incident photon can be determined more than one independent way even if the photon does not deposit its full energy in the silicon converter and escape. Such multiple Compton scatters can also lead to a reduction in the azimuthal ambiguity (event ring) because the Compton scattered photon will be polarized and the third interaction position is dependent on the scattered photon direction.

Recently a new Direct Linear Algebraic Deconvolution (DLAD) method has been proposed. This technique is a modification of the method used successfully in the data analysis of the High Resolution Gamma Ray Spectrometer on HEAO 3 satellite experiment. This technique has excellent potential for application to imaging Compton double scatter data. The present Compton double scatter detectors provide two basic parameters for each event that are related to the incident photon direction, the scattered photon direction and the Compton scatter angle. The DLAD technique makes maximum use of this information.

A concise explanation of the DLAD technique is given here. The reconstruction of the source image from the Compton double scatter data can be represented by the following general formula:

$$D(\chi,\psi,\phi,E) = \int_{\chi,\psi,E}^{I} (\chi_0,\psi_0,E')R(\chi,\psi,\chi_0,\psi_0,\phi,E',E)d\chi_0 d\psi_0 dE' +$$

$$B(\chi,\psi,\phi,E)$$

where $D(\chi, \Psi, \phi, E)$ is the actual Compton scatter data observed by the detector in appropriate coordinates, $\chi$ and $\Psi$ are the coordinates of the rectangular image plane, $\phi$ is the Compton scatter angle and E is the energy of the incident photon, $I(\chi_0,\Psi_0,E_0)$ is the true image of the source and is not a function of the Compton scatter angle, $R(\chi, \Psi, \chi_0, \Psi_0, \phi, E', E)$ is the response function of the detector and $B(\chi, \Psi, \phi, E)$ is the gamma ray background. Normally the calculation is carried out for all energies within the detector sensitivity to determine the total gamma ray flux and for certain energy bands to obtain an energy spectrum. For application to the ScintiMAM system the energy spectrum will be used to discriminate the scattered photon background. The calculation can also be done for different scatter angle bands. D and I are normally referred to as the data and the image spaces, respectively.

For the DLAD method the response function is the concentric rings obtained by mapping the scattered photon direction vector in the image plane. This can be used as an ideal detector response function. The true detector response function, R, can be represented by $$R_{i,j,\phi s} = \epsilon(E, \theta_j, \phi_s) \cdot \Delta_s \cdot PSF \cdot G(\theta_i)$$

where i and j define the bins in the data and image spaces, respectively; $\phi_s$ is the calculated Compton scatter angle as given by Compton scatter formula; $\epsilon$ is the detector efficiency; $\theta_i$ and $\theta_j$ are the incident zenith angles in data and image spaces, respectively; $\Delta\phi_s$ is the scatter angle interval; PSF is the point spread function; and $G(\theta_i)$ is the geometric factor. The PSF is the distribution of the scattered photon vectors in the image plane. The PSF can be represented by a two dimensional normal distribution $$PSF = C(\theta_j, \phi_s) e^{-[(\phi t - \phi s)2/(2\sigma 2(E))]}$$

where C is the normalization constant determined by the requirement that $PSF \times G(\theta_i)$ is equal to 1. The PSF and $G(\theta_i)$ are symmetric in the azimuth. This gives two-dimensional image. ScintiMAM can produce three-dimensional images because of the Compton scatter process. Therefore, either two-dimensional image slices parallel to the converter planes are produced or a direct three-dimensional image can be constructed. The first can be done using above reconstruction technique. The second will be studied during this project.

The DLAD technique can produce fluctuations on the image space that are due to the geometric factor forcing data space to zero at the corners and edges of the field-of-view where the data may be scarce and the Poisson fluctuations are large. This effect can be improved by applying the positivity requirement. The positivity requirement is based on the fact that in image space one cannot get negative fluxes. The positivity constraint has been introduced into DLAD. The new technique is called Constrained Linear Algebraic Deconvolution (CLAD). New tentative results are showing that CLAD is producing much cleaner images than DLAD especially at the edges where the statistics are much worse.

Figure 56:
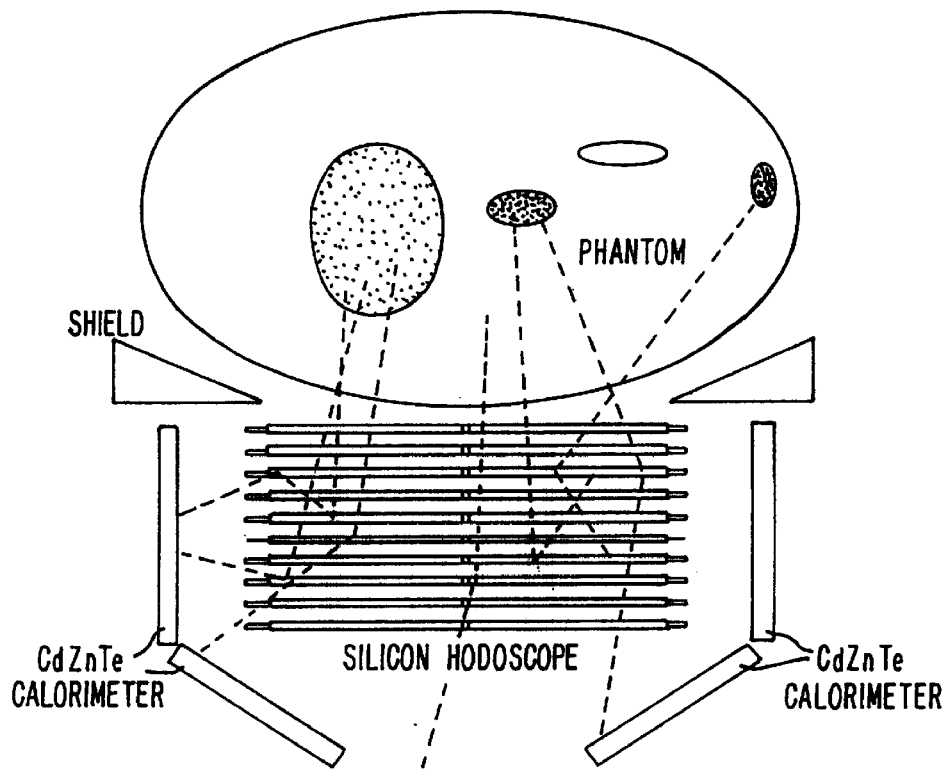
FIG. 56 is an illustration of the side view of one embodiment of the ScintiMAM system.
Figure 57:
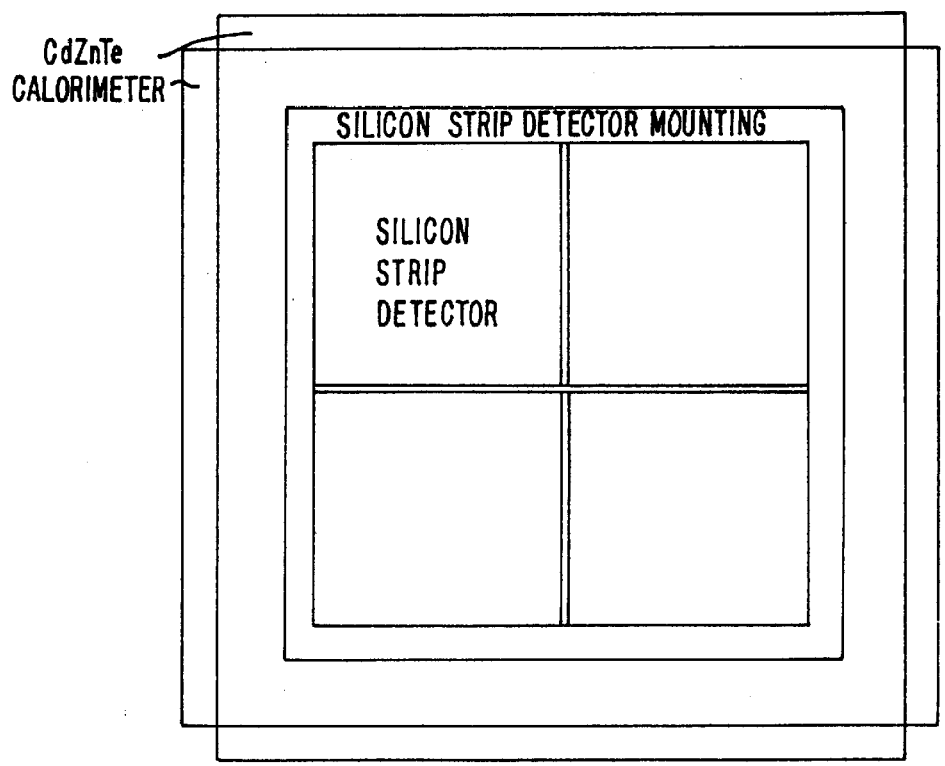
FIG. 57 is an illustration of the top view of the ScinitMAM system shown in FIG. 56.

The preferred embodiment of the ScintiMAM system is planned as a single-head scintimammography system. FIGS. 56–57 illustrate the basic system. The converter is made from 10 planes of silicon strip detectors of thickness varying from 0.5 mm to 1 mm depending on performance and availability. The total Compton scatter probability will vary from 40% for fifteen 1 mm thick silicon strip detectors to about 35% for twenty five 0.5 mm thick detectors. The active area of the silicon strip detectors is increased by mounting four detectors side by side on each plane. The converter height depends strongly on the silicon detector plane separation. If 1 mm thick detectors are used, then the plane separation is about 0.5 cm and the converter height about 5 cm. These values are tentative and the thickness of silicon detectors and separation will be optimized during this project.

CdTe or CdZnTe detectors have higher energy resolution than CsI(Tl) crystals especially for low energy gamma rays. Therefore, the calorimeter is made from about 2 mm thick CdTe or CdZnTe pad detectors.

A single layer of calorimeter is placed around the converter as shown in FIGS. 56–57, as close as possible, without degrading the angular resolution significantly by introducing additional error from geometric combination of pixels. The gap at the bottom is due to the energy threshold of the silicon detectors which is expected to be $\geq 5$ keV. The incident photons that deposit energy less than the threshold energy will not be detected in the converter and such small angle scatters need not be stopped at the calorimeter. This will reduce the calorimeter cost. One such event is demonstrated in FIG. 56. A shield is placed in front of the calorimeter to decrease the background count rates. The geometry, strip pitch, thickness, shielding and the size of the gap at the bottom of the calorimeter may be optimized by Monte Carlo simulations. Lead or tungsten shielding placed around the calorimeter shields the instrument from the body and especially the heart which uptakes substantial amounts of Tc-99m SestaMIBI and Tl-201. Preferably the ScintiMAM instrument is positioned to reduce background.

Figure 58:
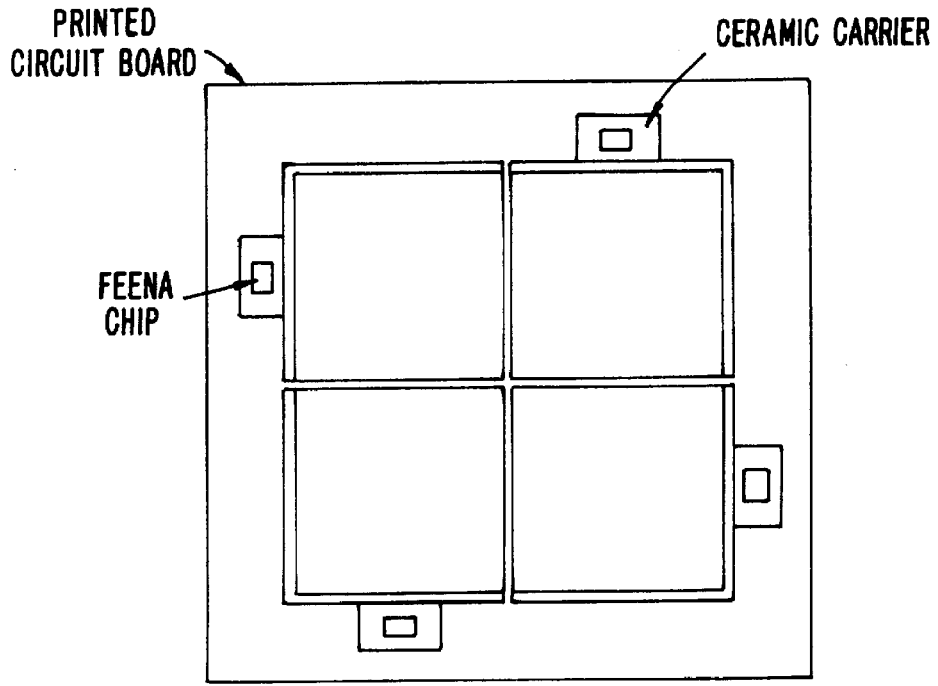
FIG. 58 is an illustration of the FEENA readout chips and the silicon strip detector planes mounted on a PCB.

The new FOXFET biased silicon strip detectors with 6.4 cm×6.4 cm active area and up to 1 mm thickness are now available. Each plane of the converter is made from four such silicon strip detectors mounted as close to each other as possible to increase the active area by a factor of 4 (FIGS. 56–58). This will give an active area of 12.8 cm×12.8 cm equal to about 164 cm². The converter has ten detector planes with 0.5 cm separation. The silicon strip detectors are mounted on a printed circuit board (PCB) or a ceramic holder. The front end electronics (FEENA) readout chips are mounted on the PCB in nearly touching distance to the silicon strip detectors as shown in FIG. 58. The fan in from strip pitch to FEENA chip pad pitch is done on the silicon strip detector for reliability and ease of ultrasonic wire bonding. The FEENA chip can be used in the wafer form to reduce mass near the converter. Most of the electronics are assembled outside the detector and only the most essential components are placed on to the PCB. Small size surface mount components are used on the PCB to reduce mass. Miniaturized connectors and cables are used to interface to the data acquisition system.

The silicon strip detectors are designed and fabricated using the new FOXFET AC coupling technique on both the junction and ohmic sides. This technique improves the signal quality especially at the ohmic side because the bias resistor formed through the FOXFET technique is much larger than with other techniques. It also eliminates external capacitances and resistors which become bulky, require large real estate and are costly when large numbers of channels are used. Preferably high radiation resistant FOXFET silicon strip detectors are used which significantly increases the reliability of the ScintiMAM.

FOXFET silicon strip detectors are commercially available and show excellent response to low energy photons 81 to 511 keV required by the ScintiMAM system. The major improvement is expected to be achieved by lowering the dark current and reducing the junction thickness to decrease strip capacitance. This is expected to reduce the detector and electronic noise and improve energy resolution which in turn will enhance the spatial resolution.

The small size of the active area and the dividers between the four silicon strip detectors at each plane will not cause any problem such as truncating the sides or producing gaps in the image. This is because the disclosed technique inherently has a large field of view and the detector active area can be smaller than the imaged organ. Also any gaps or dead strips in the converter cannot produce gaps in the image. Smaller active area, small number of dead strips at each plane and gaps in between the silicon strip detectors can only slightly reduce the detection efficiency and does not effect the image. This is the result of the Compton scatter technique and is expected to eliminate image defects, increase the reliability and tolerance to defects and reduce production cost.

The calorimeter is preferably fabricated using the newly developed CdZnTe pad detectors. These detectors have excellent energy resolution for 10 to 300 keV gamma rays. Therefore, CdZnTe is especially useful to work with $^{99m}$Tc and $^{201}$Tl, the most commonly used radionuclides.

The origin of CdZnTe is the cadmium telluride (CdTe) detector. CdTe contains relatively high atomic numbers (48 and 52) with a large enough bandgap energy (1.47 eV) to permit room temperature operation. It has a density of 6.06 gr/cm$^3$ and the energy required to create a single electron-hole (e-h) pair is 4.43 eV. The hole mobility is about a factor of 30 lower than the electron mobility. The hole life times are also very short due to the low mobility because the effects of trapping and recombination are enhanced. The hole collection efficiency improves with the purity of the material used. The probability of photoelectric absorption per unit path length is approximately a factor of 100 times larger than in silicon for typical gamma ray energies. For example, it is opaque to low energy x-rays for thicknesses in the range of a mm. Its energy resolution is not comparable to silicon detectors for low energy x-rays, because of the poor hole collection efficiency. The energy resolution measured for CdTe detectors is about 3.5 keV at 122 keV at room temperature.

Problems with CdTe detectors appear to be related to a large degree to the practice of growing CdTe detector by the traveling heater method (THM), using Te-rich solutions. THM crystals must be doped with an element such as Cl to achieve high resistivity, and chlorine doping has been associated with detector operating instabilities (counting rate polarization) and long-term reliability problems. Also, THM crystals are generally of small volume and have rather low yields of detector grade material, which leads to high detector prices. More fundamentally, the CdTe bandgap of 1.47 eV limits resistivities to the low-109 ohm-cm range, resulting in relatively large room temperature dark currents.

The CdZnTe detectors were developed by Aurora Technologies Corporation (ATC) (now called DIGIRAD) and eV Products to improve the CdTe detectors they were manufacturing as gamma ray detectors. They added up to 20% high purity ZnTe to CdTe to obtain $Cd_{1-x}Zn_xTe$ ($x \leq 0.2$). ATC has developed a new high pressure Bridgman (HPB) approach to growing detector quality crystals of CdZnTe. HPB crystals are quite large (up to 10 cm in diameter and 10 kg), have yields of detector grade material of over 70%, and exhibit uniform near-intrinsic resistivity without doping. Detectors fabricated from HPB grown crystals exhibit excellent stability, reliability and lifetime. Furthermore, the HPB process can be used to grow high quality crystals of $Cd_{1-x}Zn_xTe$ throughout the entire alloy composition range. Alloying ZnTe with CdTe increases the bandgap, resulting in much higher resistivities and correspondingly lower leakage currents than CdTe.

Figure 59:
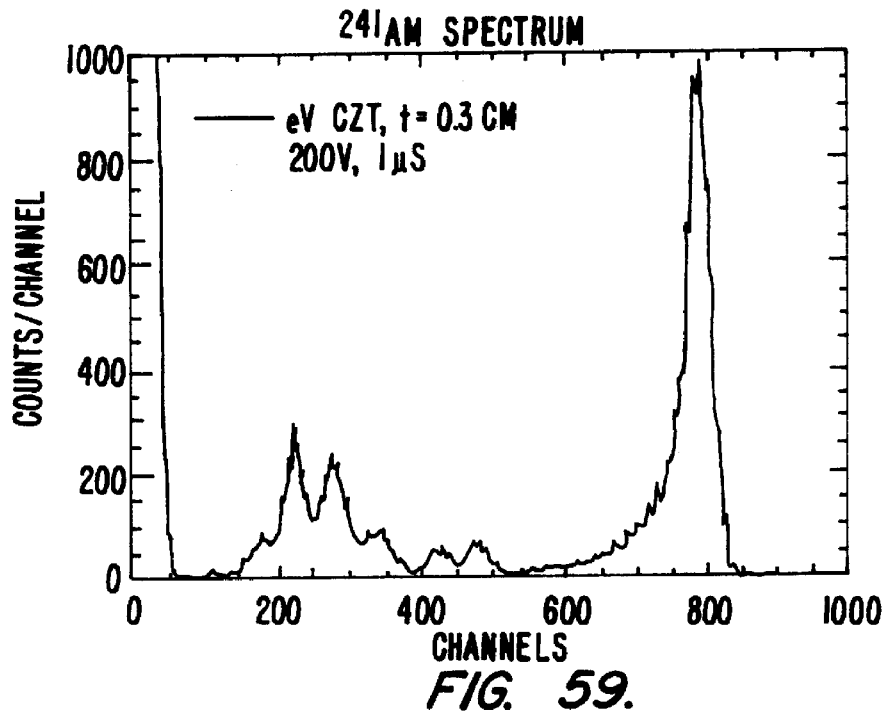
FIG. 59 is a graph illustrating the energy spectrum of a 241 Am source observed by a CdZnTe (CZT) detector at 25° C.
Figure 60:
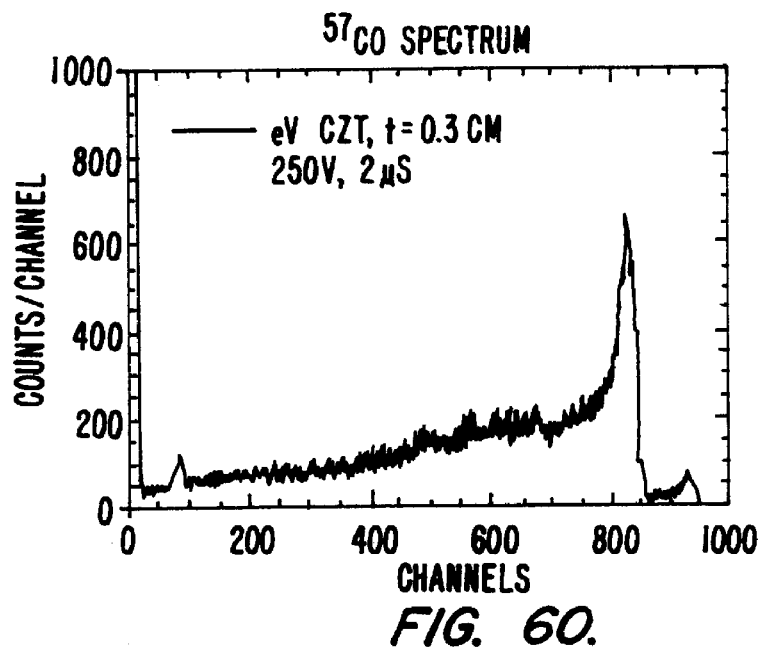
FIG. 60 is a graph illustrating the energy spectrum of a 57 Co source observed by a CdZnTe (CZT) detector at 25° C.
Figure 61:
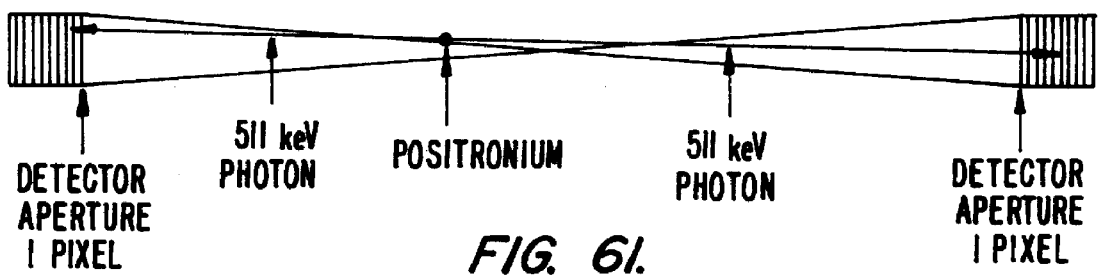
FIG. 61 is an illustration of the positron emission tomography (PET) detection principle.

The energy resolution of CdZnTe detectors to 10 to 300 keV energies is important for the proposed prototype scintimammography system. FIG. 59 shows the energy spectrum of an Americium-241 source and a CdZnTe detector with 1×1 mm$^2$ size pads. The x-rays at 13.9, 17.7, 20.8, 26.4 and 59.5 keV (with its escape peaks from characteristic K shell x-rays from Cd at 36.5 keV and Te at 32.5 keV) are clearly seen with good energy resolution. The slight low energy tail observed for the 59.5 keV peak is typical of that observed with CdZnTe detectors and is due to incomplete charge collection for some of the events. The energy spectrum of $^{60}$Co (main peak at 122 keV) obtained by a 2 mm thick CdZnTe crystal with same pad size is shown in FIG. 60. The low energy tail is clearly seen at higher energies. Good energy resolution is also claimed by some authors even at 511 keV energies. The CdZnTe pad detectors are expected to be superior to CdZnTe double sided strip detectors as only the electrons need to be collected. There are new techniques becoming available recently such as the LBNL method for reducing the hole trapping effect, the low energy tail, and obtaining much improved energy resolution.

The FWHM uncertainty in the cone half-angle, $\Delta\theta$, due to a detector of finite energy resolution (FWHM), $\Delta E_{e1}$ and $\Delta E_{e2}$ at first and second scatter planes can be calculated using the Compton scatter formula:

$$\Delta\theta = \frac{mc^2}{E_\gamma^2 \sin\theta} \left\{ \Delta E_{e1}^2 + \left[ \frac{E_\gamma^2}{E_{\gamma 1}^2} - 1 \right]^2 \Delta E_{e2}^2 \right\}^{1/2}$$

where mc$^2$ gas the electron rest energy (511 keV), $\theta$ is the Compton scatter angle and $E_{\gamma, \text{ and } E\gamma 1}$ are the incident and scattered photon energies. The energy resolution due to the statistical fluctuation for electrons stopped inside silicon strip detectors varies from 1.3% at 100 keV to 0.75% at 350 keV using the formula. The electronics noise of the detector is about 2 keV. Therefore the total energy resolution will be dominated by the electronics noise which is same for both the converter and the calorimeter. The angular resolution is calculated with energy resolution of 2 keV (FWHM), where $\Delta\theta$, for forward scattered gamma rays ($\theta<90°$) varies from 5° at $\theta=30°$ to about 3.2° at $\theta=70°$ for 141 keV ($^{99m}$Tc) incident photons. For example, the same calculation carried out for the 364 keV $^{131}$I gamma rays give angular resolutions of approximately 1° from $\theta=20°$ to 90°. At a distance of 2.5 cm (at the center of the compressed breast) these angular resolutions produce effectively 2.2 to 1.4 mm spatial resolutions for 141 keV and 0.4 mm for 364 keV gamma rays. The geometric angular resolution, $\Delta\theta_{Geom}$, which gives the axis of the image cone, depends on the silicon strip detector pixel size and the distance between the first two scatters. The FWHM value can be calculated similar to that for a collimator. Normally the geometric angular resolution is kept much smaller than the scatter angle variation, which depends strongly on the energy resolution as shown above. It is easier to adjust the geometric angular resolution in a silicon strip detector as the pixel dimensions can be as small as 25 microns. The pixel size for the simulated model was 1 mm$^2$. The average distance between the first two interactions is about 10 cm, which translates to 0.5° geometric angular resolution.

One Tc-99m SestaMIBI injection dose is about 20 mCi. A breast takes up about 1%, or about 100 $\mu$Ci. With proper shielding, assuming 1 mCi (3.7×10$^7$ photons/s/4$\pi$str) is in the view of the detector aperture. The detector solid angle will accept about 20%. Therefore, 8×10$^6$ photons/s will enter the detector aperture. Each 1 mm thick silicon plane is about 2% efficient, therefore the count rate will be 160 kHz/silicon plane. The CdZnTe calorimeter count rates will be about same (300 kHz and can be lowered by shielding). The increase in efficiency is partially compensated by the decrease in the area and the solid angle. This is a relatively low count rate per module and should be easily accommodated with conventional high speed data acquisition electronics.

Each silicon strip detector will be read out directly through a multi-channel front end electronics (FEE) readout chip with self trigger output and sparse readout capability. A fast logic system and the coincidence requirement ($\geq 2$ interactions) can eliminate most of the unwanted events. The good events can be accumulated into a fast memory or FIFO buffer for imaging by a fast host computer. Each event can be time tagged for event reconstruction and/or dynamic imaging (MUGA) studies.

The energy resolution is expected to be about 2.5% for a 141 keV photon with 1,000 electrons ENC noise. This is an estimation assuming that the 141 keV photon produces a substantial Compton scatter in the first scatter plane (converter) and the recoil electron is fully absorbed in the same wafer. The scattered photon is also fully absorbed at another plane or calorimeter. The energy resolution decreases with decreasing energy. The angular resolution depends strongly on the energy resolution as given by the Compton double scatter formula. The expected angular resolution of one embodiment of the ScintiMAM system is about 2° to 3° for 141 keV photons. The distance from the detector front face to the center of the silicon strip detector converter is about 2.5 cm. The spatial resolution at the center (5 cm from converter center) of a gently compressed breast of 5 cm thickness is about 1.8 to 2.6 mm, respectively. The position of the lesion (the peak of the distribution) can be determined more precisely than the FWHM spatial resolution which could be useful for locating small size tumors.

An important technological requirement for this system is a multichannel front end electronics chip (FEENA) with self trigger output to readout the silicon strip and CdZnTe pad detectors. The preferred FEENA chip has 64 channels and is designed as a mixed signal ASIC CMOS chip. Each channel of the chip consists of an analog section and a digital section. The input from the silicon strip detector comes directly into a low noise charge sensitive amplifier. The output of the charge sensitive amplifier goes into an optional inverter and a shaper amplifier. The inverter enables the use of both positive or negative input signals. A two stage trigger circuit consists of two comparators before and after the shaping amplifier. The first one provides a fast trigger signal with small timing jitter through a high precision threshold level. The second trigger signal is slower than the first but has high pulse height accuracy and is used to label the channels that have a signal. The fast triggers from all channels are sent to an OR circuit to produce the external trigger output to signal the external readout interface that an event has occurred and the chip contains valid data. There are three readout modes for the chip: 1) a sparse readout mode which allows the readout of only the strips that have a signal, 2) a nearest neighbored readout mode which allows the readout of the strips with a signal and the two nearest neighbors, and 3) an all channel readout mode which allows the readout of all the channels of the chip in sequence. It also has 4 different peaking times (200 nsec to 4 msec) for application to detectors with different speeds such as fast silicon strip, CdZnTe detectors and slow CsI(Tl) crystals. The noise performance of the present chip is about 1,000 e (noise equivalent charge: NEC) per 20 pF input capacitance, and the maximum readout speed is 1 MHz.

Since both radiopharmaceuticals were develop as heart imaging agents, the heart of the patient takes up significant quantities of Tc-99m MIBI and Tl-201. This will produce a major background if it is in the field-of-view of the detector. One method of reducing background from heart liver and spleen is to let the patient lie down with one breast at a time hanging from a hole in the observation table and to image the breast from inside (center of the chest) to outside of the body. The detector should be well shielded from all directions except the front face using lead or tungsten of sufficient thickness. This technique should eliminate significant amount of background photons. Many of the events can be eliminated as background in the image formation, since they will be placed outside the breast due to the large first scatter angle. The backscattered gamma rays coming outside the detector aperture can also be eliminated as the energies they deposit at the first and second scatters will show that they have backscattered using the constraint imposed by the Compton double scatter formula. This can be done efficiently for incident photon energies <250 keV.

The existence of the positron was predicted by P.A.M. Dirac in 1928 as a particle identical to the electron, but occupying a state of negative energy. In 1932 Carl Anderson observed this particle experimentally. The positron is the antiparticle of the electron which has the same mass but opposite charge. Some radionuclides reduce their excessive positive nuclear charge by the emission of positrons. After a positron is emitted from a radionuclide it loses its kinetic energy through a series of ionizations and excitations in matter until it slows down and forms an atom-like structure called "positronium" with an electron. Positronium has a very short life time, $10^{-10}$ s for para state, and annihilates into a pair of photons in the para state or into 3 photons in the ortho state. Most of the annihilation radiation comes from the para state (99.7%) since the ortho state has to go through a forbidden transition. Since both the electron and the positron are nearly at rest, to conserve energy and momentum, the two photons fly off in opposite directions in a nearly perfect straight line, each carrying an energy of about 511 keV which is the rest mass of electron and positron. There is a slight noncollinearity of about $180°\pm0.25°$ due to the small but finite energy of the positronium just before annihilation. In PET the presence of positrons in tissues is observed through the detection of the annihilation radiation generated and it is the simultaneous emission of two photons travelling in opposite directions that renders this process so effective.

FIG. 62 shows some of the positron sources used as radiotracers in PET. Since most of these sources are radioactive counterparts of normal constitutes of living beings they are excellent for the production of radiopharmaceuticals. Their short life-times are also useful in administration of large doses without the risk of significant radiation exposure to the patient. The short life-times necessitates PET study location to be near accelerators where the radiopharmaceuticals are produced. The Fluorine-18 is the radio tracer of choice since it has the shortest range of 2.4 mm in the body tissue and the longest life-time of 109.7 min.

Although a large number of possible interaction mechanisms are known for photons in matter, only three major types play an important role in radiation detection: photoelectric absorption, Compton scattering, and pair production. All these processes lead to the partial or complete transfer of the photon energy to electron. They result in sudden and abrupt changes in the photon history, in that the photon either absorbed entirely or is scattered through a significant angle. Photoelectric absorption dominates below about 50 keV. Compton scattering becomes important from 50 keV and stays the dominant process up to 10 MeV, where pair production takes over. At 511 keV the important detection process is Compton scattering for the first interaction. The liklihood of photoelectric absorption increases as the as the energy of the scattered photon decreases. When scattered photon energy is below 50 keV, photoelectric effect starts to become the dominant process. Therefore, PET systems based on silicon strip detectors work in the Compton scatter region.

In the photoelectric absorption process, a photon undergoes an interaction with a target atom in which the photon is completely absorbed. In its place, an energetic photoelectron is ejected from the one of its atomic bound shells. The interaction is with the atom as a whole and cannot take place with free electrons. The photoelectron appears with an energy $E_e$ given by $$E_c = h\nu - E_b$$

where $E_b$ represents the binding energy of the photoelectron in its original shell and hv is the incident photon energy. For photon energies of more than 100 keV, the photoelectron carries most of the original energy. For silicon strip detectors this process is important for only low energy photons of 0.5 to 80 keV. Photoelectric absorption increases nearly exponentially with the decrease in energy. Photoelectric absorption for CsI(Tl) becomes important below 400 keV.

Figure 63:
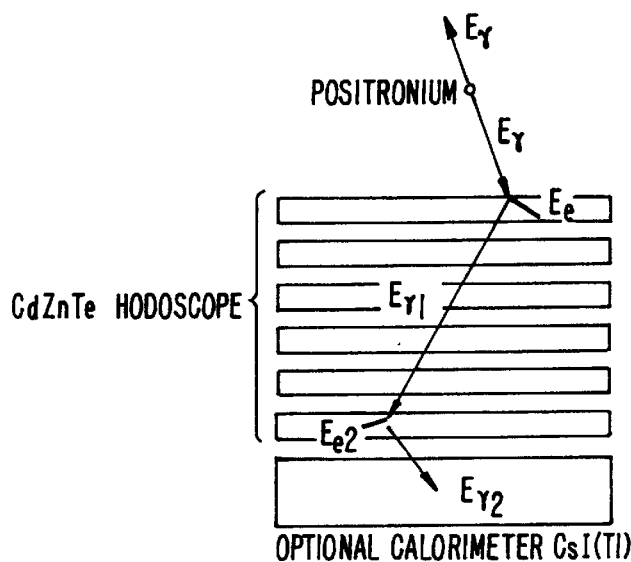
FIG. 63 is an illustration of a Compton double scattering technique for detecting photons.

Compton scattering takes place between the incident photons and an electron in the absorbing material. In Compton scattering, the incident photon is deflected through an angle θ with respect to its original direction. The photon transfers a portion of its energy to the recoil electron initially at rest. Because all scattering angles are possible, the energy transferred to the electron can vary from zero to a large fraction of the photon energy. This has been a problem in the detection of photons by the Compton scattering process since the detected recoil electron alone does not give sufficient information to determine the energy and direction of the incident photon. This has been solved by the Compton double scattering technique as shown in FIG. 63. The total incident photon energy and Compton scattering angle for the double scattering process are given by:

$$E_\gamma = E_{e1} + E_{\gamma 1}$$

and $$\cos\theta = 1 - mc^2(1/E_{\gamma 1} - 1/E_\gamma)$$

There is no need to determine the direction of the incident photon in PET detectors because the direction of the annihilation photons are determined by the geometry of the coincidence technique.

The incident photon first scatters by the Compton process in one of the silicon strip detectors, losing recoil energy $E_{e1}$. The scattered photon continues on until it interacts in another silicon strip detector. If the second interaction is photoelectric absorption the full energy of the scattered photon is measured and the energy of the incident photon and the scattering angle determined. This is the dominant process for low photon energy. Another possibility is that the second interaction can be another Compton process where the photon escapes with a fraction of its energy. If the energy of the escaping photon is sufficiently low the energy determination is not affected significantly. If there are a sufficient number of silicon planes the escaped photon makes further interactions in subsequent planes and gets fully absorbed. All the energy measured after the second scatter is added to the energy of the second scatter, $E_{e2}$, to correct for the missing energy. If only a few silicon planes are used, a calorimeter can be placed behind the silicon strip detectors, without position resolution, to catch the escaping photons and correct $E_{e2}$ for accurate incident photon energy and the scattering angle determination. Since the calorimeter is made from a high-Z and high density scintillator such as CsI, the escaping low energy photon is fully absorbed with high probability. The events that do not add up to the full energy of the incident photon, 511±5 keV (±26 keV with optional calorimeter), will be rejected to reduce background.

The Compton recoil electrons with energies up to 511 keV are fully stopped within 0.85 mm silicon. Therefore, silicon strip detectors ≧1 mm thickness are ideal for the ComPET system. Same energy electrons has much smaller range, on the order of 0.1 mm, in CdZnTe.

Figure 64:
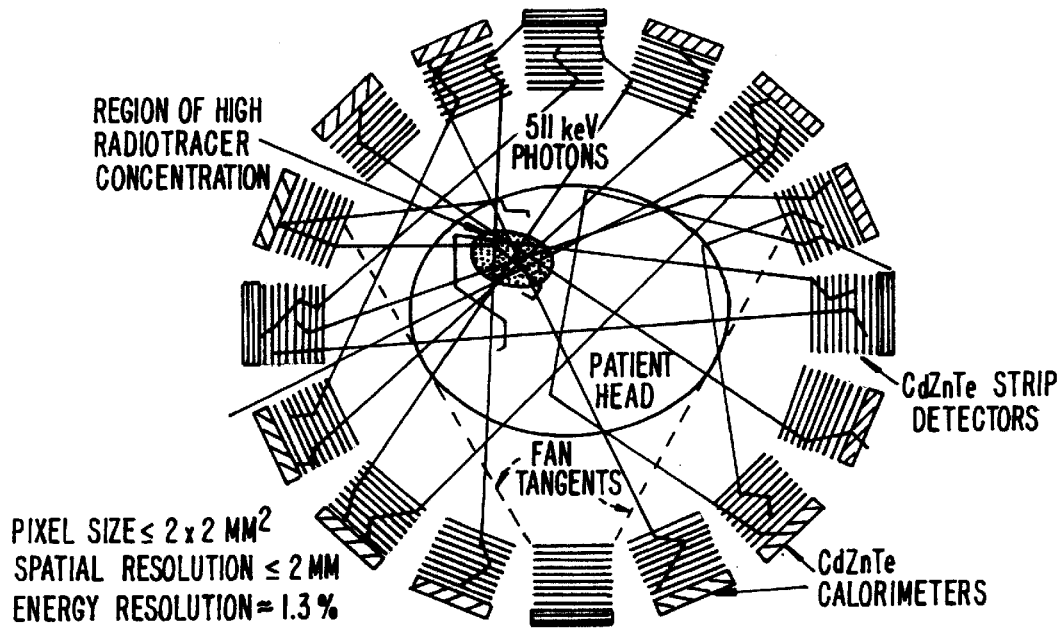
FIG. 64 is an illustration of the cross-section of a ComPET device according to one embodiment of the invention.

An emdodiment of the ComPET system is shown in FIG. 64. The drawing is not to scale and only shows the broad features. The first interaction point in the CdZnTe strip detectors gives the coordinates of the Compton interaction within 2×2 mm² pixel size if the strips are orthogonal to each other on opposite sides of the double sided CdZnTe strip detectors and have 2 mm pitch. The coincident detection in two different detector banks define the positron annihilation photon pair chord. CdZnTe strip detector planes placed in nearly touching distance between each other reduce detector depth. The size of the silicon wafers can be increased progressively in the radial direction to reduce the gap between each detector bank or the CdZnTe strip detectors can be placed overlapping each other by increasing the plane separation.

In FIG. 64, photon pairs are created inside the patient tissue from positron annihilations and detected in the CdZnTe strip detectors by undergoing Compton scattering and photoelectric absorption. Also shown are several photons scattered inside the tissue which produce the scattered photon background. Some photons are absorbed in the body and produce the γ-ray attenuation that can be corrected by well known methods. These background photons have lower energies because of initial scatterings and are rejected as described above. Occasionally photons will make more than one Compton scattering in a CdZnTe strip detector bank. These are legitimate events as the full energy of the photon is measured by adding the energies observed at each interaction point. Some photons may escape with significant energy after the last interaction. These events will be rejected as scattered photon background. The stopping power of the whole detector can be matched to that of BGO crystals in two ways: increase the number of CdZnTe strip detectors (higher cost but excellent energy resolution), or put a calorimeter plane at the back of the CdZnTe strip detectors (lower cost lower energy resolution). The ComPET instrument can also be made in an elliptical or curved shape to fit the contours of the human body because the 2×2×2 mm³ voxel size virtually eliminates the radial elongation of PSF. The detector can be protected from photons coming from different parts of the patient by using a lead shield around the outer perimeter on both sides.

The coincidence setup follows the fan angle technique. Tangents are drawn from each detector bank to the organ under study as shown in FIG. 64. The banks which are covered by the fan beam are put in coincidence with the originator. The smaller number of banks, about 16, make this complex technique feasible. Similar coincidence schemes are devised in commercial PET systems by combining several adjacent BGO crystals in groups to reduce the complexity of the electronics.

Figure 65:
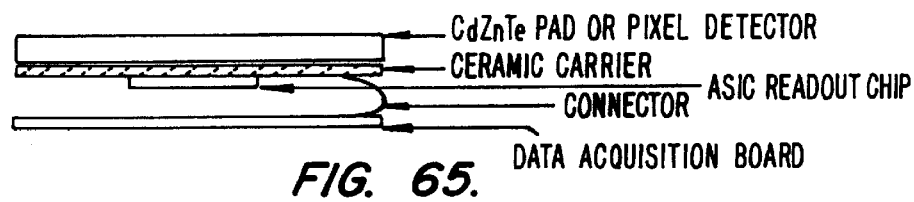
FIG. 65 is an illustration of the side view for a single module for the two dimensional gamma camera.

The origin of Cadmium Zinc Telluride (CdZnTe) is the Cadmium Telluride (CdTe) detector. CdTe contains relatively high atomic numbers (48 and 52) with a large enough bandgap energy (1.47 eV) to permit room temperature operation. It has a density of 6.06 g/cm² and energy required to create a single electron-hole (e-h) pair is 4.43 eV. The hole mobility is about a factor of 30 slower than the electron mobility. The hole life times are also very short due to the low mobility because the effects of trapping and recombination are enhanced. The hole collection efficiency improves with the purity of the material used. The probability of the photoelectric absorption per unit pathlength is approximately a factor of 100 times larger than in silicon for typical gamma ray energies. For example, it is opaque to low energy x-rays for thicknesses in the range of a mm. Its energy resolution is not comparable to silicon detectors for low energy x-rays, because of the poor hole collection efficiency. The energy resolutions measured for CdTe detectors are 3.5 keV at 122 keV and 8 keV at 661 keV at room temperature. Better results have been obtained recently. CdZnTe and CdTe detectors can be made strip, pad and pixel (FIGS. 65–66) forms. CdZnTe strip detectors (FIGS. 65–66) have orthogonally placed strips on both top and bottom sides. This arrangement gives both the x and the y coordinates of the interaction. However, ambiguity of the position of the interaction can happen if more than one interactions occur inside the detector simultaneously. A two dimensional array of pads (larger pixel size) or pixels can also be made. Pads or pixels are placed on one side of the detector. This arrangement has no positional ambiguity problem for any number of simultaneous events. However, more data channels must be readout.

Problems with CdTe detectors appear to be related to a large degree to the practice of growing CdTe detector by the travelling heater method (THM), using Te-rich solutions. THM crystals must be doped with an element such as Cl to achieve high resistivity, and chlorine doping has been associated with detector operating instabilities (counting rate polarization) and long-term reliability problems. Also, THM crystals are generally of small volume and have rather low yields of detector grade material, which leads to high detector prices. More fundamentally, the CdTe bandgap of 1.47 eV limits resistivities to the low-$10^9$ ohm-cm range, resulting in relatively large room temperature leakage currents.

The preferred detectors are CdZnTe detectors by ATC to improve the CdTe detectors they were manufacturing as gamma ray detectors. They added up to 20% high purity ZnTe to CdTe to obtain $Cd_{1-x}Zn_xTe$ ($x \leq 0.2$). ATC has developed a new high pressure Bridgman (HPB) approach to growing detector quality crystals of CdZnTe. HPB crystals are quite large (up to 10-cm in diameter and 10 kg), have yields of detector grade material of over 70%, and exhibit uniformly near-intrinsic resistivity without doping. Detectors fabricated from HPB grown crystals exhibit excellent stability, reliability and lifetime. Furthermore, the HPB process can be used to grow high quality crystals of $Cd_{1-x}Zn_xTe$ throughout the entire alloy compostion range. Alloying ZnTe with CdTe increases the bandgap, resulting in much higher resistivities and correspondingly lower leakage currents than CdTe.

Growth of $Cd_{1-x}Zn_xTe$ and other wide bandgap II–VI compound crystals crystals from the melt is generally complicated by relatively high melting temperatures and vapor pressures and the fact that the melting temperatures are comparable to or exceed the softening temperature of quartz. These crystals are often grown in sealed quartz ampoules, but the incorporation of oxygen and other impurities from quartz near its softening point can cause significant contamination, even with the use of carbon coatings. A major advantage of the HPB process is that the high gas pressure reduces diffusion and evaporation of charge; this eliminates the need for sealed ampoules and permits a choice of crucible materials.

The internal components, such as crucibles and heaters, of the ATC furnace are manufactured from high purity graphite. A specially designed heater provides a temperature profile optimized for Bridgman growth. Crucible travel is effected by a high pressure mechanical feedthrough. The furnaces can accommodate crucibles with internal diameters up to 10 cm and growth charges up to 10 kg. The furnace parts are enclosed in a large steel shell designed to withstand pressures in excess of 100 atm. The furnaces can be operated to temperatures above 1,600° C.

The starting elements for crystal growth are multiply purified and weighed out to stoichiometric compositions. No impurity dopants such as Cl are added to the charges. The complete crystal growth cycle requires about one month. Several furnaces are available for volume production at ATC.

$Cd_{1-x}Zn_xTe$ crystals have been grown for the entire range of $0 \leq x \leq 1$ by the HPB method. FIG. 68 summarizes characterization data for crystals with $x \leq 0.2$, the limit for which high quality radiation detectors have been produced. It also shows the comparison of the properties of the CdTe and $Cd_{1-x}Zn_xTe$ detectors. The data in FIG. 68 are representative averages of many samples.

Resistivities are remarkably uniform throughout a boule, varying approximately ±20% over wafers cut transverse to the growth direction and ±50% over longitudinal slices. Achievement of near-intrinsic resistivities without the introduction of dopants may be related to growth at the metal-tellurium stoichiometric composition.

Etch-pit-density (EPD) is a measure of the density of lattice defects in a crystal. Values in FIG. 68 are significantly lower than those typically reported for crystals grown in sealed quartz ampoules and used in the infrared detector industry as substrate material.

Double crystal rocking curves (DCRCs), provide another measure of lattice perfection. The values in FIG. 68 are quite narrow, another indication of low defect content. Low temperature photoluminescence (PL) spectra exhibit bright, sharp emission lines in which free and bound excitons are clearly visible; all of the major lines are accompanied by sharp LO-phonons. These observations are indicators of high structural quality and low impurity concentrations. It is noteworthy that commonly observed deep level emissions associated with oxygen and native defects are absent in all compositions, including ZnTe. The increase in linewidth with x is attributable to alloy broadening; the linewidth for ZnTe is typically 0.12 mev.

The resistivity values of FIG. 68 show a major advantage of $Cd_{1-x}Zn_xTe$ over CdTe for x-ray detection. In addition to high room temperature resisitivity, the wider bandgap resulting from alloying ZnTe with CdTe leads to improved performance at elevated temperatures.

A 10° C. drop from the room temperature reduces the leakage current by about a factor of 10. Small temperature changes such as 10° to 20° C. can be achieved using electronic coolers such as the Peltier devices.

The results show that $Cd_{1-x}Zn_xTe$ detectors, especially $Cd_{0.8}Zn_{0.2}Te$, is a major improvement over CdTe detectors. These values and the evidence for low impurity concentrations and high crystalline quality make $Cd_{1-x}Zn_xTe$ an attractive detector material. Furthermore, the ability to produce large, homogeneous boules raises interesting new prospects, such as 1) fabrication of large area detector arrays for the ComPET system and 2) large-quantity, low-cost detector manufacturing which could make the ComPET instrument cost effective high performance solution for the replacement of the present PET systems.

Figure 69:
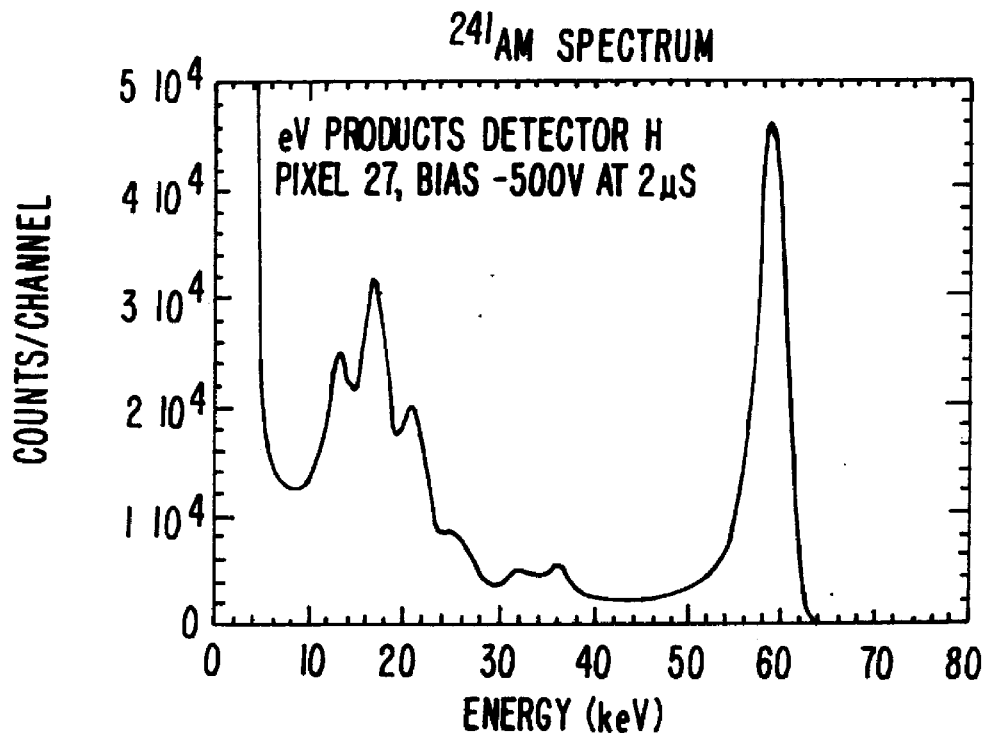
FIG. 69 is an illustration of the energy spectrum of an Americium-241 source observed by a CdZnTe detector.
Figure 70:
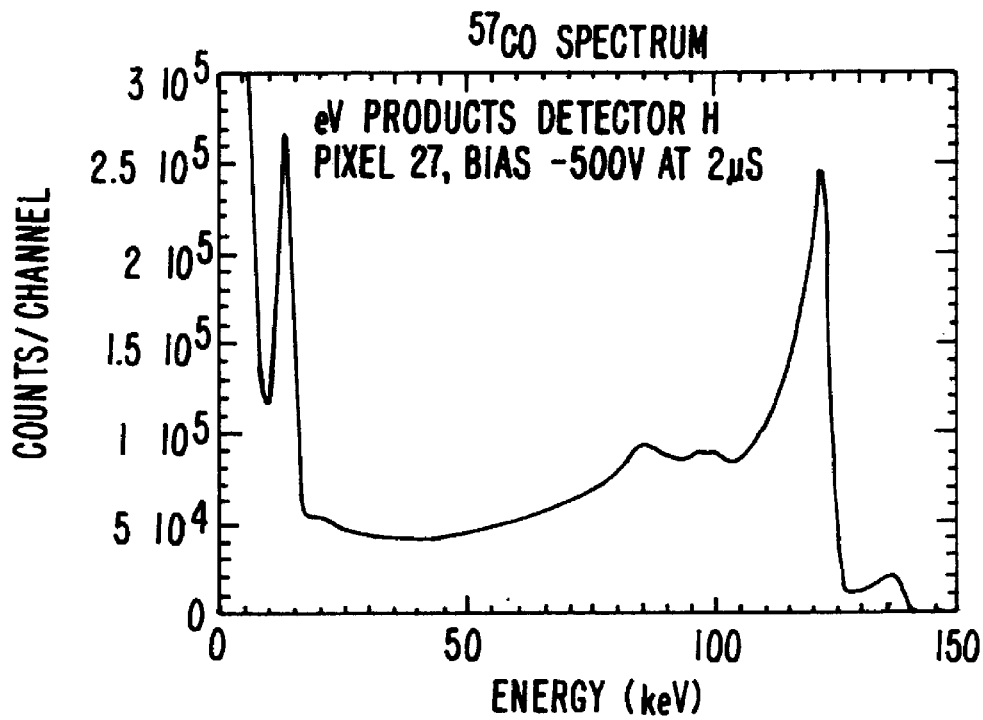
FIG. 70 is an illustration of the energy spectrum of a Cobalt-57 source observed by a CdZnTe detector.

The energy resolution cannot be applied for the ComPET system as it will be used in the current mode. However, the energy resolution at 15 to 20 keV energies will be important to show the capability of the proposed CdZnTe pixel detectors. FIG. 69 shows the energy spectrum of a Americium-241 source with CdZnTe detector. The x-ray emission at 13.9, 17.7, 20.8, 26.4 and 59.5 keV (with its escape peaks from characteristic K x-rays from Cd at 36.5 keV and Te at 32.5 keV) are clearly seen with good energy resolution. The low energy tail observed for the 59.5 keV peak is typical of that observed with CdTe detectors and is due to incomplete charge collection for some of the events. This effect is not seen at the energy range important for this application, 15 to 20 keV. This is because the x-ray penetration into the crystal substrate is very small and the holes are readily collected as they are created near the surface. This is only true if the x-ray beam is incident from the direction of the negative bias side (where the holes are collected). The electrons have much higher mobility and life time, therefore, they are not effected by the penetration depth.

A preliminary model for the ComPET system as given in FIG. 64 is simulated to demonstrate its capabilities. MCNP (Monte Carlo Neutron Photon) Version 4.2 is used. It is a general purpose continuous energy Monte Carlo code developed at Los Alamos National Laboratory. The MCNP has evolved over the last 25 years in the Radiation Transport Group at LANL in their study of the interactions of neutrons and photons with matter. It is specifically designed for modelling radiation detectors and is well known for its accuracy.

The inner and outer radii of the simulated PET are 15 and 25.8 cm respectively with 6 cm axial length. The phantom at the center is the standard 20 cm diameter 20 cm long cylinder filled with water and 1 $\mu$Ci/cc 511 keV $\gamma$-ray source. Double sided CdZnTe strip detectors of 3 mm thick and 1 mm strip pitch are modelled in cylindrical form. All together 36 planes are placed inside a detector bank with zero separation between planes. The total thickness is 10.8 cm corresponding to 89% Compton scattering probability. The 511 keV photons produced isotropically in the phantom are tracked along their paths until they are fully absorbed or escaped from a detector bank. A 10 keV detection threshold is imposed. Another Monte Carlo calculation was carried out with a CsI(Tl) calorimeter behind the CdZnTe strip detectors and reducing the total thickness of the CdZnTe strip detectors, to find how much reduction in the silicon thickness can be made without changing the sensitivity significantly. The results of this work show that the total silicon thickness can be reduced by a factor of 3 if a CsI(Tl) calorimeter of 3.4 cm in thickness is employed. Other Monte Carlo analysis may be carried out for other detector geometries to optimize the ComPET system in terms of spatial and energy resolutions, volume/line/point source sensitivity, size and cost.

Figures 71, 73:
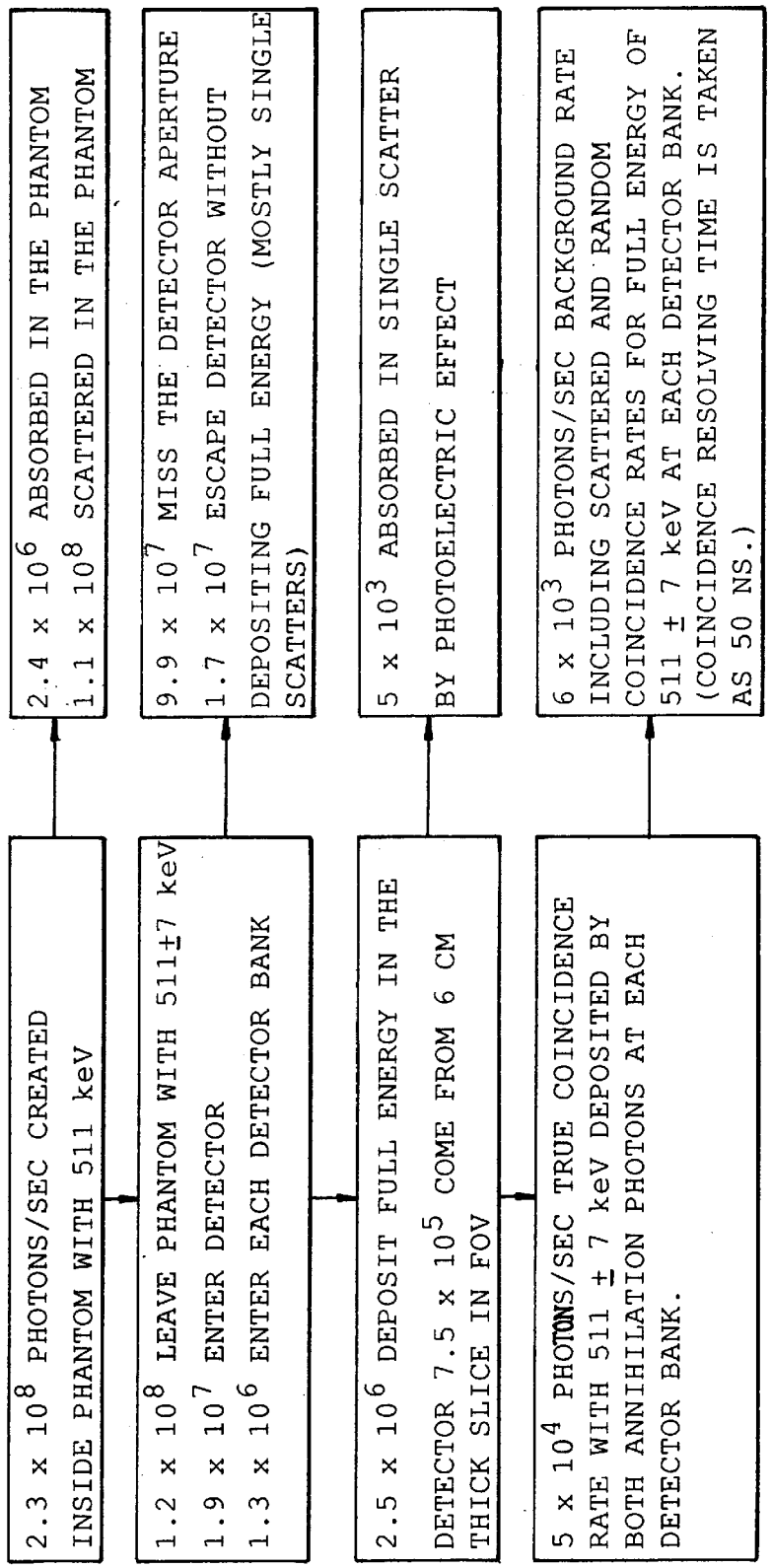
FIG. 71 is a flowchart illustrating the Monte Carlo photon history for an embodiment of the ComPET system with true and background coincidence rates.
FIG. 73 is a table comparing the sensitivities of a ComPET detector with the S9100B Brain Scanner from GE Medical Systems.

The history of the 511 keV photon is traced using the arrangement described above without the calorimeter. The results are shown in FIG. 71 calculated for one of the annihilation photons only. Probabilities must be multiplied for coincidence rates of the 511 keV photon pair. The 511 keV photons scattered in the phantom are effectively discriminated utilizing the high energy resolution. It leads to a significant reduction in the scattered photon background which decreases the random coincidence rate, because only the photons which deposit full energy in each detector bank will be required to form a coincidence with the corresponding detector banks within its fan angle. The Compton backscattering, 90°<$\gamma$<180°, probability for 511 keV photons is only a few percent compared to forward scattering, 0<$\gamma$<90°.

The Monte Carlo analysis shows that $1.9 \times 10^7$ photons/sec out of $2.3 \times 10^8$ enter the ring detector of 6 cm axial length. About $1.7 \times 10^7$ photons/sec makes single interaction (singles) with the detector. If 6×6 cm$^2$ area CdZnTe strip detectors are used, there will be at most 16 banks. The singles rate per bank will be $1.1 \times 10^6$ photons/sec. Since the Monte Carlo analysis is based on 36 detector planes per bank, the singles rate for each CdZnTe strip detector is 30,000 photons/sec. Such rates are not excessive for CdZnTe strip detectors which produce about 20 ns long pulses with no significant tail. However, the charge sensitive amplifier system may have a tail, which has to be minimized for this particular application. The detector dead time is expected to be less than 1 ms. Since the other CdZnTe strip detectors are alive while one or more of the detectors are busy reading out data, the effective dead time for the whole system is much shorter than 1 ms.

High count rates are also encountered for CdZnTe strip detectors that are used as vertex detectors in many high energy physics experiments. This problem is solved by establishing high level parallelism in readout electronics for which the CdZnTe strip detectors are highly suitable. One possible way is to divide the detector into many radial sections or banks as shown in FIG. 64 and read each bank separately. If it is divided into 16 banks, readout rate at each detector bank will be about 1.1 MHz. The data rate will be even smaller due to some loss of events between the detector banks and at the edges when the photons go through thinner silicon material. This will also reduce sensitivity somewhat unless such events can be recovered by the electronics.

Highly integrated parallel electronic data acquisition system is required to readout the 540 CdZnTe strip detectors. Preferably each CdZnTe strip detector has 60 strips, 30 on each side for x and y coordinates. This means 32,400 strips to readout. Reading out so many channels one by one is a problem. However, this problem is solved by using a high density ASIC chip directly connected to the strips. It reduces readout task to about 2 to 3 channels per detector bank. The resulting readout channels of about 1,600 is approximately equal to the number of BGO crystals used in present PET systems with several rings.

One of the most important factors to consider in uncollimated PET systems is the scattered and random coincidence rates. If the detector design and electronics readout system is not optimized for large event rates required in nuclear medicine the detector can be swamped by random coincidences and dead time loses, which severely limit true coincidence rate. The high energy resolution of the proposed design is expected to cut scattered and random coincidence rates significantly.

The true coincidence rate can be calculated by using the Monte Carlo results. The probability of a 511 keV annihilation photon escape from the phantom is $P_1$=0.99, to have full energy, 511±7 keV, is $P_2$=0.52, to enter detector aperture with the full energy is $P_3$=0.16 and to deposit 511 keV within energy resolution is $P_4$=0.13. The 6 cm axial length of the 20 cm phantom within the field-of-view (FOV) of the detector ring can produce true coincidence events. Therefore, a further factor of $P_5$=0.3 must be used. The probability of detecting a single 511 keV photon with full energy deposition in the detector is given by $P_s = P_1 \cdot P_2 \cdot P_3 \cdot P_4$. The true coincidence rate is therefore, given by $P_c = (P_1 \cdot P_2 \cdot P_3 \cdot P_4) \cdot (P_1 \cdot P_2 \cdot P_4) \cdot P_5$. The $P_3$ must be omitted in one of the expressions due to the collinearity geometry of the annihilation photon pair. The calculation shows that the probability to detect single 511 keV photon is $P_s$=0.011. The true coincidence probability is calculated to be $P_c$=0.00022 which gives the true coincidence rate as $5 \times 10^4$ photons/sec.

The random coincidence rate $R_a$ can be calculated using the rate $R_1$ in one of the detector banks, $R_2$ the singles rate within the fan angle of the bank selected and connected in coincidence and the coincidence resolving time $\tau$ ($\tau$=2T, where T is the input pulse width). $R_a$ is given by $$R_a = R_1 R_2 \tau = 2 R_1 R_2 T$$

A coincidence resolving time $\tau$ of 50 ns (down to 20 nsec is possible) can be assumed as a conservative estimate. If the proposed ring type detector's internal diameter is 30 cm then there will be about 16 detector banks of 6×6 cm² CdZnTe strip detectors surrounding the patient as shown in FIG. 64. Each bank will have about 6 other detector banks in coincidence within its fan angle. The energy resolution will allow discriminator level for each detector bank to be set at about 490 keV well within the energy resolution of 511±7 keV. Monte Carlo results show that when these conditions are applied the total count rate in the ComPET system will be about $7.5 \times 10^5$ as shown in FIG. 71. Here, the rate coming from the 6 cm thick slice of the phantom is used because the detector ring will be shielded as much as possible for photons coming from other parts of the phantom. Since two photons are produced per positron annihilation this rate has to be multiplied by 2. Then the singles rates can be calculated to be $1 \times 10^5$ photons $s^{-1}$ and $6 \times 10^5$ photons $s^{-1}$, for $R_1$ and $R_2$, respectively. The random coincidence rate is $R_a \sim 3 \times 10^3$ photons $s^{-1}$. The scattered coincidence rate is usually about equal to the random coincidence rate (Budinger et al., 1979), therefore, the total background coincidence rate is about $6 \times 10^3$ photons $s^{-1}$, which is about 12% of the true coincidence rate. If the coincidence resolving time can be reduced to ~20 ns similar to most commercial PET systems then the background coincidence rate will reduce to about 5%.

This reduction in the total background coincidence rates comes from the higher energy resolution of the ComPET detector. The commercial PET systems that use BGO crystals have total scattered and random coincidence rates of about 20% to 40% of the true coincidence rate. This is because BGO has about 20% energy resolution for 511 keV photons and the discriminator threshold used is about 400 keV if set to FWHM value or about 300 keV if set to FWTM value of the energy resolution. This allows more scattered photons with lower energy to fall into the coincidence window. The results given here are first order preliminary calculations to show the potential of the ComPET system.

Figure 72:
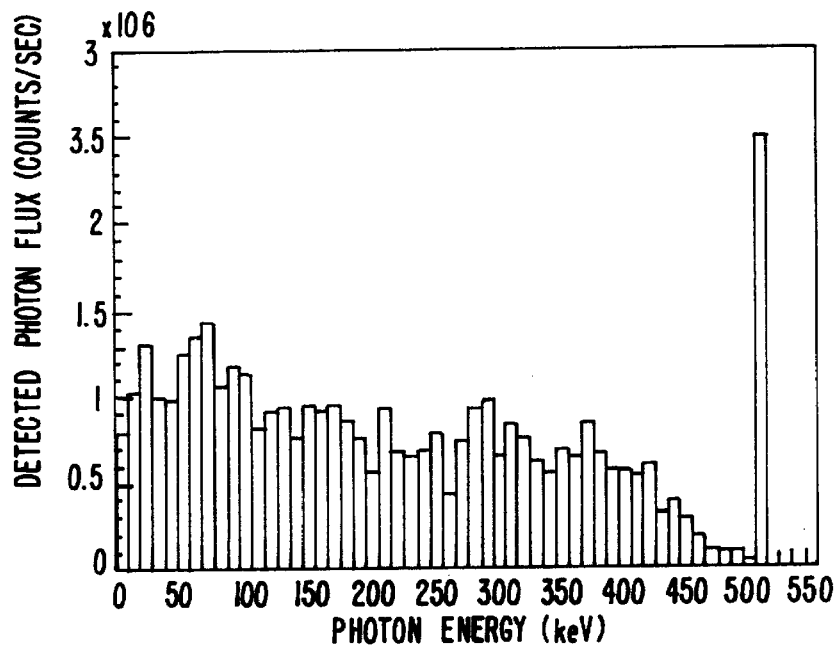
FIG. 72 is an illustration of the energy spectrum of 511 keV photons generated inside a phantom and detected by a ring type ComPET detector.

FIG. 72 shows the energy spectrum of the detector calculated by the MCNP Monte Carlo program for the photons that come from the phantom and make more than 2 interactions in the detector. The spectrum shows a clear multiscattering peak for full energy deposition within about 1.3% expected total energy resolution for 511 keV photons. The partial energy deposition in the detector and detection of the low energy photons already scattered in the phantom are seen as the distribution below the 511 keV peak.

The straight plane (slice) sensitivity of the simulated detector is about 8,300 Cts $s^{-1}$ $(\mu Ci/cc)^{-1}$ $cm^{-1}$ found by using the true coincidence rate ($5 \times 10^4$ cts $s^{-1}$) and normalizing the length of the detector to 1 cm slice thickness. Although, the pixel size and slice thickness of the proposed detector are about 2 mm, the detector can be divided into 1 cm slices for comparison with available systems. Commercial PET instruments such as S9100B brain scanner by GE Medical systems claim 8,700 Cts $s^{-1}$ $(\mu Ci/cc)^{-1}$ straight plane sensitivity. The straight plane sensitivity of the proposed detector is close to a BGO based detector sensitivity. A comparison of the ComPET system with the S9100B brain scanner from GE Medical Systems is given in FIG. 73.

The sensitivity of the ComPET instrument depends strongly on the amount of silicon used and can be improved further by increasing the number of the silicon detectors planes. The number of CdZnTe strip detectors can be also decreased by a factor of 3 without changing the calculated sensitivity by adding a calorimeter layer behind the silicon microstrip detectors to reduce cost. The spatial and energy resolutions, uniform true 3-dimensional imaging capability with $2 \times 2 \times 2$ mm³ voxel size, elimination of the radial elongation of point spread function and low background coincidence rate are significant improvements over present PET systems.

The spatial resolution in general depends on the detector pixel size, Anger logic, photon noncollinearity, radial elongation, and reconstruction algorithm. The technique of the present invention completely eliminates the radial elongation and does not use Anger logic. The effect of the detector pixel size on the spatial resolution is given by the strip pitch on the x and y planes and the separation or the thickness of the double sided CdZnTe strip detectors. One embodiment of the invention uses double sided CdZnTe strip detectors (or pad detectors) with about 1 mm pitch on both sides and 1 mm thickness as shown in FIG. 67. Therefore, at the first scatter point, the location of the incoming photon is known to 1 mm³ accuracy. The design is very flexible. The pitch can be increased to improve SNR. Since detector pixel size is flexible, the main contribution on the spatial resolution comes from photon noncollinearity and finite positron range which is physically unavoidable. However, a new technique was introduced recently that can mathematically reduce the positron range blurring effect. If the new technique is effective it may be advantageous to reduce the ComPET system voxel size and spatial resolution to 1 mm³ and reduce positron range blur during image enhancement by applying this technique.

The 1 mm strip pitch that will be used in the desktop model could be finer than the spatial resolution limitation due to the photon noncollinearity and the finite position range. Therefore, the strip pitch can be increased to 2 mm if SNR becomes too low by summing data from the adjacent strips.

Figure 74:
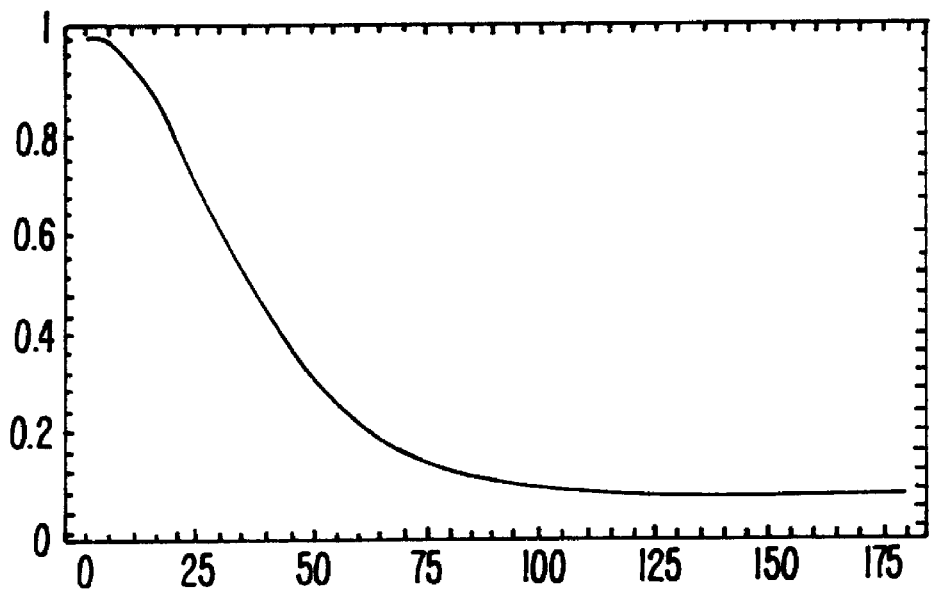
FIG. 74 is an illustration of the differential Compton scattering cross section ($d\sigma/d\theta$) vs. scatter angle.
Figure 75:
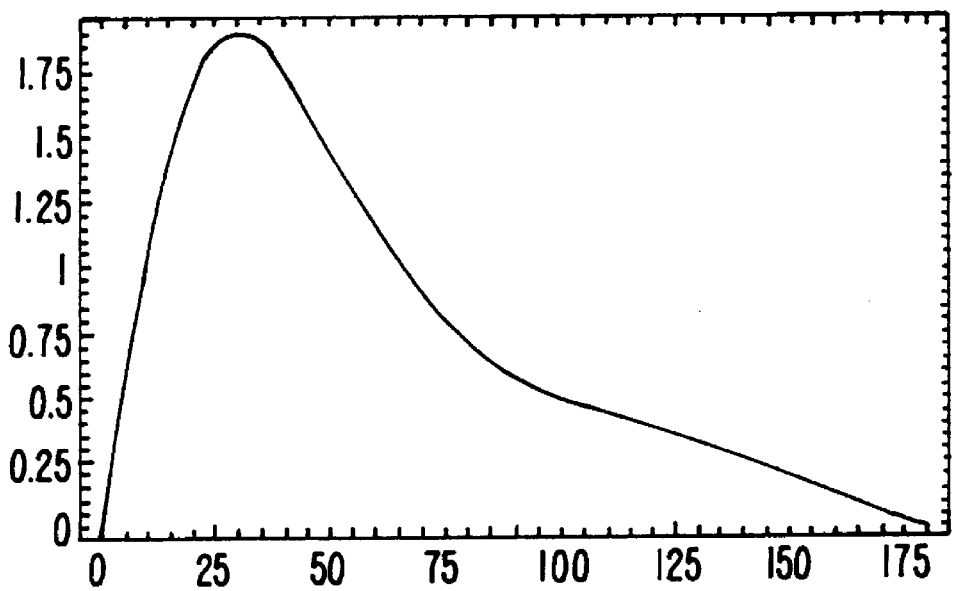
FIG. 75 is an illustration of the cross section ($d\sigma/d\theta$) vs. scatter angle.

FIG. 74 shows the differential Compton scatter $(d\sigma/d\Omega)$ cross section against scatter angle. The cross section is normalized to 1 at 0 degree scatter angle. It shows that the Compton scatter takes place mostly in the forward direction for 511 keV gamma rays. FIG. 75 shows the Compton scatter $(d\sigma/d\theta)$ cross section against scatter angle. Total cross section in the forward direction is 1.916 and total cross section in the backward direction is 0.449. The cross section peaks around 30° scatter angle.

There are many possible embodiments of the ComPET system. In the embodiment of the system shown in FIG. 64 the ComPET aperture is surrounded with many layers of CdZnTe strips, pads or other position sensitive detectors (CdZnTe hodoscope). Thicker detectors with thicknesses from a few millimeters to a few centimeters are placed at the back and at the sides of these detectors (CdZnTe calorimeter) to absorb most of the escaping photons after they make one or more Compton scatter inside the CdZnTe strip pad detector layers (CdZnTe hodoscope). Septa can be used at the sides and/or in front of the detector aperture as required.

Figure 76:
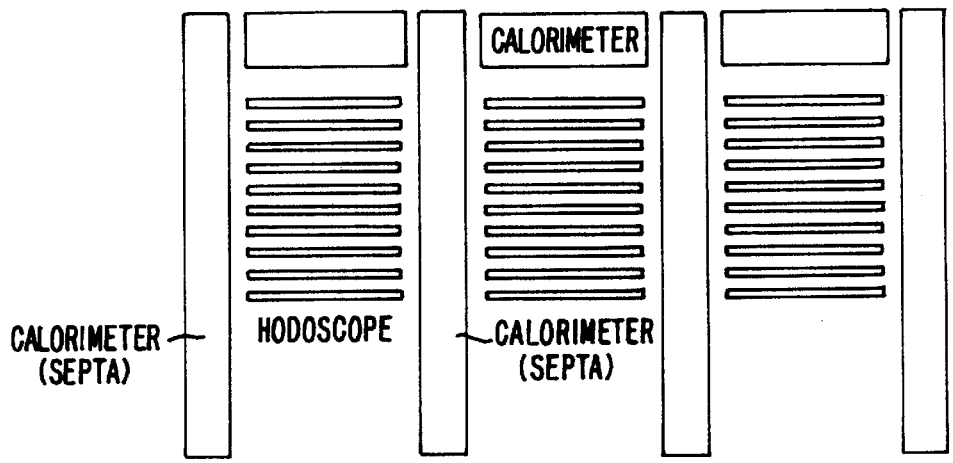
FIG. 76 is an illustration of the cross section of a possible detector geometry with the strip detector hodoscope planes surrounded by thicker calorimeter detectors which can also be used as active septa for ComPET.

In another embodiment of the above geometry the hodoscope can be built in many layers of narrow strips of few milimeter to few centimeter wide surrounding the patient. The thicker detectors (calorimeter) can also be made in rings placed on both sides and the back of the hodoscope. Then several hodoscope/calorimeter rings can be placed side by side to produce slices. The calorimeters can be made to stick outwards infront of the hodoscopes similar to the normal septa and can be used as active septa. The calorimeter rings in between two hodoscopes can also be made in single layers if effective. FIG. 76 shows an approximate schematics for this arrangement.

In another embodiment the detector can also be built from individual modules, hodoscope surrounded by calorimeter with only the input aperture is open, placed around the patient. The modules may surround the patient completely or two, four, six, eight or more even number of modules can be placed with each pair on opposite sides of the patient at 180° and rotated to form the tomographic images.

Figure 77:
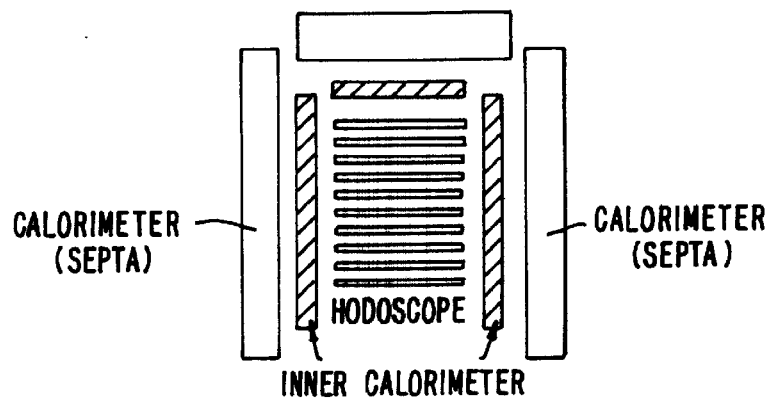
FIG. 77 is an illustration of the cross section of a detector module with inner and outer calorimeter sections.

In another embodiment, the calorimeter may be built from two sections. A thinner inner detector facing the hodoscope and a thicker outside detector (FIG. 77). The inside detector can be made from CdZnTe strip or pad detectors to produce fine position resolution. Outer detectors can be thicker and may have fine or low spatial resolution. The calorimeter and hodoscope are shown in rectangular structure but in actual implementation they can have any shape, for example they can be curved into spherical or parabolic configurations to maximize the efficiency, sensitivity, angular and energy resolutions.

If active or passive septa arrangement is not used than a complete three-dimensional tomographic image can be produced and slices through the patient. In the three-dimensional tomographic images slices through the patient can also be made but this time at any angle the physician wants and not restricted to only the 90° slices to the axis of the patients body or organ under study in present PET systems.

The electronic data acquisition system will measure the energy deposited in the CdZnTe strip detectors and the positions of the interaction points. Custom monolithic VLSI circuits with 32 to 64 channels per chip placed adjacent to the CdZnTe strips can provide the charge storage and sequenced data readout. The front end electronic (FEE) ASIC chips can be designed to have sparse readout system so that only the channels which have valid data will be digitized and stored to save time.

A trigger output by the FEE chip to flag the arrival of an event is essential for application to PET. The trigger output will allow the readout electronics to service the detectors in parallel when they detect an event. Such a fast readout ASIC chip with trigger capability and sparse readout significantly simplifies the electronics and reduces the readout dead time. The output of the ASIC chips in turn may be combined as required to further integrate the detector electronics.

Fast and parallel data acquisition systems such as Fastbus, VME (VXI), and CAMAC ADC and TDC modules with up to 100 channels input per module may be used with the ComPET system. The Fastbus and VXI bus systems have a lower price/channel than others and have the advantage of 32 bit data transfers at about 30 MHz. An on-line computer collects data, carries out preliminary analysis, selects events and produces an image of the results on the screen.

Figure 78:
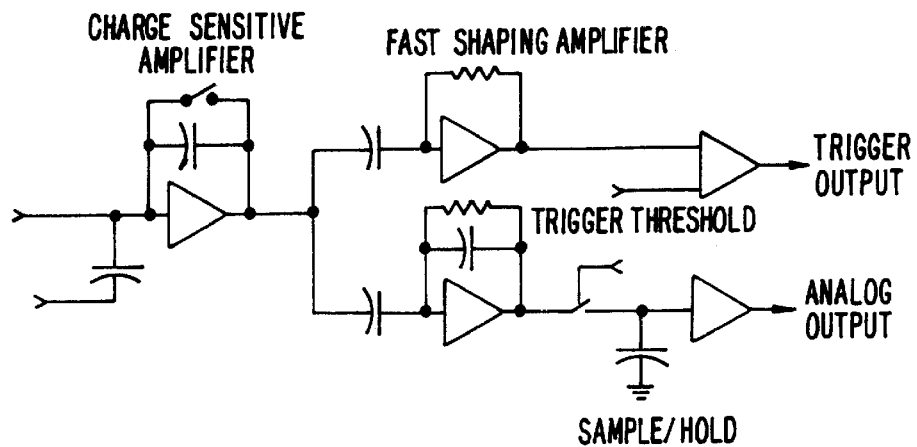
FIG. 78 is a conceptual schematic diagram of a single channel of the front-end electronics chip.

FIG. 78 is an illustration of a single channel of a front-end electronics chip which can integrate 64 channels low noise charge sensitive amplifiers with self-trigger and calibration capability on each channel to provide timing information with better than 20 ns precision. The trigger threshold can be adjusted to provide energy descrimination. This device also has a spare readout function (only readout the channels above a set threshold) to provide fast data acquisition capability. This front-end chip provides an easy interface to a data acquistion system to handle the high data rate of the ComPET detector system.

Figure 79:
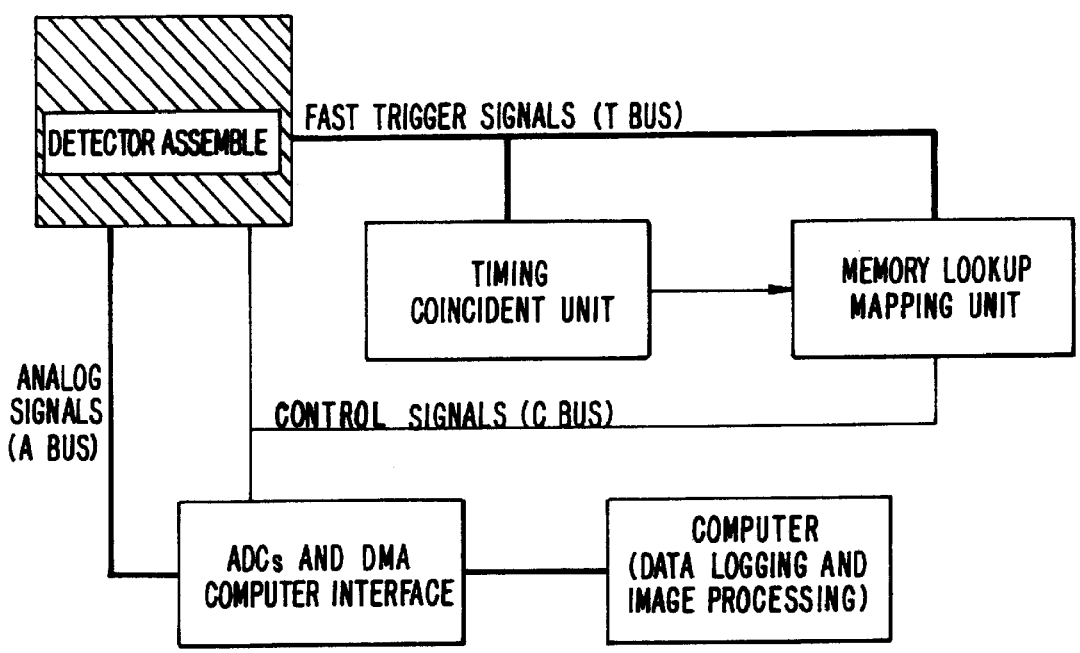
FIG. 79 is a conceptual design of the data acquisition system.

A concepture design of the ComPET detector data acquisition system is shown in FIG. 79. The front-end electronics chip will integrat with detector assembles. Each assemble unit will provide fast trigger signals (on T Bus) and analog output signals (on A Bus). A timing coincident unit can detect the coincident of any two detector assemble units within 20 ns window. If there is a coincident, the addresses of the coincident pair will feed through a memory lookup table to insure that the coincident meet the geometry requirement. Only after all the above requirements are met, controls will be send to ADCs and detector assembles to record the data of the two coincident detector assembles.

This three level design of the data acquisition system can provide minimum readout dead time at a relatively low cost. The fastest speed requirement is the coincident unit, which will run with 50–100 MHz speed to provide nearly dead time free processing capability for the expect total interaction rate. However because of its simple function, it can be build with reasonable cost. At this level, a good event is required two hit coincident with in 20 ns, and both pass a set threshold. This required can reduce the event of factor 10 over the incident rate. The next level, memory lookup unit, required more complex function, however, the rate here will be reduced because of the coincident requirement. The addresses of the coincident detector assembles are feed through a lookup memory which can be program to require the detector pair meet certain geometry conditions. For example, they have to have some body of interested in between them. This can reduce the scatter photons significantly. Different lookup memory tables can be made for different kind of examinations and they can be reprogram by loading different memory table to the unit. Once a event passes both timing coincident and geometry conditions, a readout sequince will start for the ADC system to readout the two detector assembles have the coincident hits. At this point, the event rate has be reduced significantly, so a precision ADC system can be implemented to record the energy information with high precision. This is required if the high energy resolution of the CdZTe detector can be utilized. The high precision energy information can be used later in the imaging reconstruction stage to further reduce the scattering photons effect. Because of the layer design of the detector assemble, the data on each layer can be readout in parallel. The estimated speed to readout one pair of coincident detector assembles is half micro-second. This speed is choose to suit the acceptance and efficiency of the detector system. Because of the layer design of the ystem, increase speed can be made by adding more ADC modulars.

As will be understood by those familiar with the art, the present invention may be embodied in other specific forms without departing from the spirit or essential characteristics thereof. Accordingly, the disclosures and descriptions herein are intended to be illustrative, but not limiting, of the scope of the invention which is set forth in the following claims.

I claim:

1. A high energy radiation detector for detecting incoming 0.3 and 30 MeV gamma rays, comprising:

a detector aperture, said aperture limiting said detector to a predetermined field-of-view;

a hodoscope behind said detector aperture comprised of a plurality of detection planes, said detection planes formed of a first type of position sensitive detectors, wherein said incoming gamma rays pass through said detector aperture and are scattered within said hodoscope, said incoming gamma rays forming recoil electrons during passage through said detection planes, wherein said first type of position sensitive detectors determine a track direction at a first scatter vertex and an energy for said recoil electrons; and a calorimeter layer surrounding said hodoscope, said calorimeter comprised of at least one plane of a second type of position sensitive detectors, wherein said scattered gamma rays are totally absorbed within said calorimeter layer, and wherein an energy of said absorbed gamma rays is determined by said calorimeter layer.

2. A non-destructive inspection system capable of detecting 300 keV to 2 MeV x-rays, comprising:

an x-ray source;

a hodoscope positioned to receive x-rays from said x-ray source after said x-rays pass through an object to be inspected, wherein said hodoscope is comprised of a plurality of detection planes, said detection planes formed of a first type of position sensitive detectors, wherein said x-rays are scattered within said hodoscope, said x-rays forming recoil electrons during passage through said detection planes, wherein said first type of position sensitive detectors determine a track direction at a first scatter vertex and an energy for said recoil electrons; and a calorimeter layer surrounding said hodoscope, said calorimeter comprised of at least one plane of a second type of position sensitive detectors, wherein said scattered x-rays are totally absorbed within said calorimeter layer, and wherein an energy of said absorbed x-rays are determined by said calorimeter layer.

3. An energy resolved tomography imaging system, comprising:

a continuous energy x-ray source;

an object to be inspected positioned to receive x-rays from said x-ray source;

means for rotating said object;

a hodoscope positioned to receive x-rays from said x-ray source after said x-rays pass through said object to be inspected, wherein said hodoscope is comprised of a plurality of detection planes, said detection planes formed of a first type of position sensitive detectors, wherein said x-rays are scattered within said hodoscope, said x-rays forming recoil electrons during passage through said detection planes, wherein said first type of position sensitive detectors determine a track direction at a first scatter vertex and an energy for said recoil electrons, and wherein said first type of position sensitive detectors determine an energy associated with unscattered x-rays;

a calorimeter layer surrounding said hodoscope, said calorimeter comprised of at least one plane of a second type of position sensitive detectors, wherein said scattered x-rays are totally absorbed within said calorimeter layer, and wherein an energy of said absorbed x-rays are determined by said calorimeter layer;

a detector readout system coupled to said first type of position sensitive detectors, said readout system receiving an output signal from each individual detector of said first type of position sensitive detectors, said output signal corresponding to said determined energy associated with said unscattered x-rays; and a visual display coupled to said detector readout system, wherein said visual display presents a two dimensional image based on said determined energy associated with said unscattered x-rays.

4. A Compton double scatter single photon emission computed tomography system sensitive to 81 keV through 511 keV gamma ray photons, said system not requiring a collimator to determine the direction of said gamma ray photons, said system comprising:

a detector aperture, said aperture limiting said detector to a predetermined field-of-view;

a hodoscope behind said detector aperture comprised of a plurality of detection planes, said detection planes formed of a first type of position sensitive detectors, wherein said incoming gamma ray photons pass through said detector aperture and are scattered within said hodoscope, said incoming gamma ray photons forming recoil electrons during passage through said detection planes, wherein said first type of position sensitive detectors determine a track direction at a first scatter vertex and an energy for said recoil electrons; and a calorimeter layer surrounding said hodoscope, said calorimeter comprised of at least one plane of a second type of position sensitive detectors, wherein said scattered gamma ray photons are totally absorbed within said calorimeter layer, and wherein an energy of said absorbed gamma ray photons is determined by said calorimeter layer.

5. A Compton double scatter mammography system sensitive to 81 keV through 511 keV gamma ray photons, said system not requiring a collimator to determine the direction of said gamma ray photons, comprising:

a radiotracer with a preferential uptake by malignant breast tumors;

a hodoscope comprised of a plurality of detection planes, said detection planes formed of a first type of position sensitive detectors, wherein said incoming gamma ray photons pass into said hodoscope and are scattered within said hodoscope, said incoming gamma ray photons forming recoil electrons during passage through said detection planes, wherein said first type of position sensitive detectors determine a track direction at a first scatter vertex and an energy for said recoil electrons;

a shield proximate to said hodoscope, said shield limiting access by incoming gamma ray photons to said hodoscope;

a calorimeter layer surrounding said hodoscope, said calorimeter comprised of at least one plane of a second type of position sensitive detectors, wherein said scattered gamma ray photons are totally absorbed within said calorimeter layer, and wherein an energy of said absorbed gamma ray photons is determined by said calorimeter layer;

a multi-channel readout system coupled to said first and second types of position sensitive detectors; and a processor coupled to said multi-channel readout system, said processor time tagging each scatter event.

6. A Compton double scatter positron emission tomography system sensitive to 511 keV photons, said system comprising:

a plurality of hodoscopes positioned in a circular configuration, wherein each of said hodoscopes is comprised of a plurality of position sensitive detector planes, said position sensitive detector planes comprised of a plurality of individual detectors, wherein incoming photons scatter within said position sensitive detector planes creating recoil electrons, and wherein said position sensitive detector planes determine a track direction at each scatter vertex and an energy for each created recoil electron;

a plurality of calorimeters associated with said plurality of hodoscopes, wherein scattered photons are absorbed within said calorimeters, and wherein said calorimeters determine an energy associated with said absorbed photons;

a plurality of passive septa, said septa separating the individual hodoscopes of said plurality of hodoscopes; and a processor for combining said track direction information, said recoil electron energy information, and said absorbed photon energy information to form a series of tomographic slices of an object under view.

* * * * *